(12) United States Patent
Yashiro et al.

(10) Patent No.: US 10,519,105 B2
(45) Date of Patent: Dec. 31, 2019

(54) KCNQ2-5 CHANNEL ACTIVATOR

(71) Applicant: ONO PHARMACEUTICAL CO., LTD., Osaka-shi, Osaka (JP)

(72) Inventors: Kentaro Yashiro, Osaka (JP); Masashi Kato, Osaka (JP); Tetsuji Saito, Osaka (JP); Takuya Okada, Osaka (JP); Daisuke Wakamatsu, Osaka (JP); Adam James Davenport, Abingdon (GB); Christopher Charles Stimson, Abingdon (GB)

(73) Assignee: ONO PHARMACEUTICAL CO., LTD., Osaka-Shi, Osaka (JP)

( * ) Notice: Subject to any disclaimer, the term of this patent is extended or adjusted under 35 U.S.C. 154(b) by 0 days.

(21) Appl. No.: 16/095,374

(22) PCT Filed: Apr. 21, 2017

(86) PCT No.: PCT/JP2017/016100
§ 371 (c)(1),
(2) Date: Oct. 21, 2018

(87) PCT Pub. No.: WO2017/183723
PCT Pub. Date: Oct. 26, 2017

(65) Prior Publication Data
US 2019/0127320 A1    May 2, 2019

(30) Foreign Application Priority Data

Apr. 22, 2016  (JP) ................................ 2016-086241

(51) Int. Cl.
| | | |
|---|---|---|
| *C07C 275/32* | (2006.01) | |
| *C07C 271/30* | (2006.01) | |
| *A61P 13/02* | (2006.01) | |
| *A61K 31/17* | (2006.01) | |
| *A61K 31/27* | (2006.01) | |
| *A61K 31/341* | (2006.01) | |
| *A61K 31/351* | (2006.01) | |
| *A61K 31/4045* | (2006.01) | |
| *A61K 31/42* | (2006.01) | |
| *A61K 31/426* | (2006.01) | |
| *A61K 31/44* | (2006.01) | |
| *A61K 31/4545* | (2006.01) | |
| *A61K 31/4965* | (2006.01) | |
| *A61K 31/505* | (2006.01) | |
| *C07D 213/74* | (2006.01) | |
| *C07D 309/04* | (2006.01) | |
| *C07D 239/26* | (2006.01) | |
| *C07D 241/12* | (2006.01) | |
| *C07D 261/08* | (2006.01) | |
| *C07D 277/28* | (2006.01) | |
| *C07D 209/14* | (2006.01) | |

(Continued)

(52) U.S. Cl.
CPC ............ *C07C 275/32* (2013.01); *A61K 31/17* (2013.01); *A61K 31/27* (2013.01); *A61K 31/341* (2013.01); *A61K 31/351* (2013.01); *A61K 31/4045* (2013.01); *A61K 31/42* (2013.01); *A61K 31/426* (2013.01); *A61K 31/44* (2013.01); *A61K 31/4545* (2013.01); *A61K 31/4965* (2013.01); *A61K 31/505* (2013.01); *A61P 13/02* (2018.01); *A61P 13/10* (2018.01); *C07C 271/30* (2013.01); *C07D 209/14* (2013.01); *C07D 213/40* (2013.01); *C07D 213/64* (2013.01); *C07D 213/74* (2013.01); *C07D 239/26* (2013.01); *C07D 241/12* (2013.01); *C07D 261/08* (2013.01); *C07D 277/28* (2013.01); *C07D 307/52* (2013.01); *C07D 309/04* (2013.01); *C07C 2602/08* (2017.05)

(58) Field of Classification Search
None
See application file for complete search history.

(56) References Cited

U.S. PATENT DOCUMENTS

2008/0234334 A1  9/2008  Chen et al.
2017/0217888 A1  8/2017  Yashiro et al.

FOREIGN PATENT DOCUMENTS

| CN | 104327083 A | 2/2015 |
|---|---|---|
| JP | 2010-511052 | 4/2010 |
| WO | WO-2008/066900 A1 | 6/2008 |
| WO | WO-2016/063990 A1 | 4/2016 |

OTHER PUBLICATIONS

Schafer, S., Kolkhof, P. Failure is an option: learning from unsuccessful proof-of-concept trials. Drug Discovery Today. Nov. 2008, 13, 913-916.*

(Continued)

*Primary Examiner* — Po-Chih Chen
(74) *Attorney, Agent, or Firm* — Foley & Lardner LLP

(57) ABSTRACT

An object of the present invention is to provide a novel compound having a strong opening action with respect to KCNQ2-5 channels. A compound represented by the general formula (I) (wherein the definition of each group is as described in the specification) is provided. The compound represented by the general formula (I) has a strong opening action with respect to KCNQ2-5 channels, and therefore is useful as a prophylactic and/or therapeutic agent for a KCNQ2-5 channel-related disease (for example, dysuria, overactive bladder, or the like).

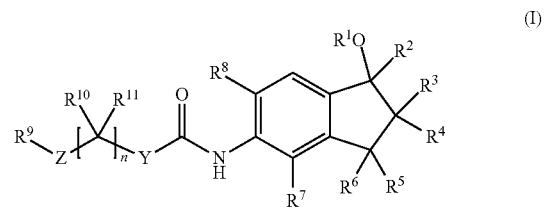

9 Claims, No Drawings

(51) Int. Cl.
*C07D 213/40* (2006.01)
*C07D 213/64* (2006.01)
*C07D 307/52* (2006.01)
*A61P 13/10* (2006.01)

(56) References Cited

OTHER PUBLICATIONS

Horig, H., Pullman, W. From bench to clinic and back: Perspective on the 1st IQPC Translational Research conference. Journal of Translational Medicine. Dec. 2004, 2, 44.*
Ito et al., A medium-term rat livery bioassay for rapid in vivo detection of carcinogenic potential of chemicals. Cancer Science, 2003, 94, 3-8.*
Kumar et al., Synthesis and Evaluation of Potent KCNQ2/3-Specific Channel Activators. Molecular Pharmacology, 2016, 89, 667-677.*
International Search Report for PCT/JP2017/016100 dated Jul. 6, 2017.
Current Topics in Medicinal Chemistry, 2006, vol. 6, pp. 999-1023.
The Journal of Urology, , 2004, vol. 172, pp. 2054-2058.
European Journal of Pharmacology, 2010, vol. 638, pp. 121-127.
RN 1026819-61-3, Jun. 9, 2008, Registry [online] American Chemical Society [retrieved on Jul. 5, 2017], Retrieved from: STN.
Written Opinion of the International Search Authority for PCT/JP2017/016100 dated Jul. 6, 2017.

* cited by examiner

KCNQ2-5 CHANNEL ACTIVATOR

CROSS-REFERENCE TO RELATED APPLICATIONS

This is a U.S. national stage application claiming the benefit of International Patent Application No. PCT/JP2017/016100 filed Apr. 21, 2017, which claims priority to Japanese Patent Application No. 2016-086241, filed Apr. 22, 2016.

TECHNICAL FIELD

The present invention relates to a compound represented by the general formula (I) or a pharmaceutically acceptable salt thereof, etc.

[Chem. 1]

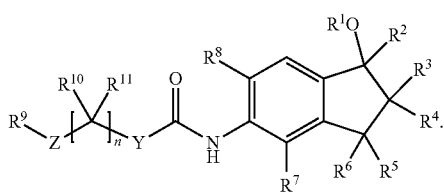

(I)

(wherein all symbols represent the same meanings as described below.)

BACKGROUND ART

It has been confirmed that a KCNQ channel has five subtypes including KCNQ1, KCNQ2, KCNQ3, KCNQ4, and KCNQ5. Among them, KCNQ2-5 other than KCNQ1 are expressed in the nociceptive sensory system such as spinal dorsal root ganglion and spinal cord. The activation of the KCNQ2-5 channels causes hyperpolarization of nerve cells in a nociceptive signal pathway.

It has been reported that a KCNQ2-5 channel activator is useful for treating many disorders characterized by abnormal neuronal excitability including epilepsy, pain, migraine, and anxiety disorder (see Non-Patent Document 1). In fact, retigabine which is a KCNQ2-5 channel activator has already been marketed as an antiepileptic drug.

Further, it has also been recently reported that retigabine is useful for treating bladder disorder (overactive bladder or the like) (see Non-Patent Documents 2 and 3).

Overactive bladder is considered to be caused by a state of potential overactivity of the detrusor muscle, and therefore, a muscarinic receptor antagonist mainly having a suppressive action on bladder contraction has been widely used for its treatment. However, the muscarinic receptor is present not only in the bladder but also in the salivary gland, the intestinal tract, the ciliary muscle, and the like, and the muscarinic receptor has also a functional role. Therefore, adverse effects such as dry mouth, constipation, and blurred vision sometimes occur, and also there is a concern that the suppressive action on bladder contraction of the muscarinic receptor antagonist may cause adverse effects such as difficulty in urination, an increase in the amount of residual urine, and urinary retention, and it cannot be said that a satisfactory therapeutic effect is always achieved. Further, as a drug to overcome the problems of the muscarinic receptor antagonist, a selective β3 adrenergic receptor agonist was put on the market in 2011 in Japan. It is suggested that the selective β3 adrenergic receptor agonist hardly affects the urination function while enhancing the urine collection function by a bladder relaxing action, and it exhibits the bladder relaxing action independent of contraction stimulation, and therefore is expected to work in a wide range of patients. On the other hand, the risk of QT extension increases with an increase in the dose and it shows a heart rate increasing action by acting on the cardiac β receptor, and therefore, these are limiting factors for the dose.

From the above, in this field, a drug which has a bladder relaxing action independent of contraction stimulation and is free from fear of adverse effects has been demanded, and a KCNQ2-5 channel activator is expected as a drug which responds to these unmet medical needs.

Until now, as a KCNQ activator having an indane skeleton, for example, a compound represented by the general formula (a) is known (see Patent Document 1).

[Chem. 2]

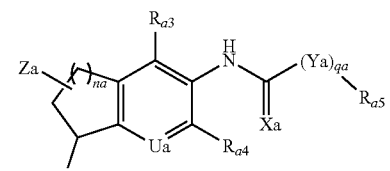

(a)

(wherein Ga is —O—, —S—, or the like; na is 1, 2, or 3; $Ar_{a1}$ is independently a 5- to 10-membered monocyclic or bicyclic aromatic group optionally containing one to four heteroatoms independently selected from N, O, and S; $R_{a1}$ and $R_{a2}$ are independently selected from H, CN, a halogen, $CH_2CN$, OH, $NO_2$, and the like; Ua is N or CRa'; Ra', $R_{a3}$, and $R_{a4}$ are independently H, a halogen, trifluoromethyl, or the like; Xa is O or S; Ya is O or S; Za is H, a halogen, OH, $C_{1-6}$ alkyl, or the like; qa is 1 or 0; $R_{a5}$ is $C_{1-6}$ alkyl, $Ar_{a2}$, $(CHR_{6a})_{wa}Ar_{a2}$, or the like, wherein wa is 0 to 3, and each $Ar_{a2}$ is independently a 5- to 10-membered monocyclic or bicyclic aromatic group optionally containing one to four cyclic heteroatoms independently selected from N, O, and S; and $R_{6a}$ is H or $C_{1-3}$ alkyl (the definitions of the groups are partially extracted).

However, the compound of the present invention is not included in the general formula (a) of Patent Document 1. Further, Patent Document 1 does not describe or suggest a technique for converting the compound described in Patent Document 1 into the compound of the present invention.

CITED REFERENCES

Patent Documents

Patent Document 1: International Publication number WO 2008/066990

Non-Patent Documents

Non-Patent Document 1: Current Topics in Medicinal Chemistry, vol. 6, pp. 999-1023, 2006,
Non-Patent Document 2: The Journal of Urology, vol. 172, pp. 2054-2058, 2004

Non-Patent Document 3: European Journal of Pharmacology, vol. 638, pp. 121-127, 2010

DISCLOSURE OF THE INVENTION

Problems to be Solved by the Invention

An object of the present invention is to provide a compound having a strong opening action with respect to KCNQ2-5 channels.

Means for Solving the Problems

The present inventors made intensive studies to achieve the above object, and as a result, they found that the compound of the present invention is a compound having a strong opening action with respect to KCNQ2-5 channels. Further, the present inventors found that the compound of the present invention has excellent solubility, stability, and/or safety, and thus, completed the present invention.

That is, the present invention relates to:

(1) a compound represented by the general formula (I) or a pharmaceutically acceptable salt thereof:

[Chem. 3]

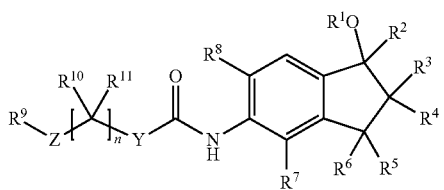

(I)

(wherein $R^1$ is (1) a hydrogen atom or (2) a $C_{1-4}$ alkyl group; $R^2$ is (1) a hydrogen atom or (2) a $C_{1-4}$ alkyl group which may be substituted with a halogen; $R^3$, $R^4$. $R^5$, and $R^6$ are each independently (1) a hydrogen atom. (2) a halogen, or (3) a $C_{1-4}$ alkyl group which may be substituted with a halogen; $R^7$ and $R^8$ are each independently (1) a hydrogen atom, (2) a halogen, (3) a $C_{1-4}$ alkyl group which may be substituted with a halogen, or (4) a $C_{1-4}$ alkoxy group which may be substituted with a halogen, with the proviso that $R^7$ and $R^8$ are not simultaneously a hydrogen atom; Y is (1) a bond, (2) —NH—, or (3) —O—; Z is (1) a bond, (2) —$NR^{12}$—, or (3) —O—; $R^{12}$ is (1) a hydrogen atom, (2) a $C_{1-4}$ alkyl group which may be substituted with a halogen, or (3) a $C_{2-5}$ acyl group which may be substituted with a halogen; $R^{10}$ and $R^{11}$ are each independently (1) a hydrogen atom or (2) a $C_{1-4}$ alkyl group which may be substituted with a halogen or a hydroxy group; n is an integer of 1 to 4, and when n is 2 to 4, a plurality of $R^{10}$'s or a plurality of $R^{11}$'s may be the same as or different from one another; $R^9$ is (1) a ring A, (2) a $C_{1-4}$ alkyl group, (3) a $C_{2-4}$ alkenyl group, (4) a $C_{2-4}$ alkynyl group, (5) —$C_{1-4}$ alkylene group-ring A, (6) —$C_{2-4}$ alkenylene group-ring A, (7) —$C_{2-4}$ alkynylene group-ring A, (8) -ring B-ring C, (9) -ring B—$C_{1-4}$ alkylene group-ring C, (10) -ring B—$C_{2-4}$ alkenylene group-ring C, (11) -ring B—$C_{2-4}$ alkynylene group-ring C, or (12) -ring B—O-ring C, where the alkyl group, the alkenyl group, the alkynyl group, the alkylene group, the alkenylene group, or the alkynylene group each may be substituted with a halogen or a hydroxy group; the ring A is (1) a $C_{3-8}$ cycloalkane, (2) a 3- to 8-membered heterocycloalkane, (3) a $C_{3-12}$ monocyclic or bicyclic unsaturated carbocyclic ring or the carbocyclic ring which may be partially saturated, or (4) a 3- to 12-membered monocyclic or bicyclic unsaturated heterocycle containing one to four heteroatoms selected from an oxygen atom, a nitrogen atom, and a sulfur atom or the heterocycle which may be partially saturated; the ring B and the ring C are each independently (1) a $C_{3-4}$ monocyclic cycloalkane, (2) a 3- to 8-membered monocyclic heterocycloalkane, (3) a $C_{3-7}$ monocyclic unsaturated carbocyclic ring or the carbocyclic ring which may be partially saturated, or (4) a 3- to 7-membered monocyclic unsaturated heterocycle containing one to three heteroatoms selected from an oxygen atom, a nitrogen atom, and a sulfur atom or the heterocycle which may be partially saturated; where the ring A, the ring B, and the ring C may be each independently substituted with one to five $R^{13}$'s, and when a plurality of $R^{13}$'s is present, the $R^{13}$'s may be the same as or different from one another; $R^{13}$ is (1) a halogen, (2) a hydroxy group, (3) a cyano group, (4) a $C_{1-6}$ alkyl group which may be substituted with a halogen or a hydroxy group, (5) a $C_{1-6}$ alkoxy group which may be substituted with a halogen or a hydroxy group, or (6) an amino group which may be substituted with a $C_{1-4}$ alkyl group or a $C_{2-5}$ acyl group):

(2) the compound or a pharmaceutically acceptable salt thereof according to the above (1), wherein $R^1$ is a hydrogen atom:

(3) the compound or a pharmaceutically acceptable salt thereof according to the above (1) or (2), wherein Y is —NH— or —O—;

(4) the compound or a pharmaceutically acceptable salt thereof according to any one of the above (1) to (3), wherein Z is a bond or —O—;

(5) the compound or a pharmaceutically acceptable salt thereof according to any one of the above (1) to (4), wherein $R^2$ is a hydrogen atom, a methyl group, or a trifluoromethyl group;

(6) the compound or a pharmaceutically acceptable salt thereof according to the above (1), wherein the compound is represented by the general formula (III):

[Chem. 4]

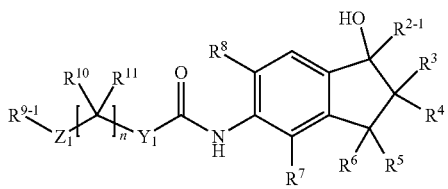

(III)

(wherein $Y_1$ is —NH— or —O—; $Z_1$ is a bond or —O—; $R^{2-1}$ is a hydrogen atom, a methyl group, or a trifluoromethyl group; $R^{9-1}$ is (1) a ring A or (2) -ring B-ring C, where the ring A, the ring B, and the ring C may be each independently substituted with one to five $R^{13}$'s, and when a plurality of $R^{13}$'s is present, the $R^{13}$'s may be the same as or different from one another);

(7) the compound or a pharmaceutically acceptable salt thereof according to any one of the above (1) to (6), wherein $R^3$, $R^4$, $R^5$, and $R^6$ are each independently (1) a hydrogen atom, (2) a halogen, or (3) a methyl group which may be substituted with a halogen;

(8) the compound or a pharmaceutically acceptable salt thereof according to any one of the above (1) to (7), wherein $R^7$ and $R^8$ are each independently (1) a hydrogen atom, (2) a halogen, or (3) a methyl group which may be substituted with a halogen (with the proviso that $R^7$ and $R^8$ are not simultaneously a hydrogen atom);

(9) the compound or a pharmaceutically acceptable salt thereof according to any one of the above (1) to (8), wherein $R^7$ and $R^8$ are each independently a halogen;

(10) the compound or a pharmaceutically acceptable salt thereof according to any one of the above (1) to (9), wherein $R^{10}$ and $R^{11}$ are each independently a hydrogen atom or a methyl group;

(11) the compound or a pharmaceutically acceptable salt thereof according to any one of the above (1) to (10), wherein n is 1 or 2;

(12) the compound or a pharmaceutically acceptable salt thereof according to the above (1), wherein the compound is (1) 1-(4,6-dichloro-1-hydroxy-1-methyl-2,3-dihydro-1H-inden-5-yl)-3-{[5-(trifluoromethyl)-2-pyridinyl]methyl}urea, (2) 1-[4,6-dichloro-1-hydroxy-1-(trifluoromethyl)-2,3-dihydro-1H-inden-5-yl]-3-(4-fluorobenzyl)urea, (3) 1-[4,6-dichloro-1-hydroxy-1-(trifluoromethyl)-2,3-dihydro-1H-inden-5-yl]-3-{[5-(trifluoromethyl)-2-pyridinyl]methyl}urea, (4) 1-[4,6-dichloro-1-hydroxy-1-(trifluoromethyl)-2,3-dihydro-1H-inden-5-yl]-3-[(1R)-1-(4-fluorophenyl)ethyl] urea, or (5) 1-(4,6-dichloro-2,2-difluoro-1-hydroxy-1-methyl-2,3-dihydro-1H-inden-5-yl)-3-(4-fluorobenzyl)urea;

(13) the compound or a pharmaceutically acceptable salt thereof according to claim 1, wherein the compound is 1-[(1R)-4,6-dichloro-1-hydroxy-1-(trifluoromethyl)-2,3-dihydro-1H-inden-5-yl]-3-[(1R)-1-(4-fluorophenyl)ethyl]urea or 1-[(1S)-4,6-dichloro-1-hydroxy-1-(trifluoromethyl)-2,3-dihydro-1H-inden-5-yl]-3-[(1R)-1-(4-fluorophenyl)ethyl] urea;

(14) a pharmaceutical composition comprising a compound represented by the general formula (I) or a pharmaceutically acceptable salt thereof and a pharmaceutically acceptable carrier;

(15) the pharmaceutical composition according to the above (14), which is a prophylactic and/or therapeutic agent for a KCNQ2-5 channel-related disease:

(16) the pharmaceutical composition according to the above (15), wherein the KCNQ2-5 channel-related disease is dysuria;

(17) the pharmaceutical composition according to the above (16), wherein the dysuria is overactive bladder;

(18) a prophylactic and/or therapeutic agent for a KCNQ2-5 channel-related disease, comprising a compound represented by the general formula (I) or a pharmaceutically acceptable salt thereof;

(19) a method for preventing and/or treating a KCNQ2-5 channel-related disease, the method comprising: administering an effective amount of a compound represented by the general formula (I) or a pharmaceutically acceptable salt thereof to a mammal;

(20) a compound represented by the general formula (I) or a pharmaceutically acceptable salt thereof for preventing and/or treating a KCNQ2-5 channel-related disease;

(21) use of a compound represented by the general formula (I) or a pharmaceutically acceptable salt thereof for manufacturing a prophylactic and/or therapeutic agent for a KCNQ2-5 channel-related disease; and the like.

Effect of the Invention

The compound of the present invention has a KCNQ2-5 channel opening action and is useful as a therapeutic agent for a KCNQ2-5 channel-related disease.

EMBODIMENTS FOR CARRYING OUT THE INVENTION

Hereinafter, the present invention will be described in detail.

In the present invention, the $C_{1-4}$ alkyl group means a linear or branched $C_{1-4}$ alkyl group. Examples of the $C_{1-4}$ alkyl group include methyl, ethyl, propyl, isopropyl, butyl, sec-butyl, and tert-butyl.

In the present invention, the $C_{1-6}$ alkyl group means a linear or branched $C_{1-6}$ alkyl group. Examples of the $C_{1-6}$ alkyl group include methyl, ethyl, propyl, isopropyl, butyl, sec-butyl, tert-butyl, pentyl, isopentyl, tert-pentyl, neopentyl, hexyl, isohexyl, 3-methylpentyl, and the like.

In the present invention, the $C_{2-5}$ acyl group means a linear or branched $C_{2-5}$ acyl group. Examples of the $C_{2-5}$ acyl group include acetyl, propionyl, butanoyl, pentanoyl, and the like.

In the present invention, the $C_{2-4}$ alkenyl group means a linear or branched $C_{2-4}$ alkenyl group having at least one carbon-carbon double bond. Examples of the $C_{2-4}$ alkenyl group include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

In the present invention, the $C_{2-4}$ alkynyl group means a linear or branched $C_{2-4}$ alkynyl group having at least one carbon-carbon triple bond. Examples of the $C_{2-4}$ alkynyl group include ethynyl, 1-propyn-1-yl, 2-propyn-1-yl, 1-butyn-1-yl, 3-butyn-1-yl, 3-butyn-2-yl, 2-butyn-1-yl, and the like.

In the present invention, the $C_{1-4}$ alkylene group means a linear or branched $C_{1-4}$ alkylene group. Examples of the $C_{1-4}$ alkylene group include methylene, ethylene, methylmethylene, ethylmethylene, propylene, butylene, isopropylene, isobutylene, sec-butylene, tert-butylene, and the like.

In the present invention, the $C_{2-4}$ alkenylene group means a linear or branched $C_{2-4}$ alkenylene group. Examples of the $C_{2-4}$ alkenylene group include ethenylene, 1-propenylene, 2-propenylene, 1-butenylene, 2-butenylene, 3-butenylene, and the like.

In the present invention, the $C_{2-4}$ alkynylene group means a linear or branched $C_{2-4}$ alkynylene group. Examples of the $C_{2-4}$ alkynylene group include ethynylene, 1-propynylene, 2-propynylene, 1-butynylene, 2-butynylene, 3-butynylene, and the like.

In the present invention, the $C_{1-4}$ alkoxy group means a linear or branched $C_{1-4}$ alkoxy group. Examples of the $C_{1-4}$ alkoxy group include methoxy, ethoxy, propoxy, isopropoxy, butoxy, isobutyloxy, tert-butoxy, and the like.

In the present invention, the $C_{1-6}$ alkoxy group means a linear or branched $C_{1-6}$ alkoxy group. Examples of the $C_{1-6}$ alkoxy group include methoxy, ethoxy, propoxy, isopropoxy, butoxy, isobutyloxy, tert-butoxy, pentyloxy, isopentyloxy, tert-pentyloxy, neopentyloxy, hexyloxy, and the like.

In the present invention, the halogen means fluorine, chlorine, bromine, iodine, or the like.

In the present invention, the $C_{3-8}$ cycloalkane is a $C_{3-8}$ saturated hydrocarbon ring and may have a spiro bond or crosslinking. Examples of the $C_{3-8}$ cycloalkane include cyclopropane, cyclobutane, cyclopentane, cyclohexane, bicyclo[2.2.1]heptane, bicyclo[3.1.1]heptane, bicyclo[2.2.2] octane, cycloheptane, cyclooctane, perhydropentalene, cubane, and the like.

In the present invention, the $C_{3-8}$ monocyclic cycloalkane may have a spiro bond or crosslinking. Specific examples of the $C_{3-8}$ monocyclic cycloalkane include cyclopropane, cyclobutane, cyclopentane, cyclohexane, cycloheptane, cyclooctane, bicyclo[2.2.1]heptane, bicyclo[3.1.1]heptane, and bicyclo[2.2.2]octane.

In the present invention, the 3- to 8-membered heterocycloalkane is a 3- to 8-membered saturated heterocycle containing one to three heteroatoms selected from an oxygen atom, a nitrogen atom, and a sulfur atom, and may have a spiro bond or crosslinking. Specific examples of the 3- to 8-membered heterocycloalkane include aziridine, oxirane, thiirane, azetidine, oxetane, thietane, pyrrolidine, tetrahydrofuran, tetrahydrothiophene, piperidine, tetrahydropyran, tetrahydrothiopyran, azabicyclo[2.2.1]heptane, oxabicyclo[2.2.1]heptane, azabicyclo[3.1.1]heptane, azabicyclo[2.2.2]octane, perhydroazepine, perhydrooxepine, perhydrothiepine, azabicyclo[3.2.1]octane, oxabicyclo[3.2.1]octane, imidazolidine, pyrazolidine, tetrahydrooxazole (oxazolidine), tetrahydroisoxazole (isoxazolidine), tetrahydrothiazole (thiazolidine), tetrahydroisothiazole (isothiazolidine), dioxolane, dithiolane, piperazine, perhdropyrimidine, perhydropyridazine, tetrahydroxazine, tetrahydrothiazine, morpholine, thiomorpholine, oxathiane, dioxane, dithiane, diazabicyclo[2.2.2]octane, perhydrodiazepine, perhydrooxazepine, perhydrothiazepine, triazolidine, tetrahydrofurazan, tetrahydrooxadiazole (oxadiazolidine), tetrahydrothiadiazole (thiadiazolidine), tetrahydrooxadiazine, tetrahydrothiadiazine, perhydrooxadiazepine, perhydrothiadiazepine, and the like.

In the present invention, the 3- to 8-membered monocyclic heterocycloalkane is a 3- to 8-membered monocyclic saturated heterocycle containing one to three heteroatoms selected from an oxygen atom, a nitrogen atom, and a sulfur atom, and may have a spiro bond or crosslinking. Specific examples of the 3- to 8-membered monocyclic heterocycloalkane include aziridine, oxirane, thiirane, azetidine, oxetane, thietane, pyrrolidine, imidazolidine, triazolidine, pyrazolidine, tetrahydrofuran, tetrahydrothiophene, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrothiadiazole (thiadiazolidine), dioxolane, dithiolane, piperidine, piperazine, perhydropyrimidine, perhydropyridazine, tetrahydropyran, tetrahydrothiopyran, tetrahydroxazine, tetrahydrooxadiazine, tetrahydrothiazine, tetrahydrothiadiazine, morpholine, thiomorpholine, oxathiane, dioxane, dithiane, azabicyclo[2.2.1]heptane, oxabicyclo[2.2.1]heptane, azabicyclo[3.1.1]heptane, azabicyclo[2.2.2]octane, diazabicyclo[2.2.2]octane, perhydroazepine, perhydrodiazepine, perhydrooxepine, perhydrothiepine, perhydrooxazepine, perhydrooxadiazepine, perhydrothiazepine, perhydrothiadiazepine, azabicyclo[3.2.1]octane, oxabicyclo[3.2.1]octane, and the like.

In the present invention, the 3- to 7-membered monocyclic heterocycloalkane containing one oxygen atom or nitrogen atom as the heteroatom may have a spiro bond or crosslinking. Specific examples of the 3- to 7-membered monocyclic heterocycloalkane containing one oxygen atom or nitrogen atom as the heteroatom include aziridine, oxirane, azetidine, oxetane, pyrrolidine, tetrahydrofuran, piperidine, tetrahydropyran, perhydroazepine, perhydrooxepine, and the like.

In the present invention, specific examples of the "$C_{3-12}$ monocyclic or bicyclic unsaturated carbocyclic ring or the carbocyclic ring which may be partially saturated" include cyclopropene, cyclobutene, cyclopentene, cyclopentadiene, cyclohexene, cyclohexadiene, benzene, cycloheptene, cycloheptadiene, cyclooctene, cyclooctadiene, pentalene, indene, indan, dihydronaphthalene, tetrahydronaphthalene, azulene, naphthalene, heptalene, and the like.

In the present invention, specific examples of the "$C_{3-7}$ monocyclic unsaturated carbocyclic ring or the carbocyclic ring which may be partially saturated" include cyclopropene, cyclobutene, cyclopentene, cyclopentadiene, cyclohexene, cyclohexadiene, benzene, cycloheptene, cycloheptadiene, and the like.

In the present invention, specific examples of the "$C_{5-7}$ monocyclic unsaturated carbocyclic ring or the carbocyclic ring which may be partially saturated" include cyclopentene, cyclopentadiene, cyclohexene, cyclohexadiene, benzene, cycloheptene, cycloheptadiene, and the like.

In the present invention, specific examples of the "$C_{8-10}$ bicyclic unsaturated carbocyclic ring or the carbocyclic ring which may be partially saturated" include pentalene, indene, indan, dihydronaphthalene, tetrahydronaphthalene, azulene, naphthalene, and the like.

In the present invention, specific examples of the "3- to 12-membered monocyclic or bicyclic unsaturated heterocycle containing one to four heteroatoms selected from an oxygen atom, a nitrogen atom, and a sulfur atom or the heterocycle which may be partially saturated" include azirine, oxirene, thiirene, azete, pyrroline, imidazoline, triazoline, tetrazoline, pyrazoline, dihydrofuran, dihydrothiophene, dihydrooxazole, dihydroisoxazole, dihydrothiazole, dihydroisothiazole, dihydrofurazan, dihydrooxadiazole, dihydrothiadiazole, pyrrole, imidazole, triazole, tetrazole, pyrazole, furan, thiophene, oxazole, isoxazole, thiazole, isothiazole, furazan, oxadiazole, thiadiazole, pyran, thiopyran, oxazine, oxadiazine, thiazine, thiadiazine, dihydropyridine, tetrahydropyridine, dihydropyrazine, tetrahydropyrazine, dihydropyrimidine, tetrahydropyrimidine, dihydropyridazine, tetrahydropyridazine, dihydropyran, dihydrothiopyran, dihydrooxazine, dihydrooxadiazine, dihydrothiazine, dihydrothiadiazine, pyridine, pyrazine, pyrimidine, pyridazine, azepine, diazepine, oxepine, thiepine, oxazepine, oxadiazepine, thiazepine, thiadiazepine, dihydroazepine, tetrahydroazepine, dihydrodiazepine, tetrahydrodiazepine, dihydrooxepine, tetrahydrooxepine, dihydrothiepine, tetrahydrothiepine, dihydrooxazepine, tetrahydrooxazepine, dihydrooxadiazepine, tetrahydrooxadiazepine, dihydrothiazepine, tetrahydrothiazepine, dihydrothiadiazepine, tetrahydrothiadiazepine, indolizine, indoline, isoindoline, dihydrobenzofuran, dihydroisobenzofuran, dihydrobenzothiophene, dihydroisobenzothiophene, dihydroindazole, dihydrobenzoxazole, dihydrobenzothiazole, dihydrobenzimidazole, dioxaindan, benzodithiolane, indole, isoindole, benzofuran, isobenzofuran, benzothiophene, isobenzothiophene, indazole, purine, benzoxazole, benzothiazole, benzimidazole, benzofurazan, benzothiadiazole, benzotriazole, dithianaphthalene, quinolizine, chromene, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzooxathiane, dihydrobenzooxazine, dihydrobenzothiazine, pyrazinomorpholine, benzodioxan, chroman, benzodithiane, quinoline, isoquinoline, phthalazine, pteridine, naphthyridine, quinoxaline, quinazoline, cinnoline, benzooxepine, benzooxazepine, benzooxadiazepine, benzothiepine, benzothiazepine, benzothiadiazepine, benzoazepine, benzodiazepine, dihydrobenzoazepine, tetrahydrobenzoazepine, dihydrobenzodiazepine, tetrahydrobenzodiazepine, benzodioxepane, dihydrobenzooxazepine, tetrahydrobenzooxazepine, and the like.

In the present invention, specific examples of the "3- to 7-membered monocyclic unsaturated heterocycle containing one to three heteroatoms selected from an oxygen atom, a nitrogen atom, and a sulfur atom or the heterocycle which may be partially saturated" include azirine, oxirene, thiirene, azete, pyrroline, dihydrofuran, dihydrothiophene, pyrrole, furan, thiophene, pyran, thiopyran, dihydropyridine, tetrahydropyridine, dihydropyran, dihydrothiopyran, pyridine, azepine, oxepine, thiepine, dihydroazepine, tetrahydroazepine, dihydrooxepine, tetrahydrooxepine, dihydrothiepine, tetrahydrothiepine, imidazoline, pyrazoline, dihydrooxazole, dihydroisoxazole, dihydrothiazole, dihydroisothiazole, imidazole, pyrazole, oxazole, isoxazole, thiazole, isothiazole, oxazine, thiazine, dihydropyrazine, tetrahydropyrazine, dihydropyrimidine, tetrahydropyrimidine, dihydropyridazine, tetrahydropyridazine, dihydrooxazine, dihydrothiazine, pyrazine, pyrimidine, pyridazine, diazepine, oxazepine, thiazepine, dihydrodiazepine, tetrahydrodiazepine, dihydrooxazepine, tetrahydrooxazepine, dihydrothiazepine, tetrahydrothiazepine, triazoline, dihydrofurazan, dihydrooxadiazole, dihydrothiadiazole, triazole, furazan, oxadiazole, thiadiazole, oxadiazine, thiadiazine, dihydrooxadiazine, dihydrothiadiazine, oxadiazepine, thiadiazepine, dihydrooxadiazepine, tetrahydrooxadiazepine, dihydrothiadiazepine, tetrahydrothiadiazepine, and the like.

In the present invention, specific examples of the "5- to 7-membered monocyclic unsaturated heterocycle containing one to three heteroatoms selected from an oxygen atom, a nitrogen atom, and a sulfur atom or the heterocycle which may be partially saturated" include pyrroline, dihydrofuran, dihydrothiophene, pyrrole, furan, thiophene, pyran, thiopyran, dihydropyridine, tetrahydropyridine, dihydropyran, dihydrothiopyran, pyridine, azepine, oxepine, thiepine, dihydroazepine, tetrahydroazepine, dihydrooxepine, tetrahydrooxepine, dihydrothiepine, tetrahydrothiepine, imidazoline, pyrazoline, dihydrooxazole, dihydroisoxazole, dihydrothiazole, dihydroisothiazole, imidazole, pyrazole, oxazole, isoxazole, thiazole, isothiazole, oxazine, thiazine, dihydropyrazine, tetrahydropyrazine, dihydropyrimidine, tetrahydropyrimidine, dihydropyridazine, tetrahydropyridazine, dihydrooxazine, dihydrothiazine, pyrazine, pyrimidine, pyridazine, diazepine, oxazepine, thiazepine, dihydrodiazepine, tetrahydrodiazepine, dihydrooxazepine, tetrahydrooxazepine, dihydrothiazepine, tetrahydrothiazepine, triazoline, dihydrofurazan, dihydrooxadiazole, dihydrothiadiazole, triazole, furazan, oxadiazole, thiadiazole, oxadiazine, thiadiazine, dihydrooxadiazine, dihydrothiadiazine, oxadiazepine, thiadiazepine, dihydrooxadiazepine, tetrahydrooxadiazepine, dihydrothiadiazepine, tetrahydrothiadiazepine, and the like.

In the present invention, specific examples of the "9- to 10-membered bicyclic unsaturated heterocycle containing one to four heteroatoms selected from an oxygen atom, a nitrogen atom, and a sulfur atom or the heterocycle which may be partially saturated" include indolizine, indoline, isoindoline, dihydrobenzofuran, dihydroisobenzofuran, dihydrobenzothiophene, dihydroisobenzothiophene, dihydroindazole, dihydrobenzoxazole, dihydrobenzothiazole, dihydrobenzimidazole, dioxaindan, benzodithiolane, quinolizine, chromene, dihydroquinoline, tetrahydroquinoline, dihydroisoquinoline, tetrahydroisoquinoline, chroman, dithianaphthalene, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzooxathiane, dihydrobenzooxazine, dihydrobenzothiazine, benzodioxan, benzodithiane, pyrazinomorpholine, indole, isoindole, benzofuran, isobenzofuran, benzothiophene, isobenzothiophene, indazole, benzoxazole, benzothiazole, benzimidazole, benzofurazan, benzothiadiazole, benzotriazole, purine, quinoline, isoquinoline, phthalazine, naphthyridine, quinoxaline, quinazoline, cinnoline, pteridine, and the like.

In the present invention, when the number of substituents is not specified, the number of substituents, if present, is intended to be one or more.

In the present invention, each substituent is independently defined for each occurrence in the definition in the general formula. For example, when more than one substituent $R^{13}$ is present on the "ring A" or the "ring B" and/or the "ring C", respectively, each substituent is selected independently for each occurrence, and the respective substituents may be the same as or different from each other.

In the present invention, the KCNQ2-5 channels mean KCNQ channels, each of which is a homotetramer or a heterotetramer formed by four molecules of the respective subtypes among the KCNQ2 to KCNQ5 subtypes assembling together. Examples thereof include homotetramers such as KCNQ2, KCNQ3, KCNQ4, and KCNQ5 channels and heterotetramers such as KCNQ2/3, KCNQ3/4, and KCNQ3/5 channels. Preferred are KCNQ2/3, KCNQ4 and/or KCNQ5 channel.

In the present invention, the KCNQ2-5 channel activator means a compound having an opening action with respect to the KCNQ2-5 channels (preferably KCNQ2/3, KCNQ4 and/or KCNQ5 channel). In the present invention, a KCNQ channel activation action has the same meaning as that of a KCNQ channel opening action.

In the present invention, $R^1$ is preferably a hydrogen atom or a methyl group, and more preferably a hydrogen atom.

In the present invention, Y is preferably —NH— or —O—, and more preferably —NH—.

In the present invention, Z is preferably a bond or —O—, and more preferably a bond.

In the present invention, $R^2$ is preferably a hydrogen atom, or a $C_{1-2}$ alkyl group (a methyl group or an ethyl group) which may be substituted with a halogen, more preferably a hydrogen atom or a methyl group which may be substituted with a halogen, and further more preferably a hydrogen atom, a methyl group, or a trifluoromethyl group.

In the present invention, $R^3$, $R^4$, $R^5$, and $R^6$ are each preferably a hydrogen atom, a halogen, or a $C_{1-2}$ alkyl group which may be substituted with a halogen, each more preferably a hydrogen atom, a halogen, or a methyl group which may be substituted with a halogen, and each further more preferably a hydrogen atom, a halogen (preferably fluorine), or a methyl group.

In the present invention, $R^7$ and $R^8$ are each preferably a hydrogen atom, a halogen, or a $C_{1-4}$ alkyl group which may be substituted with a halogen, each more preferably a hydrogen atom, a halogen, or a methyl group which may be substituted with a halogen, each further more preferably a halogen or a methyl group, and each particularly preferably a halogen (preferably chlorine).

In the present invention. $R^{10}$ and $R^{11}$ are each preferably a hydrogen atom or a methyl group, and more preferably a hydrogen atom.

In the present invention, n is preferably 1 or 2.

In the present invention, $R^9$ is preferably (1) a $C_{1-4}$ alkyl group which may be substituted with a halogen or a hydroxy group, (2) a ring A, or (3) -ring B-ring C, and more preferably (1) a ring A or (2) -ring B-ring C. Here, the ring A, the ring B, and the ring C may be each independently substituted with one to five $R^{13}$'s.

In the present invention, the ring A is preferably (1) a $C_{3-8}$ cycloalkane (preferably a $C_{3-8}$ monocyclic cycloalkane), (2) a 3- to 8-membered heterocycloalkane (preferably a 3- to 8-membered monocyclic heterocycloalkane, and more preferably a 3- to 7-membered monocyclic heterocycloalkane containing one oxygen atom or a nitrogen atom as a heteroatom), (3) a $C_{3-7}$ monocyclic unsaturated carbocyclic ring or the carbocyclic ring which may be partially saturated (preferably a $C_{5-7}$ monocyclic unsaturated carbocyclic ring or the carbocyclic ring which may be partially saturated), (4) a $C_{8-10}$ bicyclic unsaturated carbocyclic ring or the carbocyclic ring which may be partially saturated, (5) a 3- to 7-membered monocyclic unsaturated heterocycle containing one to three heteroatoms selected from an oxygen atom, a nitrogen atom, and a sulfur atom or the heterocycle which may be partially saturated (preferably a 5- to 7-membered monocyclic unsaturated heterocycle containing one to three heteroatoms selected from an oxygen atom, a nitrogen atom, and a sulfur atom or the heterocycle which may be partially saturated), or (6) a 9- to 10-membered bicyclic unsaturated heterocycle containing one to four heteroatoms selected from an oxygen atom, a nitrogen atom, and a sulfur atom or the heterocycle which may be partially saturated, where the respective rings may be each independently substituted with one to five $R^{13}$'s.

In the present invention, the ring B or the ring C is preferably (1) a 3- to 8-membered monocyclic heterocycloalkane, (2) a $C_{3-7}$ monocyclic unsaturated carbocyclic ring or the carbocyclic ring which may be partially saturated, or (3) a 3- to 7-membered monocyclic unsaturated heterocycle containing one to three heteroatoms selected from an oxygen atom, a nitrogen atom, and a sulfur atom or the heterocycle which may be partially saturated, where the respective rings may be each independently substituted with one to five $R^{13}$'s.

In the present invention, the 3- to 8-membered monocyclic heterocycloalkane as the ring B or the ring C is preferably a 3- to 7-membered monocyclic heterocycloalkane containing one oxygen atom or nitrogen atom as the heteroatom.

In the present invention, the $C_{3-7}$ monocyclic unsaturated carbocyclic ring or the carbocyclic ring which may be partially saturated as the ring B or the ring C is preferably a $C_{5-7}$ monocyclic unsaturated carbocyclic ring or the carbocyclic ring which may be partially saturated.

In the present invention, the 3- to 7-membered monocyclic unsaturated heterocycle containing one to three heteroatoms selected from an oxygen atom a nitrogen atom, and a sulfur atom or the heterocycle which may be partially saturated as the ring B or the ring C is preferably a 5- to 7-membered monocyclic unsaturated heterocycle containing one to three heteroatoms selected from an oxygen atom, a nitrogen atom, and a sulfur atom or the heterocycle which may be partially saturated.

In the present invention, $R^{13}$ is preferably (1) a halogen, (2) a hydroxy group, (3) a cyano group, (4) a $C_{1-4}$ alkyl group which may be substituted with a halogen or a hydroxy group (preferably a $C_{1-2}$ alkyl group which may be substituted with a halogen or a hydroxy group), or (5) a $C_{1-4}$ alkoxy group which may be substituted with a halogen or a hydroxy group (preferably a $C_{1-2}$ alkoxy group which may be substituted with a halogen or a hydroxy group), and more preferably (1) a halogen, (2) a hydroxy group, (3) a methyl group which may be substituted with a halogen, or (4) a methoxy group which may be substituted with a halogen.

In the present invention, compounds of the general formula (I) including combinations of the above-listed preferred groups are preferred.

In the present invention, as a preferred compound, a compound represented by the general formula (II):

[Chem. 5]

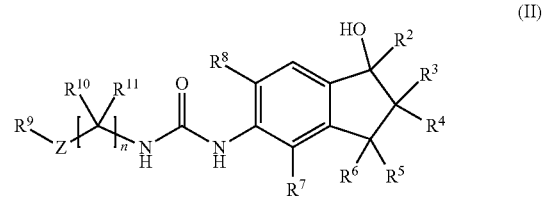

(II)

(wherein the symbols represent the same meanings as described above), or the general formula (III):

[Chem. 6]

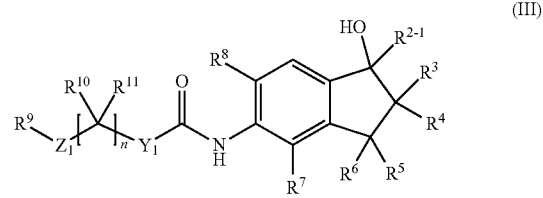

(III)

(wherein $Y_1$ is —NH— or —O—; $Z_1$ is a bond or —O—; $R^{2-1}$ is a hydrogen atom, a methyl group, or a trifluoromethyl group; $R^{9-1}$ is (1) a ring A or (2) -ring B-ring C, where the ring A, the ring B, and the ring C may be each independently substituted with one to five $R^{13}$'s, and when a plurality of $R^{13}$'s is present, the $R^{13}$'s may be the same as or different from one another; and the other symbols represent the same meanings as described above) or a pharmaceutically acceptable salt thereof is exemplified.

In the present invention, as a more preferred compound, a compound represented by the general formula (III-1):

[Chem. 7]

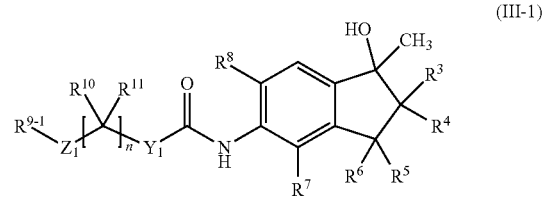

(III-1)

(wherein the symbols represent the same meanings as described above), the general formula (III-2):

[Chem. 8]

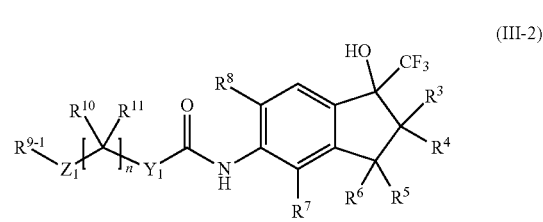

(III-2)

(wherein the symbols represent the same meanings as described above), or the general formula (III-3):

[Chem. 9]

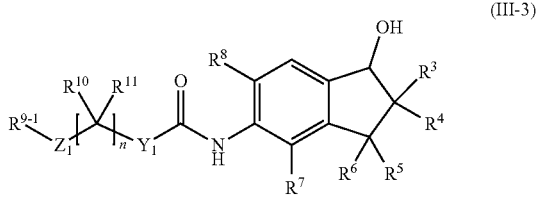

(wherein the symbols represent the same meanings as described above) or a pharmaceutically acceptable salt thereof is exemplified.

The definitions of the above-mentioned preferred groups (single or any combination thereof) are also applied to the general formula (II), the general formula (III), the general formula (III-1), the general formula (III-2), or the general formula (III-3).

In the present invention, a compound of the general formula (II), the general formula (III), the general formula (III-1), the general formula (III-2), or the general formula (III-3) including a combination of the above-listed preferred groups is preferred.

In the present invention, a preferred compound is (1) 1-(4,6-dichloro-1-hydroxy-1-methyl-2,3-dihydro-1H-inden-5-yl)-3-{[5-(trifluoromethyl)-2-pyridinyl]methyl}urea, (2) 1-[4,6-dichloro-1-hydroxy-1-(trifluoromethyl)-2,3-dihydro-1H-inden-5-yl]-3-(4-fluorobenzyl)urea, (3) 1-[4,6-dichloro-1-hydroxy-1-(trifluoromethyl)-2,3-dihydro-1H-inden-5-yl]-3-{[5-(trifluoromethyl)-2-pyridinyl]methyl}urea, (4) 1-[4,6-dichloro-1-hydroxy-1-(trifluoromethyl)-2,3-dihydro-1H-inden-5-yl]-3-[(1R)-1-(4-fluorophenyl)ethyl]urea, or (5) 1-(4,6-dichloro-2,2-difluoro-1-hydroxy-1-methyl-2,3-dihydro-1H-inden-5-yl)-3-(4-fluorobenzyl)urea, a pharmaceutically acceptable salt thereof, a hydrate thereof, or a cocrystal thereof.

In the present invention, more preferred is an optically active substance of the above-mentioned compound, and for example, 1-[(1R)-4,6-dichloro-1-hydroxy-1-(trifluoromethyl)-2,3-dihydro-1H-inden-5-yl]-3-[(1R)-1-(4-fluorophenyl)ethyl]urea or 1-[(1S)-4,6-dichloro-1-hydroxy-1-(trifluoromethyl)-2,3-dihydro-1H-inden-5-yl]-3-[(1R)-1-(4-fluorophenyl)ethyl]urea, a pharmaceutically acceptable salt thereof, a hydrate thereof, or a cocrystal thereof.

A preferred compound of the present invention is a compound having an opening action with respect to KCNQ2/3 in terms of $EC_{50}$ value (or ECrtg50 (see (1) Biological Example 1 described later)) of 100 μM or less, more preferably 10 μM or less, further more preferably 1 μM or less, and particularly preferably 0.1 μM or less. More preferred is a compound having an opening action with respect to all KCNQ2/3, KCNQ4, and KCNQ5 channels (in terms of $EC_{50}$ value (or ECrtg50) for all channels of preferably 100 μM or less, more preferably 10 μM or less, and further more preferably 1 μM or less). A method for determining the $EC_{50}$ value (or ECrtg50) is known to those skilled in the art (see, for example, Neuropharmacology, vol. 40, 2001, pp. 888-898, European Journal of Pharmacology, vol. 437, 2002, pp. 129-137), however, the $EC_{50}$ value is determined preferably by a fluorescence measurement method, and more preferably as described in the part of (1) Biological Example 1 described later.

The compound of the present invention is preferably a compound having excellent solubility. In the present invention, the solubility can be evaluated as a solubility in the Japanese Pharmacopoeia dissolution test second solution (pH: 6.8) by, for example, a dimethyl sulfoxide (DMSO) precipitation method (see, (3) Solubility Test described later). The compound is preferably a compound having a solubility of 20 μM or more, more preferably 40 μM or more, further more preferably 60 μM or more, and particularly preferably 80 μM or more.

The compound of the present invention is preferably a compound having excellent metabolic stability. The metabolic stability can be confirmed by a general measurement method using, for example, liver microsomes of a human or other animal species (preferably, a human). The stability of the compound in human liver microsomes can be evaluated by, for example, reacting commercially available human liver microsomes with the compound of the present invention for a given time (for example, 5 to 30 minutes), and calculating a residual ratio by comparison between a reacted sample and an unreacted sample (see, (4) Evaluation of Stability in Human Liver Microsomes described later).

The compound of the present invention is preferably a compound having excellent safety. For example, the compound of the present invention is a compound in which an action on hERG (human ether-a-go-go related gene) channel is not confirmed, or the hERG channel inhibitory action is weak. The hERG channel inhibitory action (hERG test) can be evaluated by a known method, for example, a rubidium method in which the outflow of rubidium ions (Rb+) is measured in hERG expression cells, a patch clamp test in which an HERG current is measured by a patch clamp method (see, (5) Evaluation of Action on hERG IKr Current described later), or the like.

In the present invention, unless otherwise specified, all stereoisomers are included. For example, geometrical isomers (E-form, Z-form, cis-form, trans-form) of double bonds, rings, and fused rings, optical isomers by the presence of an asymmetric carbon atom (R- and S-forms, α- and β-configurations, enantiomers, and diastereomers), optically active substances having an optical rotation property (D-, L-, d-, and l-forms), polarity isomers (high-polarity and low-polarity isomers) obtained by chromatographic separation, equilibrium compounds, rotamers, mixtures thereof at an arbitrary ratio, and racemic mixtures are all included in the present invention. Further, the present invention also encompasses all isomers due to tautomers.

In the present invention, unless otherwise specified, as is apparent to those skilled in the art, a symbol:
[Chem. 10]

represents binding on the back side of the sheet (that is, an α-configuration), a symbol:
[Chem. 11]

represents binding on the front side of the sheet (that is, a β-configuration), and a symbol:
[Chem. 12]

represents an α-configuration, a β-configuration, or a mixture thereof at an arbitrary ratio.

Further, the optically active compound in the present invention is not limited to a compound having a purity of 100%, but may include other enantiomers or diastereomers having a purity of less than 50%.

The compound represented by the general formula (I) is converted into a corresponding salt by a known method. As the salt, a pharmaceutically acceptable salt is preferred.

Further, the salt is preferably a water-soluble salt. As an appropriate salt, acid addition salts (inorganic acid salts (such as hydrochloride, hydrobromide, hydroiodide, sulfate, phosphate, and nitrate), organic acid salts (such as formate, acetate, propionate, trifluoroacetate, lactate, tartrate, oxalate, malonate, succinate, fumarate, malate, maleate, benzoate, citrate, methanesulfonate, ethanesulfonate, benzenesulfonate, toluenesulfonate, isethionate, glucuronate, gluconate, aspartate, and glutamate), etc.) are exemplified.

The compound represented by the general formula (I) and a salt thereof may be present in an unsolvated form, or in a solvated form with a pharmaceutically acceptable solvent such as water or ethanol. A preferred solvate is a hydrate. The compound represented by the general formula (I) and a salt thereof can be converted into a solvate by a known method.

The compound represented by the general formula (I) and a salt thereof can form a cocrystal with an appropriate cocrystal former. As the cocrystal, a pharmaceutically acceptable cocrystal which is formed with a pharmaceutically acceptable cocrystal former is preferred. The cocrystal is typically defined as a crystal which is formed of two or more different molecules by an intermolecular interaction that is different from an ionic bond. Further, the cocrystal may be a complex of a neutral molecule and a salt. The cocrystal can be prepared by a known method, for example, by melting crystallization, recrystallization from a solvent, or physically pulverizing the components together. The appropriate cocrystal former includes those described in WO 2006/007448.

In the present invention, all the mentions regarding the compound of the present invention include the compound represented by the general formula (I), a salt thereof, a solvate (for example, a hydrate) thereof, or a cocrystal thereof, or a solvate (for example, a hydrate) of a salt of the compound represented by the general formula (I), or a cocrystal thereof.

The compound of the present invention can be administered as a prodrug. For example, a prodrug of the compound represented by the general formula (I) is converted into the compound represented by the general formula (I) by a reaction with an enzyme, gastric acid, or the like, in a living body. Examples of the prodrug of the compound represented by the general formula (I) in the case where the compound represented by the general formula (I) has a hydroxy group include: compounds in which the hydroxy group is acylated, alkylated, phosphorylated, or borated (for example, compounds in which the hydroxy group of the compound of the present invention is acetylated, palmitoylated, propanoylated, pivaloylated, succinylated, fumarylated, alanylated, or dimethylaminomethylcarbonylated, etc.) and the like. These compounds can be produced by a known method. Further, the prodrug of the compound represented by the general formula (I) may be either of a hydrate and a non-hydrate. Further, the prodrug of the compound represented by the general formula (I) may be a compound which is changed into the compound represented by the general formula (I) under a physiological condition as described in "Pharmaceutical Research and Development", vol. 7 "Molecular Design", pp. 163-198, published by Hirokawa Shoten in 1990.

The compound represented by the general formula (I) also includes all isotopes in which at least one atom is replaced by an atom which has the same atomic number, but has a different atomic mass or mass number from the atomic mass or mass number dominant in nature. Examples of the appropriate isotopes included in the compound represented by the general formula (I) include $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$, and the like.

[Method for Producing Compound of the Present Invention]

The compound of the present invention represented by the general formula (I) can be produced using known methods, for example, methods described below, methods equivalent thereto, methods described in Examples, or methods described in "Comprehensive Organic Transformations: A Guide to Functional Group Preparations, 2nd Edition (written by Richard C. Larock, John Wiley & Sons, Inc., 1999)", and the like, which are appropriately modified and combined. Note that in the following respective production methods, each raw material compound may be used as a salt. As such a salt, a salt described as the above-mentioned pharmaceutically acceptable salt of the general formula (I), or the like is used.

The compound of the present invention represented by the general formula (I) can be produced by the method shown in the following reaction scheme 1, 2, 3, or 4 using a compound represented by the general formula (SM1):

[Chem. 13]

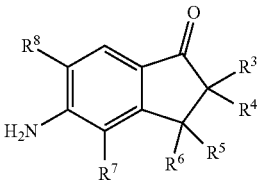

(SM1)

(wherein all symbols represent the same meanings as described above) or the general formula (SM2):

[Chem. 14]

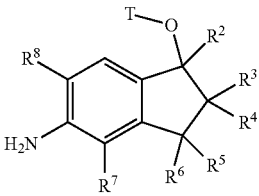

(SM2)

(wherein T represents $R^1$ or a protective group for a hydroxy group, and the other symbols represent the same meanings as described above) as a starting material.

Examples of the protective group for a hydroxy group as T include a methyl group, an ethyl group, a propyl group, a butyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a tert-butyldimethylsilyl (TBDMS) group, a tert-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, a 2,2,2-trichloroethoxycarbonyl (Troc) group, and the like.

The protective group is not particularly limited as long as it is a group which can be easily and selectively detached other than the above-mentioned groups. For example, those described in "Protective Groups in Organic Synthesis (T W. Greene, John Wiley & Sons, Inc., 1999)" are used.

Among the compounds of the present invention represented by the general formula (I), a compound in which Y is —NH— or —O— and $R^1$ is hydrogen, that is, a compound represented by the general formula (1-a):

[Chem. 15]

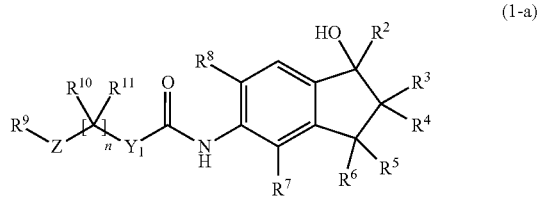

(wherein $Y_1$ represents —NH— or —O—, and the other symbols represent the same meanings as described above) can be produced using a compound represented by the general formula (1-b):

[Chem. 16]

(wherein all symbols represent the same meanings as described above) by a method shown in the reaction scheme 1:

Reaction scheme 1

[Chem. 17]

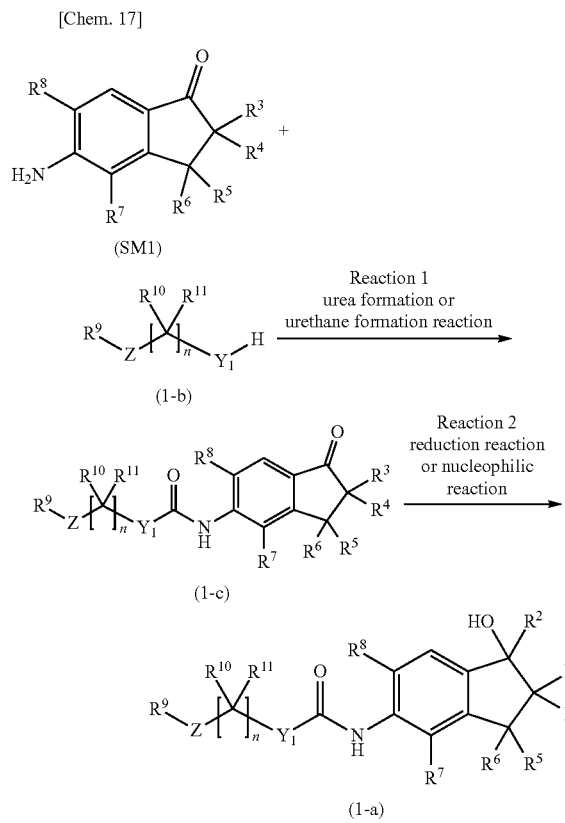

(wherein all symbols represent the same meanings as described above).

The urea formation or urethane formation reaction shown in the reaction 1 in the reaction scheme 1 is carried out, for example, by reacting a compound represented by the general formula (SM1) with triphosgene at room temperature to 40° C. in an organic solvent (tetrahydrofuran, N-methyl-2-pyrrolidinone, N,N-dimethylformamide, dichloromethane, or the like) in the presence of a base (triethylamine, diisopropylethylamine, or the like), thereby forming a corresponding isocyanate, and then reacting with a compound represented by the general formula (1-b) in an organic solvent (tetrahydrofuran, N-methyl-2-pyrrolidinone, dichloromethane, or the like) at a temperature of room temperature to 60° C. in the presence or absence of a base (triethylamine, diisopropylethylamine, or the like). Alternatively, the reaction order of reacting the compound represented by the general formula (SM1) and the compound represented by the general formula (1-b) may be reversed. Further, the urea formation or urethane formation reaction is carried out, for example, by reacting a compound represented by the general formula (SM1) in an organic solvent (dichloromethane or N,N-dimethylformamide) in the presence of 1,1'-carbonylbis-1H-imidazole (CDI), in the presence or absence of a base (triethylamine, N-methyl morpholine, or the like) at a temperature of about 0 to 80° C. It is desired that any of these reactions is carried out in an atmosphere of an inert gas (argon, nitrogen, or the like) under an anhydrous condition.

The reduction reaction shown in the reaction 2 in the reaction scheme 1 is carried out by reacting a compound represented by the general formula (1-c) with a reducing agent (sodium borohydride, lithium borohydride, or the like) in an organic solvent (methanol, ethanol, or the like), or with a reducing agent (lithium aluminum hydride, diisobutylaluminum hydride, or the like) in an organic solvent (tetrahydrofuran, hexane, or the like) at a temperature of −78 to 60° C.

The nucleophilic reaction shown in the reaction 2 in the reaction scheme 1 is carried out by reacting the compound represented by the general formula (1-c) with an organic metal reagent corresponding to $R^2$, for example, alkyl ($R^2$) magnesium bromide, alkyl ($R^2$) magnesium chloride, alkyl ($R^2$) lithium, or the like in an organic solvent (tetrahydrofuran, diethyl ether, or the like) in the presence or absence of cerium chloride at −78° C. to room temperature. Further, the nucleophilic reaction is carried out also by reacting the compound represented by the general formula (1-c) with Ruppert's reagent (trifluoromethyltrimethylsilane) in an organic solvent (tetrahydrofuran, diethyl ether, or the like) in the presence of tetrabutylammonium fluoride at −78° C. to room temperature.

Among the compounds of the present invention represented by the general formula (I), a compound in which Y is —NH— or —O—, that is, a compound represented by the general formula (2-a):

[Chem. 18]

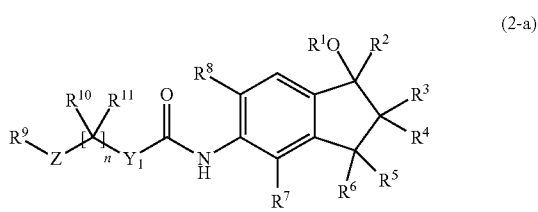

(wherein all symbols represent the same meanings as described above) can be produced by a method shown in the reaction scheme 2:

Reaction scheme 2

[Chem. 19]

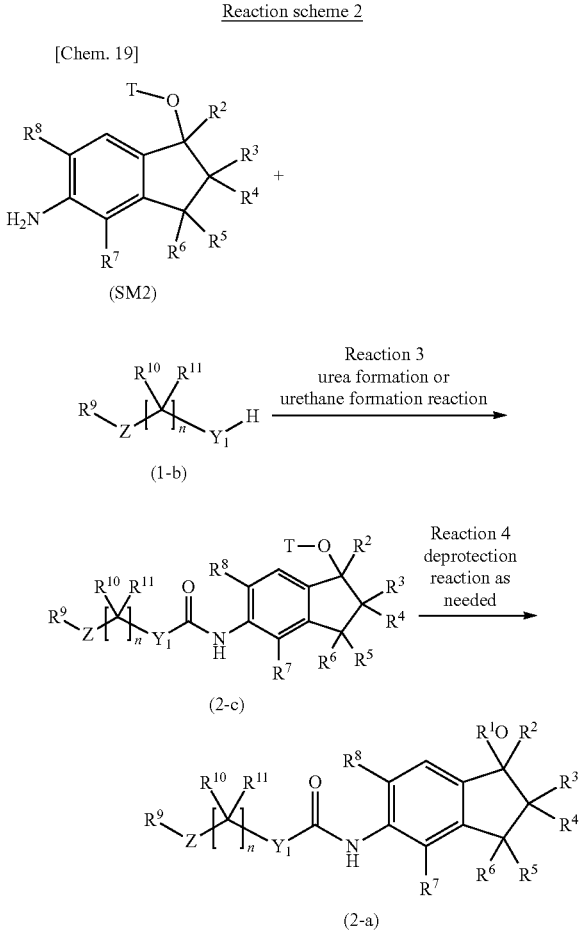

(wherein all symbols represent the same meanings as described above).

The reaction shown in the reaction 3 in the reaction scheme 2 can be carried out in the same manner as the method shown in the reaction 1 in the reaction scheme 1.

In the reaction scheme 2, the deprotection reaction of a hydroxy group shown in the reaction 4 is carried out as needed, and when T is $R^1$ in a compound represented by the general formula (2-c), a compound represented by the general formula (2-a) can be produced without going through the deprotection reaction.

The deprotection reaction of the protective group for a hydroxy group is known and can be carried out by the following methods. Examples thereof include:

(1) a deprotection reaction by alkaline hydrolysis,
(2) a deprotection reaction under an acidic condition,
(3) a deprotection reaction by hydrogenolysis,
(4) a deprotection reaction of a silyl group,
(5) a deprotection reaction using a metal,
(6) a deprotection reaction using a metal complex, and the like.

These methods will be specifically described below.

(1) The deprotection reaction by alkaline hydrolysis is carried out, for example, in an organic solvent (methanol, tetrahydrofuran, dioxide, or the like) using an alkali metal hydroxide (sodium hydroxide, potassium hydroxide, lithium hydroxide, or the like), an alkaline earth metal hydroxide (barium hydroxide, calcium hydroxide, or the like) or an alkaline earth metal carbonate (sodium carbonate, potassium carbonate, or the like), or an aqueous solution thereof or a mixture thereof at a temperature of about 0 to 40° C.

(2) The deprotection reaction under an acidic condition is carried out, for example, in an organic solvent (dichloromethane, chloroform, dioxane, ethyl acetate, anisole, or the like), and in an organic acid (acetic acid, trifluoroacetic acid, methanesulfonic acid, p-toluenesulfonic acid, or the like), or an inorganic acid (hydrochloric acid, sulfuric acid, or the like) or a mixture thereof (hydrogen bromide/acetic acid, or the like) at a temperature of about 0 to 100° C.

(3) The deprotection reaction by hydrogenolysis is carried out, for example, in a solvent (an ether-based solvent (tetrahydrofuran, dioxane, dimethoxyethane, diethyl ether, or the like), an alcohol-based solvent (methanol, ethanol, or the like), a benzene-based solvent (benzene, toluene, or the like), a ketone-based solvent (acetone, methyl ethyl ketone, or the like), a nitrile-based solvent (acetonitrile, or the like), an amide-based solvent (dimethylformamide, or the like), water, ethyl acetate, acetic acid, or a mixed solvent of two or more thereof, or the like) in the presence of a catalyst (palladium-carbon, palladium black, palladium hydroxide, platinum oxide, Raney nickel, or the like) in a hydrogen atmosphere at normal pressure or under pressure, or in the presence of ammonium formate at a temperature of about 0 to 200° C.

(4) The deprotection reaction of a silyl group is carried out, for example, in a water-miscible organic solvent (tetrahydrofuran, acetonitrile, or the like), by using tetrabutylammonium fluoride at a temperature of about 0 to 40° C.

(5) The deprotection reaction using a metal is carried out, for example, in an acidic solvent (acetic acid, a buffer solution at pH 4.2 to 7.2, or a mixed solution of such a solution and an organic solvent such as tetrahydrofuran), in the presence of zinc powder, while applying sonication as needed, at a temperature of about 0 to 40° C.

(6) The deprotection reaction using a metal complex is carried out, for example, in an organic solvent (dichloromethane, dimethylformamide, tetrahydrofuran, ethyl acetate, acetonitrile, dioxane, ethanol, or the like), water or a mixed solvent thereof in the presence of a trap reagent (tributyltin hydride, triethylsilane, dimedone, morpholine, diethylamine, pyrrolidine, or the like), an organic acid (acetic acid, formic acid, 2-ethylhexanic acid, or the like) and/or an organic acid salt (sodium 2-ethylhexanoate, potassium 2-ethylhexanoate, or the like), in the presence or absence of a phosphine-based reagent (triphenylphosphine, or the like) using a metal complex (tetrakis(triphenylphosphine)palladium(0), dichlorobis(triphenylphosphine)palladium(II), palladium(II) acetate, chlorotris(triphenylphosphine)rhodium(I), or the like) at a temperature of about 0 to 40° C.

In addition, other than the above-mentioned methods, the deprotection reaction can be carried out by, for example, the method described in "Protective Groups in Organic Synthesis (written by T W. Greene, John Wiley & Sons, Inc., 1999)".

Although those skilled in the art can easily understand, the objective compound of the present invention can be easily produced by properly using these deprotection reactions.

Among the compounds of the present invention represented by the general formula (I), a compound in which Y is a bond and $R^1$ is hydrogen, that is, a compound represented by the general formula (3-a):

[Chem. 20]

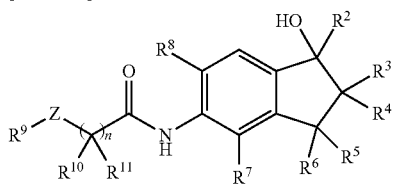

(3-a)

(wherein all symbols represent the same meanings as described above) can be produced using a compound represented by the general formula (3-b):

[Chem. 21]

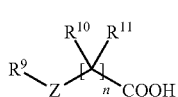

(3-b)

(wherein all symbols represent the same meanings as described above) by a method shown in the reaction scheme 3:

Reaction scheme 3

[Chem. 22]

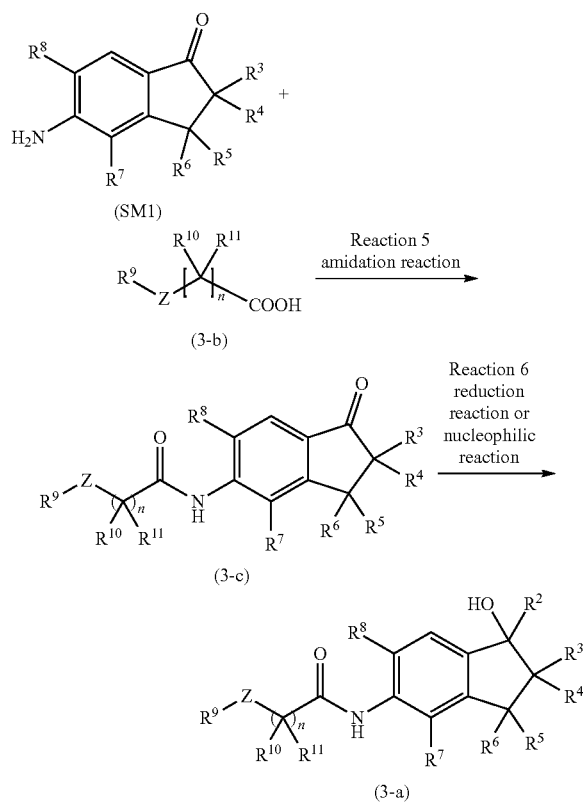

(wherein all symbols represent the same meanings as described above).

That is, the objective compound can be produced by subjecting a compound represented by the general formula (SM1) and a compound represented by the general formula (3-b) to an amidation reaction shown in the reaction 5, and further subjecting the resulting compound to the reduction reaction or the nucleophilic reaction shown in the reaction 6.

The amidation reaction is known, and examples thereof include:

(1) a method using an acid halide,
(2) a method using a mixed acid anhydride,
(3) a method using a condensing agent, and the like.

These methods will be specifically described below.

(1) The method using an acid halide is carried out, for example, by reacting a carboxylic acid with an acid halogenating agent (oxalyl chloride, thionyl chloride, or the like) in an organic solvent (chloroform, dichloromethane, diethyl ether, tetrahydrofuran, or the like) or without solvent at −20° C. to reflux temperature, and then reacting the obtained acid halide with an amine in the presence of a base (pyridine, triethylamine, dimethylaniline, dimethylaminopyridine, diisopropylethylamine, or the like) in an organic solvent (chloroform, dichloromethane, diethyl ether, tetrahydrofuran, or the like) at a temperature of 0 to 40° C. Further, the method can also be carried out by reacting the obtained acid halide with an amine at 0 to 40° C. using an alkaline aqueous solution (an aqueous sodium bicarbonate solution, a sodium hydroxide solution, or the like) in an organic solvent (dioxane, tetrahydrofuran, or the like).

(2) The method using a mixed acid anhydride is carried out, for example, by reacting a carboxylic acid with an acid halide (pivaloyl chloride, tosyl chloride, mesyl chloride, or the like) or an acid derivative (ethyl chloroformate, isobutyl chloroformate, or the like) in an organic solvent (chloroform, dichloromethane, diethyl ether, tetrahydrofuran, or the like) or without solvent in the presence of a base (pyridine, triethylamine, dimethylaniline, dimethylaminopyridine, diisopropylethylamine, or the like) at 0 to 40° C., and then reacting the obtained mixed acid anhydride with an amine in an organic solvent (chloroform, dichloromethane, diethyl ether, tetrahydrofuran, or the like) at 0 to 40° C.

(3) The method using a condensing agent is carried out, for example, by reacting a carboxylic acid with an amine in an organic solvent (chloroform, dichloromethane, dimethyl formamide, diethyl ether, tetrahydrofuran, or the like) or without solvent in the presence or absence of a base (pyridine, triethylamine, dimethylaniline, dimethylaminopyridine, or the like) using a condensing agent (1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, 1-propylphosphonic acid cyclic anhydride (PPA), or the like), and in the presence or absence of 1-hydroxybenzotriazole (HOBt) at 0 to 40° C.

These reactions (1), (2), and (3) are desirably carried out in an atmosphere of an inert gas (argon, nitrogen, or the like) under an anhydrous condition.

The reduction reaction or the nucleophilic reaction shown in the reaction 6 in the reaction scheme 3 can be carried out in the same manner as the reduction reaction or the nucleophilic reaction shown in the reaction 2 in the reaction scheme 1.

Among the compounds of the present invention represented by the general formula (I), a compound in which Y is a bond, that is, a compound represented by the general formula (4-a):

[Chem. 23]

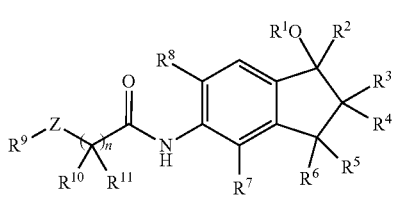

(4-a)

(wherein all symbols represent the same meanings as described above) can be produced by a method shown in the reaction scheme 4:

Reaction scheme 4

[Chem. 24]

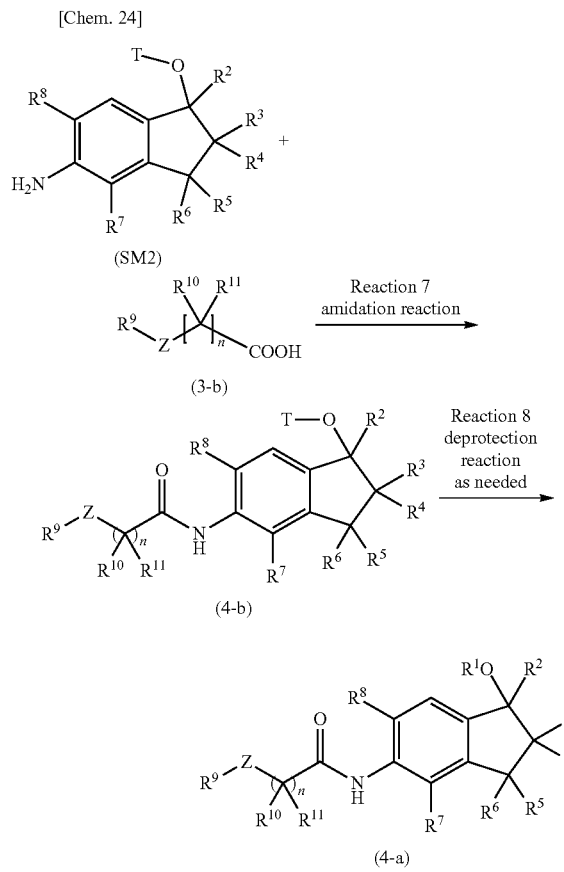

(wherein all symbols represent the same meanings as described above).

The amidation reaction shown in the reaction 7 in the reaction scheme 4 can be carried out in the same manner as the method shown in the reaction 5 in the reaction scheme 3.

Deprotection of a hydroxy group shown in the reaction 8 in the reaction scheme 4 is carried out as needed and can be carried out in the same manner as the method shown in the reaction 4 in the reaction scheme 2, and when T is $R^1$ in a compound represented by the general formula (4-b), a compound represented by the general formula (4-a) can be produced without going through the deprotection reaction.

The compounds represented by the general formulae (SM1) and (SM2) can be produced using a compound represented by the general formula (SM3):

[Chem. 25]

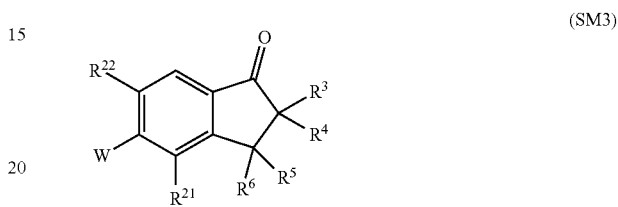

(wherein W represents a halogen (Cl, Br, or I) or a TfO (trifluoromethanesulfonyloxy) group, or a TsO (toluenesulfonyloxy) group, $R^{21}$ and $R^{22}$ represent the same meanings as $R^7$ and $R^8$, respectively (with the proviso that both $R^{21}$ and $R^{22}$ may be simultaneously a hydrogen atom), and the other symbols represent the same meanings as described above) or the general formula (SM4):

[Chem. 26]

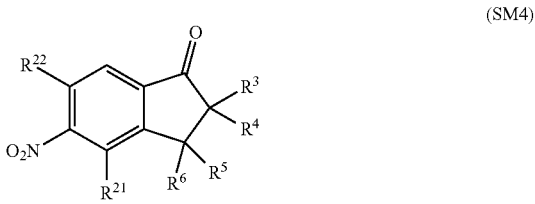

(wherein all symbols represent the same meanings as described above) as a starting material by a method shown in the reaction scheme 5:

Reaction Scheme 5

[Chem. 27]

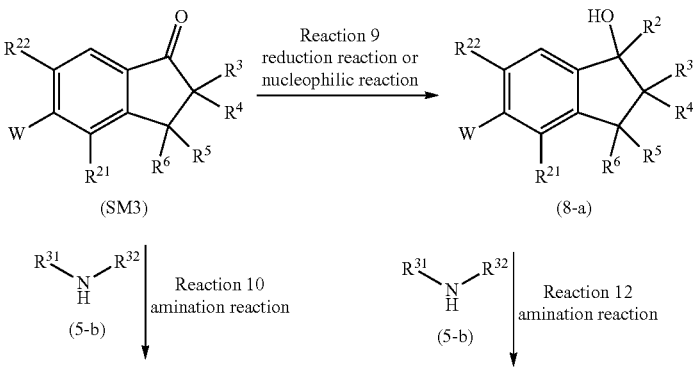

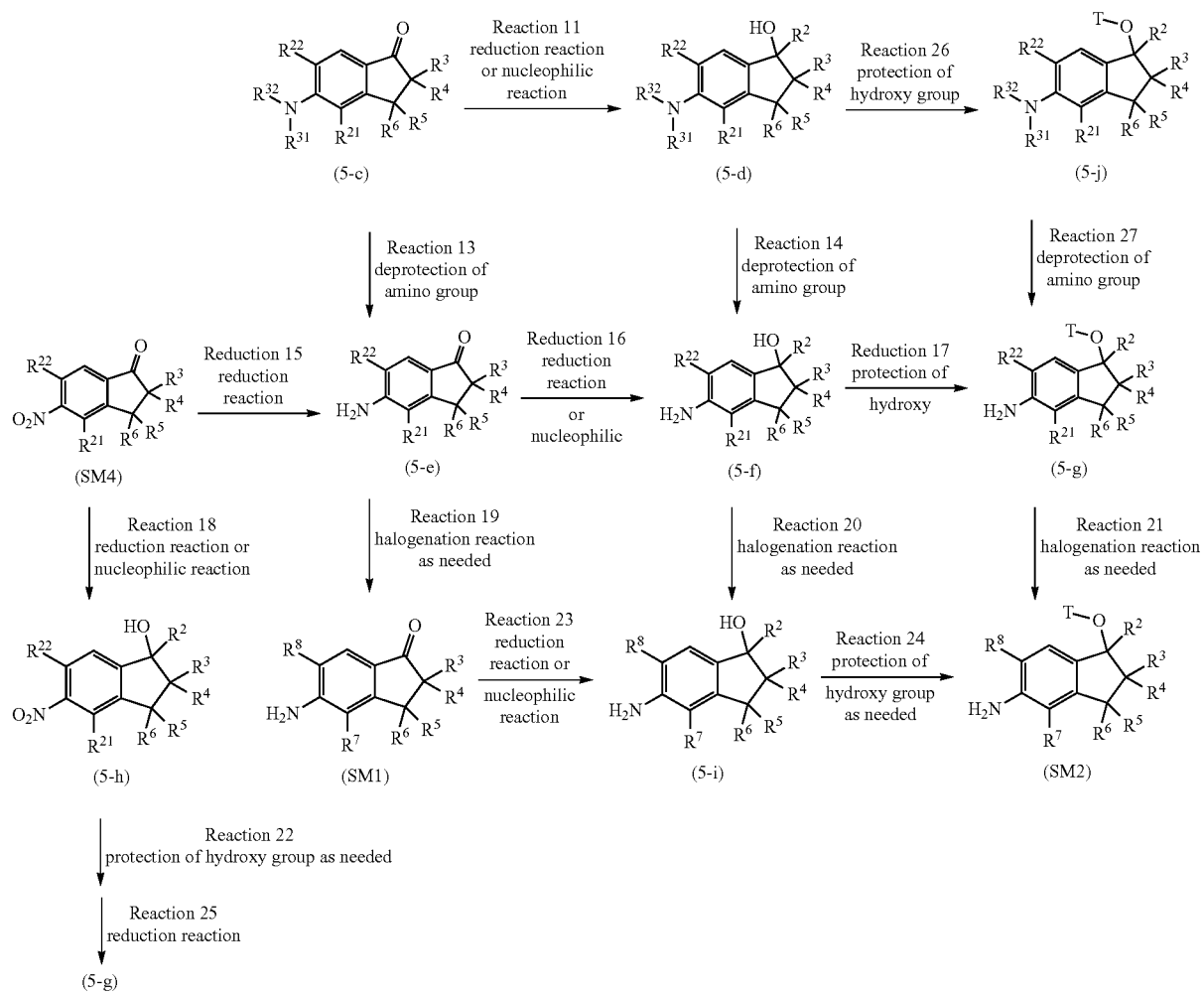

(wherein $R^{31}$ and $R^{32}$ each represent a hydrogen atom or a protective group for an amino group, and the other symbols represent the same meanings as described above).

Example of the protective group for an amino group include a benzyloxycarbonyl group, a t-butoxycarbonyl group, an allyloxycarbonyl (Alloc) group, a 1-methyl-1-(4-biphenyl)ethoxycarbonyl (Bpoc) group, a trifluoroacetyl group, a 9-fluororenylmethoxycarbonyl group, a benzyl (Bn) group, a p-methoxybenzyl group, a benzyloxymethyl (BOM) group, a 2-(trimethylsilyl)ethoxymethyl (SEM) group, and the like.

The compound represented by the general formula (SM3) in which W is a TfO group or a TsO group can be produced from a compound in which W is a hydroxy group by a known method, for example, the method described in "Comprehensive Organic Transformations: A Guide to Functional Group Preparations, second edition (written by Richard C. Larock, John Wiley & Sons, Inc., 1999)" or the like.

The reduction reaction shown in the reaction 9, the reaction 11, the reaction 16, the reaction 18, or the reaction 23 in the reaction scheme 5 can be carried out in the same manner as the reduction reaction shown in the reaction 2 in the reaction scheme 1.

The nucleophilic reaction shown in the reaction 9, the reaction 11, the reaction 16, the reaction 18, or the reaction 23 in the reaction scheme 5 can be carried out in the same manner as the nucleophilic reaction shown in the reaction 2 in the reaction scheme 1.

The amination reaction shown in the reaction 10 or the reaction 12 in the reaction scheme 5 is carried out by reacting a compound represented by the general formula (5-a) or a compound represented by the general formula (SM3) with a compound represented by the general formula (5-b) at room temperature to 120° C. in an organic solvent (ethyl acetate, isopropyl acetate, benzene, toluene, xylene, heptane, cyclohexane, tetrahydrofuran, dioxane, dimethoxyethane, ethanol, isopropanol, polyethylene glycol, dimethyl sulfoxide, N,N-dimethylformamide, N,N-dimethylacetamide. N-methyl-2-pyrrolidinone, methylene chloride, chloroform, acetone, acetonitrile, water, or a mixture thereof, or the like), in the presence of a base (diethylamine, triethylamine, propylamine, diisopropylamine, diisopropylethylamine, dibutylamine, tributylamine, pyrrolidine, piperidine, N-methylpiperidine, 1,4-diazabicyclo[2.2.2]octane (DABCO), pyridine, sodium hydroxide, sodium hydrogen carbonate, sodium carbonate, potassium carbonate, cesium carbonate, sodium phosphate, potassium phosphate, potassium fluoride, or the like), and a catalyst (a palladium catalyst (for example, tetrakis(triphenylphosphine)palladium (Pd(PPh$_3$)$_4$), bis(triphenylphosphine)palladium dichloride (PdCl$_2$(PPh$_3$)$_2$), palladium acetate (Pd(OAc)$_2$), palladium dichloride (PdCl$_2$), palladium black, 1,1'-bis(diphenylphosphinoferrocene)dichloropalladium (PdCl$_2$(dppf)$_2$), diallyl palladium dichloride (PdCl$_2$(allyl)$_2$), phenylbis(triphenylphosphine)palladium iodide (PhPdI(PPh$_3$)$_2$), tris(dibenzylideneacetone)dipalladium (Pd$_2$(DBA)$_3$), bis(tri-tert-butylphosphine)palladium (Pd(tBu$_3$P)$_2$), or the like), and in the presence of a ligand (for example, 4,5-bis(diphenylphosphino)-9,9-dimethylxanthene, or the like). Alternatively, the reaction is carried out by the method shown in Example 24.

The deprotection of an amino group shown in the reaction 13, the reaction 14, or the reaction 27 in the reaction scheme 5 can be carried out by the following methods.

The deprotection reaction of a protective group for an amino group is well known, and examples thereof include
(1) a deprotection reaction by alkaline hydrolysis.
(2) a deprotection reaction under an acidic condition,
(3) a deprotection reaction by hydrogenolysis,
(4) a deprotection reaction of a silyl group,
(5) a deprotection reaction using a metal,
(6) a deprotection reaction using a metal complex, and the like.

These deprotection reactions can be carried out in the same manner as the deprotection of a hydroxy group described above.

Further, the protective group is not particularly limited as long as it is a group which can be easily and selectively detached other than the above-mentioned groups. For example, a group described in "Protective Groups in Organic Synthesis (T. W. Greene, John Wiley & Sons, Inc., 1999)" is used.

In the reaction scheme 5, the protection reaction of a hydroxy group shown in the reaction 17, the reaction 22, the reaction 24, or the reaction 26 is carried out as needed, and the protection reaction is carried out, for example, by reacting the compound represented by the general formula (5-d), the general formula (5-f), the general formula (5-h), or the general formula (5-i) with a silylating agent (chlorotrimethylsilane, chlorotriethylsilane, chloro-tert-butyl dimethylsilane, chloro-tert-butyl diphenylsilane, or the like) in an organic solvent (tetrahydrofuran, dichloromethane, or the like) in the presence of a base (imidazole, triethylamine, or the like) at 0° C. to room temperature.

Further, the protective group is not particularly limited as long as it is a group which can be easily and selectively detached other than the above-mentioned groups. For example, a group described in "Protective Groups in Organic Synthesis (T. W. Greene, John Wiley & Sons, Inc., 1999)" is used.

In the reaction scheme 5, the reduction reaction of a nitro group shown in the reaction 15 or the reaction 25 is carried out by treating a compound represented by the general formula (SM4) or the general formula (5-h) in a solvent (an ether-based solvent (tetrahydrofuran, dioxane, dimethoxyethane, diethyl ether, or the like), an alcohol-based solvent (methanol, ethanol, or the like), a benzene-based solvent (benzene, toluene, or the like), a ketone-based solvent (acetone, methyl ethyl ketone, or the like), a nitrile-based solvent (acetonitrile, or the like), an amide-based solvent (dimethylformamide, or the like), water, ethyl acetate, acetic acid, or a mixed solvent of two or more thereof, or the like) in the presence of a catalyst (palladium-carbon, palladium black, palladium hydroxide, platinum oxide, Raney nickel, or the like) in a hydrogen atmosphere at normal pressure or under pressure, or in the presence of ammonium formate at a temperature of about 0 to 200° C. Alternatively, the reaction is carried out in a water-miscible solvent (ethanol, methanol, tetrahydrofuran, or the like) in the presence or absence of an acid (hydrochloric acid, hydrobromic acid, ammonium chloride, acetic acid, ammonium formate, or the like) using a metal reagent (zinc, iron, tin, tin chloride, iron chloride, samarium, indium, sodium borohydride-nickel chloride, or the like) at a temperature of about 0 to 150° C.

The halogenation shown in the reaction 19, the reaction 20, or the reaction 21 in the reaction scheme 5 is carried out as needed by reacting a compound represented by the general formula (5-e), (5-f), or (5-g) with a halogenation reagent (N-chlorosuccinimide, 1,3-dichloro-5,5-dimethylhydantoin, N-bromosuccinimide, N-iodosuccinimide, or the like) in an organic solvent (acetonitrile, N,N-dimethylformamide, or the like) at 0 to 80° C.

Among the compounds represented by the general formula (SM3) or the general formula (SM4), a compound in which $R^3$, $R^4$, $R^5$, and $R^6$ are not simultaneously a hydrogen atom, that is, a compound represented by the general formula (6-a):

[Chem. 28]

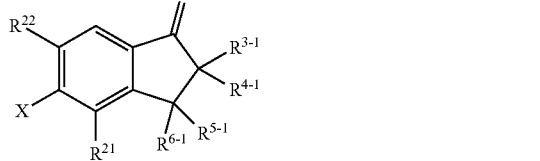

(6-a)

(wherein X represents W or a nitro group, and $R^{3-1}$, $R^{4-1}$, $R^{5-1}$, and $R^{6-1}$ represent the same meanings as $R^3$, $R^4$, $R^5$, and $R^6$, respectively, but are not simultaneously a hydrogen atom, and the other symbols represent the same meanings as described above) can be produced using a compound represented by the general formula (6-b):

[Chem. 29]

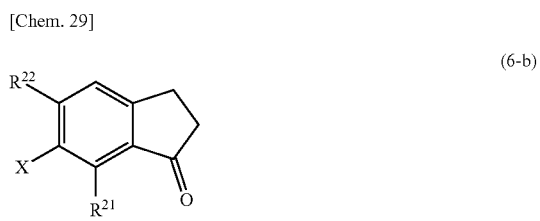

(6-b)

(wherein all symbols represent the same meanings as described above) as a starting material by a method shown in the reaction scheme 6:

Reaction scheme 6

[Chem. 30]

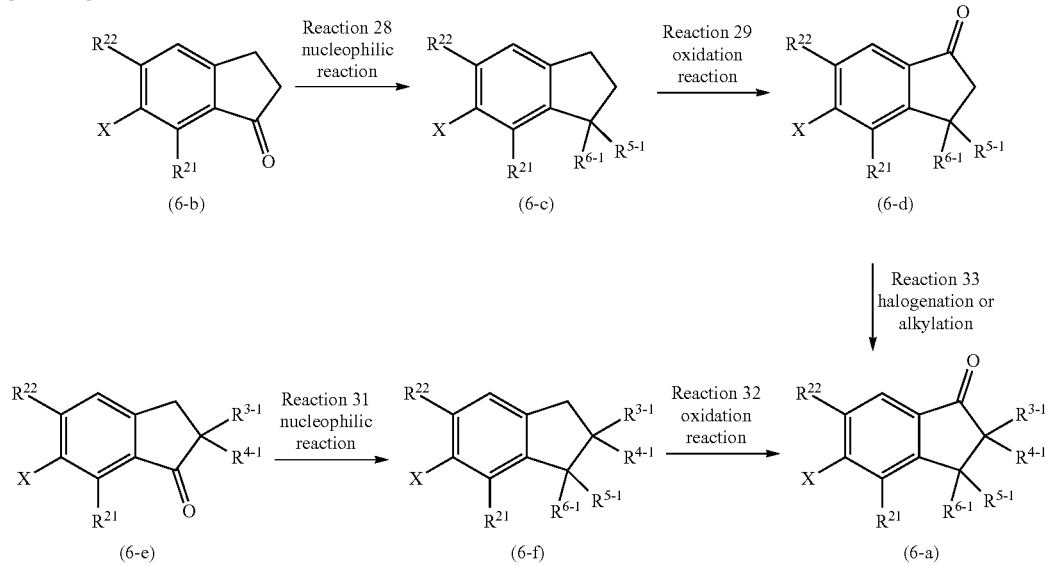

(wherein all symbols represent the same meanings as described above).

The nucleophilic reaction shown in the reaction 28 or the reaction 31 in the reaction scheme 6 is carried out by reacting a compound represented by the general formula (6-b) or the general formula (6-e) with dialkyl zinc in an organic solvent (toluene, hexane, dichloromethane, or the like) in the presence of titanium(IV) chloride or the like at −40° C. to room temperature.

The oxidation reaction shown in the reaction 29 or the reaction 32 in the reaction scheme 6 is carried out by allowing chromium(VI) oxide to act on a compound represented by the general formula (6-c) or the general formula (6-f) in a mixed solvent of acetic acid and water at room temperature to 60° C. Alternatively, the reaction is carried out by reacting a compound represented by the general formula (6-c) or (6-f) with potassium permanganate in an organic solvent (1,2-dichloroethane, dichloromethane, or the like) in the presence of copper sulfate pentahydrate.

The halogenation or alkylation shown in the reaction 30 or the reaction 33 in the reaction scheme 6 is carried out by allowing a base (sodium hydride, lithium diisopropylamide, or the like) and an alkylation reagent (methyl iodide, ethyl iodide, or the like) or a halogenation reagent (N-chlorosuccinimide, N-bromosuccinimide, N-iodosuccinimide, 1,3-dichloro-5,5-dimethylhydantoin, 1,3-dichloro-5,5-dimethylhydantoin, Selectfluor (trade name), N-fluorobenzenesulfonimide, or the like) to act on a compound represented by the general formula (6-b) or the general formula (6-d) in an organic solvent (tetrahydrofuran, diethyl ether, or the like) at −78° C. to room temperature. Alternatively, the halogenation or alkylation is carried out by the method shown in Example 36 and Example 37.

An optically active substance of the compound represented by the general formula (I) can be produced using a starting material having optical activity or a reagent or can be produced by optically resolving a production intermediate in racemic form and converting the resulting intermediate into the compound of the present invention or optically resolving the compound of the present invention in racemic form. The method for optical resolution is known, and the production can be achieved by a conventional method (for example, an optical resolution method using a chiral column or the like).

In each reaction in this specification, a compound to be used as a starting material or a reagent is known per se or can be easily produced by Examples described in this specification or by a known method.

In each reaction in this specification, a reaction involving heating can be carried out using a water bath, an oil bath, a sand bath, or a microwave as is apparent to those skilled in the art.

In each reaction in this specification, a solid-phase supported reagent which is supported on a high-molecular weight polymer (for example, polystyrene, polyacrylamide, polypropylene, polyethylene glycol, or the like) may be used as appropriate.

In each reaction in this specification, the reaction product can be purified by a common purification method, for example, by distillation at normal pressure or reduced pressure, by high performance liquid chromatography using a silica gel or magnesium silicate, thin layer chromatography, an ion-exchange resin, a scavenger resin, or column chromatography, or washing, recrystallization, or the like. The purification may be carried out for each reaction or after completion of several reactions.

[Toxicity]

The compound of the present invention has sufficiently low toxicity, and can be safely used as a pharmaceutical product.

[Application to Pharmaceutical Product]

The compound of the present invention is suitable for preventing and/or treating a KCNQ2-5 channel-related disease.

The compound of the present invention can be used for preventing and/or treating a KCNQ2-5 channel-related disease. Examples of such a disease include epilepsy, pain disorders (for example, neuropathic pain and migraine), diabetic peripheral neuropathy, anxiety disorder, mood adjustment disorder, schizophrenic disorder, drug dependence, attention adjustment disorder, sleep disorder, cerebral stroke, tinnitus, memory impairments (for example, Alzheimer's disease and dementia), amyotrophic lateral sclerosis, movement disorders (for example, movement disorders related to Parkinson's disease or dystonia), dysuria (for example, overactive bladder, frequent urination, nocturia, urinary urgency, urge urinary incontinence, stress urinary incontinence, interstitial cystitis, chronic prostatitis, and prostatic hyperplasia), hearing loss, asthma, chronic obstructive pulmonary disease, coughing, pulmonary hypertension, optic neurodegenerative diseases (for example, glaucoma, progressive diabetic retinopathy, age-related maculopathy, and retinitis pigmentosa), diabetes mellitus, preterm labor • threatened premature delivery, functional dyspepsia, irritable bowel syndrome, and the like.

The compound of the present invention is preferably suitable for preventing and/or treating dysuria.

The compound of the present invention is more preferably suitable for preventing and/or treating overactive bladder.

The overactive bladder is a symptom syndrome which includes urinary urgency as an essential symptom, and is generally accompanied by frequent urination and nocturia, and is sometimes accompanied by urge urinary incontinence.

In the case where the compound of the present invention is used for preventing and/or treating dysuria, in order to avoid central nervous system adverse effects such as dizziness and drowsiness, it is preferred that the intracerebral migration of the compound of the present invention is low. Therefore, the compound of the present invention is preferably a compound showing low intracerebral migration. The intracerebral migration can be evaluated by, for example, an intracerebral content or a calculated intracerebral migration ratio (an intracerebral content/a plasma concentration) obtained by administering a test substance to a mammal (for example, a rat or a mouse) by oral or intravenous administration, and measuring the plasma concentration and/or the intracerebral content after the administration (for example, one hour after the administration).

The compound of the present invention may be administered as a concomitant drug by being combined with another drug for 1) complementing and/or enhancing the prophylactic and/or therapeutic effect, 2) improving the kinetics and absorption and reducing the dose, and/or 3) reducing adverse effects.

The concomitant drug of the compound of the present invention and one or more types of other drugs may be administered in the form of a combination drug in which all the components are combined in a single preparation or may take a form in which the components are formulated into separate preparations and administered. In the case where the components are formulated into separate preparations and administered, simultaneous administration and administration at different times are included. Further, in the case of administration at different times, the compound of the present invention may be first administered, and the other drug may be administered thereafter, or the other drug may be first administered, and the compound of the present invention may be administered thereafter. The respective administration methods may be the same or different.

A disease on which the concomitant drug exhibits a prophylactic and/or therapeutic effect is not particularly limited and may be a disease on which the prophylactic and/or therapeutic effect of the compound of the present invention is complemented and/or enhanced.

Examples of the other drug for complementing and/or enhancing the prophylactic and/or therapeutic effect of the compound of the present invention on overactive bladder include (1) muscarinic receptor antagonists (for example, tolterodine, oxybutynin, hyoscyamine, propantheline, propiverine, trospium, solifenacin, darifenacin, imidafenacin, fesoterodine, temiverine, flavoxate, tarafenacin, afacifenacin, THVD-101, THVD-201), etc.), (2) β3-adrenergic receptor agonists (mirabegron, KRP-114V, solabegron, TRK-380, etc.), (3) NK-1 or -2 antagonists (for example, aprepitant, cizolirtine, etc.), (4) recombinant botulinum toxins (senrebotase, etc.), (5) opioid μ receptor agonists (TRK-130, etc.), (6) α4β2-nicotinic acetylcholine receptor antagonists (dexmecamylamine, etc.), (7) C-fiber inhibitors (besipirdine, etc.), (8) TRPV1 antagonists (XEN-D0501, etc.), (9) EPI antagonists (KEA-0447, etc.), (10) central nervous drugs (REC-1819, etc.), (11) α1-adrenergic receptor antagonists (for example, tamsulosin, silodosin, nafiopidil, urapidil, etc.), (12) 5α-reductase inhibitors (dutasteride, finasteride, etc.), (13) phosphodiesterase-5 inhibitors (sildenafil, tadalafil, and vardenafil), (14) vasopressin V2 receptor agonists (desmopressin), and the like.

The dose of the other drug can be appropriately selected based on the clinically used dose. Further, the mixing ratio of the compound of the present invention to the other drug can be appropriately selected according to the age and body weight of an administration target, an administration method, an administration period, a target disease, symptoms, combination, etc. For example, the other drug may be used in an amount of 0.01 to 100 parts by mass with respect to 1 part by mass of the compound of the present invention. As the other drug, arbitrary two or more drugs may be combined at an appropriate ratio and administered. Further, in the other drug, not only drugs which have been found so far, but also drugs which will be found in future are also included.

In order to use the compound of the present invention or the concomitant drug of the compound of the present invention and the other drug for the above-mentioned purpose, it is generally formulated into an appropriate pharmaceutical composition together with a pharmaceutically acceptable carrier and then administered systemically or topically in the form of an oral or parenteral preparation.

The compound of the present invention is administered to a mammal (preferably, a human, more preferably, a human patient) in a pharmaceutically effective amount.

The dose of the compound of the present invention is dependent on the age, body weight, symptoms, a desired therapeutic effect, an administration route, a treatment period, etc., and therefore inevitably varies. In general, the compound of the present invention is orally administered at a dose ranging from 0.1 mg to 1000 mg once to several times a day per patient, or parenterally administered at a dose ranging from 0.01 mg to 100 mg once to several times a day per patient, or continuously administered intravenously for a period ranging from 1 hour to 24 hours a day.

Of course, as described above, the dose varies depending on various conditions, and therefore, an amount smaller than the above-mentioned dose is sufficient in some cases, or an amount exceeding the range is needed in some cases.

When the compound of the present invention or the concomitant drug of the compound of the present invention and the other drug is administered, it is used as an oral solid preparation or an oral liquid preparation for oral administration, a sustained-release preparation or a controlled-release preparation in oral administration, or an injection, a topical preparation, an inhalant, or a suppository for parenteral administration, or the like.

Examples of the oral solid preparation for oral administration include a tablet, a pill, a capsule, a powder, a granule, and the like. Examples of the capsule include a hard capsule and a soft capsule.

In such an oral solid preparation, one or more active substances are formulated directly or by being mixed with an excipient (for example, lactose, mannitol, glucose, microcrystalline cellulose, starch, or the like), a binder (for example, hydroxypropyl cellulose, polyvinylpyrrolidone, magnesium aluminate metasilicate, or the like), a disintegrating agent (for example, calcium cellulose glycolate, or the like), a lubricant (for example, magnesium stearate, or the like), a stabilizer, a solution adjuvant (for example, glutamic acid, aspartic acid, or the like), or the like according to a conventional method and used. In addition, the oral solid preparation may be coated with a coating agent (for example, white soft sugar, gelatin, hydroxypropyl cellulose, hydroxypropyl methylcellulose phthalate, or the like) and may be coated with two or more layers as needed. Further, the oral solid preparation also includes a capsule of an absorbable substance such as gelatin.

Examples of the oral liquid preparation for oral administration include pharmaceutically acceptable solution, suspension, emulsion, syrup, elixir, and the like. In such a liquid preparation, one or more active substances are dissolved, suspended, or emulsified in a generally used diluent (for example, purified water, ethanol, or a mixed liquid thereof, or the like). Further, this liquid preparation may contain a humectant, a suspending agent, an emulsifying agent, a sweetener, a flavor, an aromatic, a preservative, a buffer, or the like.

Further, the sustained-release preparation in oral administration is also effective. A gel forming substance to be used for such a sustained-release preparation is a substance which is swelled by including a solvent, and the colloidal particles thereof are linked to one another to form a three-dimensional network structure, and can form a jelly-like object losing its fluidity. In the preparation, it is mainly used as a binder, a thickener, and a sustained-release base agent. For example, gum Arabic, agar, polyvinylpyrrolidone, sodium alginate, propylene glycol alginate, carboxyvinyl polymer, carboxymethyl cellulose, carboxymethyl cellulose sodium, guar gum, gelatin, hydroxypropylmethyl cellulose, hydroxypropyl cellulose, polyvinyl alcohol, methyl cellulose, or hydroxyethyl methyl cellulose can be used.

Examples of the injection for parenteral administration include a solution, a suspension, an emulsion, and a solid injection which is used by being dissolved or suspended in a solvent before use. The injection is used by dissolving, suspending, or emulsifying one or more active substances in a solvent. As the solvent, for example, distilled water for injection, physiological saline, a vegetable oil, an alcohol such as propylene glycol, polyethylene glycol, or ethanol, and a combination thereof are used. Further, the injection may contain a stabilizer, a dissolution aid (for example, glutamic acid, aspartic acid. Polysorbate 80 (registered trademark), or the like), a suspending agent, an emulsifying agent, a soothing agent, a buffer, a preservative, or the like. Such an injection is produced by sterilizing at the final step or using an aseptic procedure. Further, it is also possible to use the injection as an aseptic solid preparation (for example, a freeze-dried product is produced and is dissolved in sterilized or sterile distilled water for injection or another solvent before use).

Examples of the dosage form of the external preparation for parenteral administration include a nebulizer, an inhalant, a spray agent, an aerosol agent, an ointment, a gel, a cream, a poultice, a plaster, a liniment, a nasal agent, and the like. Such a preparation contains one or more active substances and is prepared by a known method or according to a commonly used formulation.

The nebulizer, the inhalant, and the spray agent may contain a stabilizer such as sodium hydrogen sulfite, and a buffer which provides isotonicity, for example, an isotonic agent such as sodium chloride, sodium citrate, or citric acid, other than a generally used diluent. The method for producing a spray agent is described in detail in, for example, U.S. Pat. Nos. 2,868,691 and 3,095,355.

The inhalant for parenteral administration includes an aerosol preparation, a powder for inhalation and a liquid for inhalation, and the liquid for inhalation may be in a form in which a preparation is dissolved or suspended in water or another appropriate medium before use.

Such an inhalant is produced according to a known method.

For example, in the case of the liquid for inhalation, it is prepared by appropriately selecting a preservative (for example, benzalkonium chloride, paraben, or the like), a coloring agent, a buffering agent (for example, sodium phosphate, sodium acetate, or the like), an isotonizing agent (for example, sodium chloride, concentrated glycerin, or the like), a thickener (for example, carboxyvinyl polymer or the like), an absorption accelerator, or the like as needed.

In the case of the powder for inhalation, it is prepared by appropriately selecting a lubricant (for example, stearic acid, a salt thereof, or the like), a binder (for example, starch, dextrin, or the like), an excipient (for example, lactose, cellulose, or the like), a coloring agent, a preservative (for example, benzalkonium chloride, paraben, or the like), an absorption accelerator, or the like as needed.

When the liquid for inhalation is administered, a spraying device (for example, an atomizer, a nebulizer, or the like) is generally used, and when the powder for inhalation is administered, an inhalation administration device for a powder agent is generally used.

The ointment is produced according to a known or commonly used formulation. For example, the ointment is prepared by mixing or melting one or more active substances in a base material. The ointment base material is selected from known or commonly used materials. For example, materials selected from higher fatty acids or higher fatty acid esters (for example, adipic acid, myristic acid, palmitic acid, stearic acid, oleic acid, adipate esters, myristate esters, palmitate esters, stearate esters, oleate esters, etc.), waxes (for example, beeswax, spermaceti, ceresin, etc.), surfactants (for example, polyoxyethylene alkyl ether phosphate esters, etc.), higher alcohols (for example, cetanol, stearyl alcohol, cetostearyl alcohol, etc.), silicone oils (for example, dimethylpolysiloxane, etc.), hydrocarbons (for example, hydrophilic petrolatum, white petrolatum, purified lanolin, liquid paraffin, etc.), glycols (for example, ethylene glycol, diethylene glycol, propylene glycol, polyethylene glycol, macrogol, etc.), vegetable oils (for example, castor oil, olive oil, sesame oil, turpentine oil, etc.), animal oils (for example, mink oil, egg yolk oil, squalane, squalene, etc.), water, absorption accelerators, and anti-rash agents are used singly or by mixing two or more thereof. The ointment may further contain a humectant, a preservative, a stabilizer, an antioxidant, an aromatizing agent, or the like.

The gel is produced according to a known or commonly used formulation. For example, the gel is prepared by melting one or more active substances in a base material. The gel base material is selected from known or commonly used materials. For example, materials selected from lower alcohols (for example, ethanol, isopropyl alcohol, etc.), gelling agents (for example, carboxymethyl cellulose, hydroxyethyl cellulose, hydroxypropyl cellulose, ethyl cellulose, etc.), neutralizers (for example, triethanolamine, diisopropanolamine, etc.), surfactants (for example, polyethylene glycol monostearate, etc.), gums, water, absorption accelerators, and anti-rash agents are used singly or by mixing two or more thereof. The gel may further contain a preservative, an antioxidant, an aromatizing agent, or the like.

The cream is produced according to a known or commonly used formulation. For example, the cream is produced by melting or emulsifying one or more active substances in a base material. The cream base material is selected from known or commonly used materials. For example, materials selected from higher fatty acid esters, lower alcohols, hydrocarbons, polyhydric alcohols (for example, propylene glycol, 1,3-butylene glycol, etc.), higher alcohols (for example, 2-hexyldecanol, cetanol, etc.), emulsifying agents (for example, polyoxyethylene alkyl ethers, fatty acid esters, etc.), water, absorption accelerators, and anti-rash agents are used singly or by mixing two or more thereof. The cream may further contain a preservative, an antioxidant, an aromatizing agent, or the like.

The poultice is produced according to a known or commonly used formulation. For example, the poultice is produced by melting one or more active substances in a base material to form a kneaded material, and applying and spreading the kneaded material on a support. The poultice base material is selected from known or commonly used materials. For example, materials selected from thickeners (for example, polyacrylic acid, polyvinylpyrrolidone, gum Arabic, starch, gelatin, methyl cellulose, etc.), humectants (for example, urea, glycerin, propylene glycol, etc.), fillers (for example, kaolin, zinc oxide, talc, calcium, magnesium, etc.), water, dissolution aids, tackifiers, and anti-rash agents are used singly or by mixing two or more thereof. The poultice may further contain a preservative, an antioxidant, an aromatizing agent, or the like.

The plaster is produced according to a known or commonly used formulation. For example, the plaster is produced by melting one or more active substances in a base material, and applying and spreading the resulting material on a support. The plaster base material is selected from known or commonly used materials. For example, materials selected from polymeric base materials, oils and fats, higher fatty acids, tackifiers, and anti-rash agents are used singly or by mixing two or more thereof. The plaster may further contain a preservative, an antioxidant, an aromatizing agent, or the like.

The liniment is produced according to a known or commonly used formulation. For example, the liniment is produced by dissolving, suspending, or emulsifying one or more active substances in a single material or two or more materials selected from water, alcohols (for example, ethanol, polyethylene glycol, etc.), higher fatty acids, glycerin, soaps, emulsifying agents, suspending agents, and the like. The liniment may further contain a preservative, an antioxidant, an aromatizing agent, or the like.

Examples of other compositions for parenteral administration include suppositories for intrarectal administration, pessaries for intravaginal administration, and the like, each of which contains one or more active substances and is formulated according to a conventional method.

The entire contents of all Patent Documents and Non-Patent Documents or Reference Documents explicitly cited in this specification can be incorporated herein by reference as a part of this specification.

EXAMPLES

Hereinafter, the present invention will be described in detail by way of Examples, however, the present invention is not limited thereto.

The solvents in parentheses shown in the part of chromatographic separation and TLC indicate the used elution solvents or development solvents, and the ratio represents a volume ratio.

In the present invention, in silica gel column chromatography, Chromatorex (registered trademark), manufactured by Fuji Silysia Chemical Ltd., Yamazen Hi-Flash column (trade name), or the like was used, and as a purification device, for example, a medium-pressure preparative chromatograph W-prep 2XY (trade name), manufactured by the Yamazen Corporation was used.

Unless otherwise specified, the NMR data is $^1$H-NMR data.

The solvents used in the measurement are indicated in parentheses shown in the part of NMR.

The compound names used in this specification were named using a computer program ACD/Name (registered trademark) of Advanced Chemistry Development, Inc. that generally performs naming according to IUPAC rules or named according to IUPAC nomenclature.

In the present invention, a retention time in an analysis by liquid chromatography (LC) was measured using the following apparatuses under the following conditions.

Analyzer: ACQUITY UPLC I-Class system (manufactured by Waters Corporation)

Detector: UV (PDA), ELSD, MS

Column: YMC Triart C18 (manufactured by YMC Co., Ltd., 1.9 Gm, 2.1 mm×30 mm)

Mobile phase: Liquid A: a 0.1% trifluoroacetic-aqueous acid solution; Liquid B: a 0.1% trifluoroacetic acid-acetonitrile solution Gradient: 0 min (Liquid A/Liquid B=95/5); 0.1 min (Liquid A/Liquid B=95/5); 1.2 min (Liquid A/Liquid B=5/95); 1.4 min (Liquid A/Liquid B=5/95); 1.5 min (Liquid A/Liquid B=95/5)

Flow rate: 1 mL/min, Detection method: 254 nm, Column temperature: 30° C., Injection amount: 2 μL In the present invention, in fractionation by supercritical fluid chromatography (SFC), semi-preparative SFC system (manufactured by Waters Corporation) was used as a purification device. As a column, CHIRALPAK ID (10 mm ID×250 mm, 5 μm, manufactured by DAICEL Co., Ltd.) was used, and optical resolution was carried out under the following fractionation conditions.

Detector: UV (PDA), ELSD, MS

Mobile phase: carbon dioxide/isopropyl alcohol

Flow rate: 30 mL/min or 10 mL/min, Column temperature: 35° C.

Example 1

5-amino-4,6-dichloro-1-indanone

To a N,N-dimethylformamide (60 mL) solution of 5-amino-1-indanone (CAS Registry Number: 3470-54-0) (6.0 g), N-chlorosuccinimide (10.9 g) was added, followed by stirring at room temperature for 2.5 hours. Then, N-chlorosuccinimide (1.0 g) was added thereto, followed by stirring at room temperature for 30 minutes. Under ice-cooling, water (100 mL) was added to the reaction mixture, and the precipitate was collected by filtration. To the obtained precipitate, methanol (200 mL) was added, followed by stirring at room temperature for 30 minutes, and then, the solid was collected by filtration. To the collected solid, hexane/ethyl acetate (90 mL, 1/1) was added, followed by stirring at 70° C. for 1 hour, and then cooling to room temperature and collecting the solid by filtration, whereby the title compound having the following physical properties was obtained (5.0 g).

TLC: Rf 0.71 (hexane:ethyl acetate=1:1):
$^1$H-NMR (CDCl$_3$): δ 2.66-2.70, 3.01-3.05, 5.04, 7.64.

Example 2

1-(4,6-dichloro-1-oxo-2,3-dihydro-1H-inden-5-yl)-3-(4-fluorobenzyl)urea

To a tetrahydrofuran (46 mL) solution of the compound (2.28 g) produced in Example 1, N,N-diisopropylethylamine (2.0 mL) and triphosgene (3.43 g) were added, followed by stirring at 40° C. for 4 hours, and then, the reaction mixture was concentrated under reduced pressure. The resulting residue was dissolved in tetrahydrofuran (46 mL), and 1-(4-fluorophenyl)methanamine (CAS Registry Number: 140-75-0) (2.64 g) was added thereto, followed by stirring at room temperature for 30 minutes. To a mixed solvent of ethyl acetate and hexane containing the reaction mixture, 1 N hydrochloric acid was added, and the precipitate was collected by filtration and sequentially washed with water and a mixed solvent of ethyl acetate and hexane, and then dried at room temperature under reduced pressure, whereby the title compound having the following physical properties was obtained (3.15 g).

TLC: Rf 0.35 (hexane:ethyl acetate=1:1);
$^1$H-NMR (DMSO-d$_6$): δ 2.71-2.75, 3.03-3.07, 4.29, 7.01, 7.14-7.20, 7.33-7.37, 7.70, 8.48.

Example 3

1-(4,6-dichloro-1-hydroxy-1-methyl-2,3-dihydro-1H-inden-5-yl)-3-(4-fluorobenzyl)urea Cerium(III) chloride (4.48 g) was suspended in tetrahydrofuran (35 mL), followed by stirring at room temperature for 3 hours, and then, methyllithium (16.4 mL, a 1.11 M diethyl ether solution) was added thereto at −78° C. over 10 minutes or more. Subsequently, the compound (1.25 g) prepared in Example 2 was added thereto, followed by stirring overnight while gradually increasing the temperature to room temperature. The reaction mixture was poured into an ice-cooled saturated aqueous ammonium chloride solution, and 1 N hydrochloric acid was added thereto to dissolve the insoluble matter, and extraction was performed with ethyl acetate. The organic layer was sequentially washed with water and a saturated aqueous sodium chloride solution, and dried over anhydrous magnesium sulfate, and then concentrated under reduced pressure. The resulting residue was purified by silica gel column chromatography (hexane:ethyl acetate=50:50→0:100), whereby the titled compound having the following physical property values was obtained (1.25 g).

TLC: Rf 0.50 (hexane:ethyl acetate=1:2):
$^1$H-NMR (DMSO-d$_6$): δ 1.41, 2.08-2.12, 2.70-2.95, 4.26, 5.28, 6.78, 7.12-7.18, 7.31-7.36, 8.01.

Examples 3(1) to 3(25)

The titled compounds having the following physical property values were obtained by performing the same procedures as in Example 2 and Example 3 using a corresponding amine or 4-fluorobenzyl alcohol (CAS Registry Number: 459-56-3) in place of 1-(4-fluorophenyl)methanamine.

Example 3(1)

1-(4,6-dichloro-1-hydroxy-1-methyl-2,3-dihydro-1H-inden-5-yl)-3-{[5-(trifluoromethyl)-2-pyridinyl]methyl}urea

[Chem. 31]

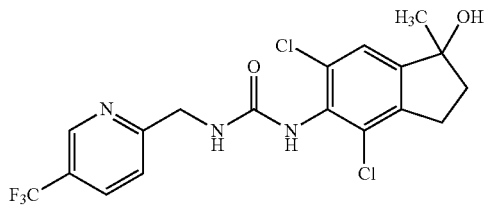

TLC: Rf 0.48 (hexane:ethyl acetate=1:3);
$^1$H-NMR (DMSO-d$_6$): δ 1.41, 2.08-2.12, 2.70-2.95, 4.47, 5.30, 7.04, 7.35, 7.56, 8.24, 8.31, 8.89.

Example 3(2)

1-(4,6-dichloro-1-hydroxy-1-methyl-2,3-dihydro-1H-inden-5-yl)-3-[(1R)-1-(4-fluorophenyl)ethyl]urea TLC: Rf 0.37 (hexane:ethyl acetate=1:2);
$^1$H-NMR (CD$_3$OD): δ 1.48, 2.18-2.23, 2.77-2.87, 2.95-3.05, 4.80-4.93, 7.01-7.07, 7.34, 7.36-7.41.

Example 3(3)

1-benzyl-3-(4,6-dichloro-1-hydroxy-1-methyl-2,3-dihydro-1H-inden-5-yl)urea

TLC: Rf 0.39 (hexane:ethyl acetate=1:1);
$^1$H-NMR (CDCl$_3$): δ 1.58, 1.89, 2.17-2.32, 2.77-2.88, 2.98-3.08, 4.47, 4.82-4.85, 6.01, 7.27-7.36.

Example 3(4)

1-(4,6-dichloro-1-hydroxy-1-methyl-2,3-dihydro-1H-inden-5-yl)-3-[4-(trifluoromethyl)benzyl]urea TLC: Rf 0.31 (hexane:ethyl acetate=1:1);
$^1$H-NMR (DMSO-d$_6$): δ 1.41, 2.08-2.12, 2.70-2.95, 4.37, 5.29, 6.89, 7.34, 7.50-7.53, 7.69-7.71, 8.12.

Example 3(5)

1-(4,6-dichloro-1-hydroxy-1-methyl-2,3-dihydro-1H-inden-5-yl)-3-(4-methylbenzyl)urea TLC: Rf 0.29 (hexane:ethyl acetate=1:1);
$^1$H-NMR (DMSO-d$_6$): δ 1.41, 2.07-2.12, 2.28, 2.72-2.95, 4.23, 5.29, 6.70, 7.11-7.14, 7.18-7.20, 7.34, 7.96.

Example 3(6)

1-(4,6-dichloro-1-hydroxy-1-methyl-2,3-dihydro-1H-inden-5-yl)-3-[4-(trifluoromethoxy)benzyl]urea TLC: Rf 0.29 (hexane:ethyl acetate=1:1);
$^1$H-NMR (DMSO-d$_6$): δ 1.41, 2.07-2.12, 2.70-2.92, 4.30, 5.29, 6.83, 7.32-7.34, 7.40-7.43, 8.07.

Example 3(7)

1-(4,6-dichloro-1-hydroxy-1-methyl-2,3-dihydro-1H-inden-5-yl)-3-[2-(4-fluorophenyl)ethyl]urea TLC: Rf 0.33 (hexane:ethyl acetate=1:2);
$^1$H-NMR (CD$_3$OD): δ 1.50, 2.19-2.24, 2.78-2.88, 2.96-3.06, 3.39-3.43, 6.98-7.04, 7.23-7.28, 7.35.

Example 3(8)

1-(cyclohexylmethyl)-3-(4,6-dichloro-1-hydroxy-1-methyl-2,3-dihydro-1H-inden-5-yl)urea TLC: Rf 0.33 (hexane:ethyl acetate=1:2);
$^1$H-NMR (DMSO-d$_6$): δ 0.83-0.94, 1.13-1.22, 1.40, 1.59-1.70, 2.07-2.12, 2.69-2.93, 5.28, 6.27, 7.32, 7.76.

Example 3(9)

1-(4,6-dichloro-1-hydroxy-1-methyl-2,3-dihydro-1H-inden-5-yl)-3-[3-(trifluoromethyl)benzyl]urea

[Chem. 32]

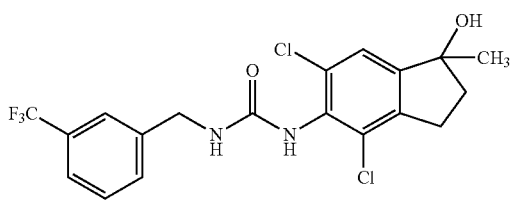

TLC: Rf 0.29 (hexane:ethyl acetate=1:1);
$^1$H-NMR (DMSO-d$_6$): δ 1.41, 2.07-2.12, 2.70-2.95, 4.36, 5.29, 6.91, 7.34, 7.52-7.61, 7.67, 8.15.

Example 3(10)

1-(4,6-dichloro-1-hydroxy-1-methyl-2,3-dihydro-1H-inden-5-yl)-3-[2-(4-fluorophenyl)-2-propanyl]urea

[Chem. 33]

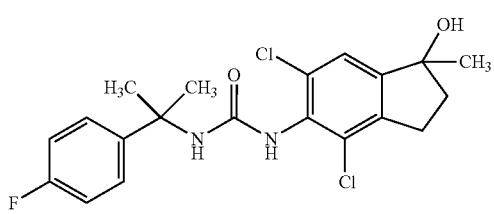

TLC: Rf 0.49 (hexane:ethyl acetate=1:2);
$^1$H-NMR (DMSO-d$_6$): δ 1.38, 1.57, 2.05-2.10, 2.69-2.90, 5.26, 6.78, 7.06-7.12, 7.29, 7.40-7.45, 7.78.

Example 3(11)

1-(4,6-dichloro-1-hydroxy-1-methyl-2,3-dihydro-1H-inden-5-yl)-3-(2-fluorobenzyl)urea TLC: Rf 0.21 (hexane:acetone=3:2);
$^1$H-NMR (DMSO-d$_6$): δ 1.41, 2.07-2.12, 2.70-2.95, 4.31-4.33, 5.29, 6.75-6.79, 7.13-7.42, 8.07.

Example 3(12)

1-(cyclopentylmethyl)-3-(4,6-dichloro-1-hydroxy-1-methyl-2,3-dihydro-1H-inden-5-yl)urea TLC: Rf 0.29 (hexane:ethyl acetate=1:1);
$^1$H-NMR (DMSO-d$_6$): δ 1.15-1.26, 1.41, 1.45-1.72, 1.94-2.04, 2.07-2.12, 2.69-2.92, 2.97-3.01, 5.27, 6.29, 7.32, 7.77.

Example 3(13)

1-(2-cyclopentylethyl)-3-(4,6-dichloro-1-hydroxy-1-methyl-2,3-dihydro-1H-inden-5-yl)urea

[Chem. 34]

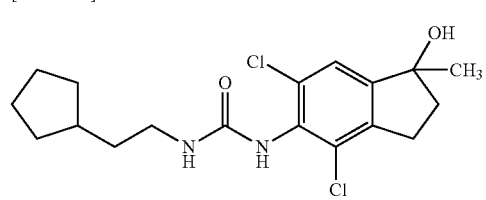

TLC: Rf 0.29 (hexane:ethyl acetate=1:2);
$^1$H-NMR (DMSO-d$_6$): δ 1.01-1.14, 1.41-1.60, 1.70-1.82, 2.07-2.12, 2.71-2.94, 3.03-3.09, 5.28, 6.22, 7.31, 7.79.

Example 3(14)

1-(4,6-dichloro-1-hydroxy-1-methyl-2,3-dihydro-1H-inden-5-yl)-3-(2,4-difluorobenzyl)urea TLC: Rf 0.30 (hexane:ethyl acetate=1:1);
$^1$H-NMR (DMSO-d$_6$): δ 1.41, 2.07-2.12, 2.69-2.94, 4.28, 5.29, 6.79, 7.06-7.12, 7.17-7.25, 7.33, 7.38-7.46, 8.08.

Example 3(15)

1-(4,6-dichloro-1-hydroxy-1-methyl-2,3-dihydro-1H-inden-5-yl)-3-[2-fluoro-4-(trifluoromethyl)benzyl]urea TLC: Rf 0.30 (hexane:ethyl acetate=1:1);
$^1$H-NMR (DMSO-d$_6$): δ 1.41, 2.08-2.12, 2.70-2.95, 4.38, 5.29, 6.89, 7.34, 7.57-7.65, 8.19.

Example 3(16)

1-(4,6-dichloro-1-hydroxy-1-methyl-2,3-dihydro-1H-inden-5-yl)-3-[2-fluoro-4-(trifluoromethoxy)benzyl]urea

[Chem. 35]

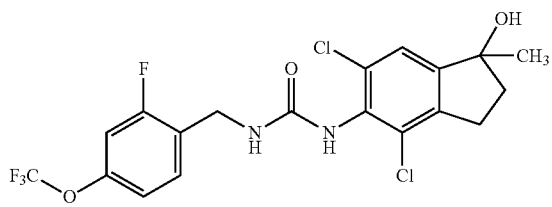

TLC: Rf 0.38 (hexane:ethyl acetate=1:1);
$^1$H-NMR (DMSO-$d_6$): δ 1.41, 2.08-2.12, 2.70-2.95, 4.32, 5.29, 6.84, 7.25-7.28, 7.34, 7.48-7.53, 8.13.

Example 3(17)

1-(4,6-dichloro-1-hydroxy-1-methyl-2,3-dihydro-1H-inden-5-yl)-3-[(4,4-difluorocyclohexyl)methyl]urea TLC: Rf 0.38 (hexane:ethyl acetate=1:1);
$^1$H-NMR (DMSO-$d_6$): δ 1.12-1.25, 1.41, 1.48-2.12, 2.69-2.94, 2.97-3.01, 5.28, 6.36, 7.32, 7.82.

Example 3(18)

1-(4,6-dichloro-1-hydroxy-1-methyl-2,3-dihydro-1H-inden-5-yl)-3-{[4-(trifluoromethoxy)-2-pyridinyl]methyl}urea TLC: Rf 0.20 (hexane:ethyl acetate=1:2);
$^1$H-NMR (DMSO-$d_6$): δ 1.41, 2.07-2.12, 2.70-2.95, 4.46, 5.30, 7.04-7.08, 7.35, 7.63-7.67, 8.36, 8.79.

Example 3(19)

4-fluorobenzyl(4,6-dichloro-1-hydroxy-1-methyl-2,3-dihydro-1H-inden-5-yl)carbamate

[Chem. 36]

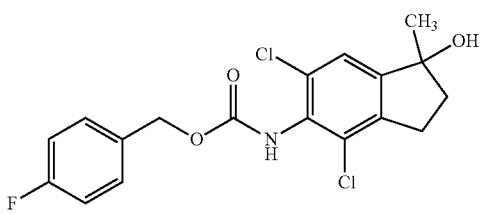

TLC: Rf 0.23 (hexane:ethyl acetate=3:1);
$^1$H-NMR (CDCl$_3$): δ 1.56, 1.84, 2.17-2.33, 2.78-2.89, 2.99-3.09, 5.18, 6.31, 7.02-7.08, 7.35, 7.36-7.40.

Example 3(20)

1-(4,6-dichloro-1-hydroxy-1-methyl-2,3-dihydro-1H-inden-5-yl)-3-{(1R)-1-[4-(trifluoromethyl)phenyl]ethyl}urea TLC: Rf 0.59 (hexane:ethyl acetate=1:2);
$^1$H-NMR (DMSO-$d_6$): δ 1.39, 1.40, 2.06-2.11, 2.68-2.79, 2.83-2.92, 4.81-4.90, 5.28, 6.94, 7.31, 7.55-7.58, 7.69-7.71, 7.87.

Example 3(21)

1-(cycloheptylmethyl)-3-(4,6-dichloro-1-hydroxy-1-methyl-2,3-dihydro-1H-inden-5-yl)urea TLC: Rf 0.43 (hexane:ethyl acetate=1:1);
$^1$H-NMR (DMSO-$d_6$): δ 1.09-1.20, 1.32-1.74, 2.07-2.12, 2.69-2.94, 5.28, 6.30, 7.31, 7.77.

Example 3(22)

1-(2-cyclohexylethyl)-3-(4,6-dichloro-1-hydroxy-1-methyl-2,3-dihydro-1H-inden-5-yl)urea TLC: Rf 0.43 (hexane:ethyl acetate=1:1);
$^1$H-NMR (DMSO-$d_6$): δ 0.81-0.93, 1.09-1.33, 1.40, 1.64-1.72, 2.07-2.12, 2.69-2.79, 2.84-2.94, 3.05-3.11, 5.28, 6.19, 7.32, 7.78.

Example 3(23)

1-(4,6-dichloro-1-hydroxy-1-methyl-2,3-dihydro-1H-inden-5-yl)-3-[2-(4-fluorophenoxy)ethyl]urea TLC: Rf 0.48 (hexane:ethyl acetate=1:2);
$^1$H-NMR (CDCl$_3$): δ 1.61, 2.18-2.32, 2.76-2.86, 2.96-3.06, 3.61-3.66, 4.00-4.04, 5.14, 6.25, 6.78-6.83, 6.93-6.99, 7.33.

Example 3(24)

1-[2-(cyclohexyloxy)ethyl]-3-(4,6-dichloro-1-hydroxy-1-methyl-2,3-dihydro-1H-inden-5-yl)urea

[Chem. 37]

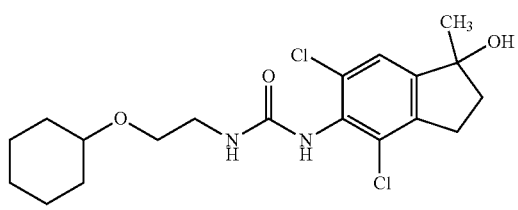

TLC: Rf 0.41 (hexane:ethyl acetate=1:2);
$^1$H-NMR (CDCl$_3$): δ 1.13-1.31, 1.63, 1.68-1.88, 2.06, 2.18-2.33, 2.77-2.88, 2.98-3.07, 3.21-3.28, 3.40-3.44, 3.53-3.56, 5.06, 6.38, 7.34.

Example 3(25)

1-(bicyclo[2.2.1]hept-2-ylmethyl)-3-(4,6-dichloro-1-hydroxy-1-methyl-2,3-dihydro-1H-inden-5-yl)urea

[Chem. 38]

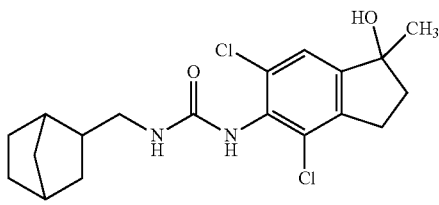

TLC: Rf 0.57 (hexane:ethyl acetate=1:2);
$^1$H-NMR (DMSO-d$_6$): δ 0.61-0.66, 1.02-1.70, 1.90-2.27, 2.69-2.98, 3.09-3.16, 5.28, 6.21, 6.31, 7.32, 7.75, 7.77.

Example 4(1)

1-(4,6-dichloro-1-hydroxy-1-methyl-2,3-dihydro-1H-inden-5-yl)-3-(4-fluorobenzyl)urea (First Peak)

Example 4(2)

1-(4,6-dichloro-1-hydroxy-1-methyl-2,3-dihydro-1H-inden-5-yl)-3-(4-fluorobenzyl)urea (Second Peak)

The compound (50 mg) produced in Example 3 was subjected to optical resolution by supercritical fluid chromatography (carbon dioxide:isopropyl alcohol=70:30, flow rate: 30 mL/min), whereby the title compounds having the following physical property values were obtained (Example 4(1): 10.8 mg, Example 4(2): 11.4 mg).

Example 4(1)

SFC retention time: 5.13 min
TLC: Rf 0.30 (hexane:ethyl acetate=2:3);
$^1$H-NMR (CDCl$_3$): δ 1.57, 1.88, 2.15-2.33, 2.78-2.88, 2.98-3.08, 4.42, 4.86, 6.04, 6.97-7.03, 7.29-7.31, 7.35.

Example 4(2)

SFC retention time: 6.42 min
TLC: Rf 0.30 (hexane:ethyl acetate=2:3);
$^1$H-NMR (CDCl$_3$): δ 1.57, 1.90, 2.15-2.33, 2.78-2.88, 2.98-3.08, 4.42, 4.87, 6.05, 6.97-7.03, 7.28-7.30, 7.34.

Example 4(3)

1-(4,6-dichloro-1-hydroxy-1-methyl-2,3-dihydro-1H-inden-5-yl)-3-{[5-(trifluoromethyl)-2-pyridinyl]methyl}urea (First Peak)

Example 4(4)

1-(4,6-dichloro-1-hydroxy-1-methyl-2,3-dihydro-1H-inden-5-yl)-3-{[5-(trifluoromethyl)-2-pyridinyl]methyl}urea (Second Peak)

The compound (32 mg) produced in Example 3(1) was subjected to optical resolution by supercritical fluid chromatography (carbon dioxide:isopropyl alcohol=70:30, flow rate: 30 mL/min), whereby the title compounds having the following physical property values were obtained (Example 4(3): 13.8 mg, Example 4(4): 13.4 mg).

Example 4(3)

SFC retention time: 3.82 min
TLC: Rf 0.48 (hexane:ethyl acetate=1:3);
$^1$H-NMR (DMSO-d$_6$): δ 1.41, 2.07-2.12, 2.70-2.95, 4.47, 5.28, 7.02, 7.35, 7.59, 8.24, 8.29, 8.90.

Example 4(4)

SFC retention time: 6.53 min
TLC: Rf 0.48 (hexane:ethyl acetate=1:3);
$^1$H-NMR (DMSO-d$_6$): δ 1.41, 2.08-2.12, 2.70-2.95, 4.47, 5.29, 7.03, 7.35, 7.59, 8.24, 8.30, 8.90.

Example 4(5)

1-(4,6-dichloro-1-hydroxy-1-methyl-2,3-dihydro-1H-inden-5-yl)-3-[(1R)-1-(4-fluorophenyl)ethyl]urea (First Peak)

Example 4(6)

1-(4,6-dichloro-1-hydroxy-1-methyl-2,3-dihydro-1H-inden-5-yl)-3-[(1R)-1-(4-fluorophenyl)ethyl]urea (Second Peak)

The compound (30 mg) produced in Example 3(2) was subjected to optical resolution by supercritical fluid chromatography (carbon dioxide:isopropyl alcohol=70:30, flow rate: 30 mL/min), whereby the title compounds having the following physical property values were obtained (Example 4(5): 6.3 mg, Example 4(6): 5.8 mg).

Example 4(5)

SFC retention time: 3.02 min
TLC: Rf 0.39 (hexane:ethyl acetate=1:2);
$^1$H-NMR (CDCl$_3$): δ 1.46, 1.61, 2.02, 2.18-2.30, 2.77-2.85, 2.96-3.05, 4.94-4.99, 6.10, 6.96-7.03, 7.28-7.33.

Example 4(6)

SFC retention time: 5.99 min
TLC: Rf 0.40 (hexane:ethyl acetate=1:1);
$^1$H-NMR (CDCl$_3$): δ 1.46, 1.61, 2.02, 2.18-2.30, 2.75-2.85, 2.96-3.06, 4.93-4.99, 6.09, 6.97-7.03, 7.29-7.32.

Example 5

2-methyl-2-propanyl (1-oxo-2,3-dihydro-1H-inden-5-yl)carbamate

5-Amino-1-indanone (CAS registry number: 3470-54-0) (5.00 g) was suspended in toluene (50 mL), and bis(2-methyl-2-propanyl)carbonate (16.31 g) (CAS Registry Number: 34619-03-9) was added thereto, followed by stirring at 90° C. for 14 hours. To the reaction mixture, bis(2-methyl-2-propanyl)carbonate (16.31 g) was added, followed by stirring at 90° C. for 10 hours. The reaction mixture was concentrated under reduced pressure, and hexane was added to the resulting residue, and then, the solid was collected by filtration, whereby the title compound having the following physical property values was obtained (7.45 g).

TLC: Rf 0.76 (hexane:ethyl acetate=1:1);
$^1$H-NMR (CDCl$_3$): δ 1.54, 2.65-2.66, 3.08-3.11, 6.73, 7.10-7.13, 7.66-7.69, 7.75.

Example 6 bis(2-methyl-2-propanyl)(1-oxo-2,3-dihydro-1H-inden-5-yl)imidodicarbonate

To a dichloromethane (50 mL) solution of the compound (5.00 g) produced in Example 5, bis(2-methyl-2-propanyl) carbonate (6.62 g) and N,N-dimethyl-4-pyridinamine (240 mg) (CAS Registry Number: 1122-58-3) were added, followed by stirring at room temperature for 30 minutes. The reaction mixture was purified by silica gel column chromatography (hexane:ethyl acetate=87:13→66:34→30:70), whereby the title compound having the following physical property values was obtained (5.79 g).

TLC: Rf 0.73 (hexane:ethyl acetate=4:1);
$^1$H-NMR (CDCl$_3$): δ 1.45, 2.71-2.74, 3.14-3.18, 7.14-7.18, 7.26-7.29, 7.74-7.77.

Example 7 bis(2-methyl-2-propanyl)[1-hydroxy-1-(trifluoromethyl)-2,3-dihydro-1H-inden-5-yl]imidodicarbonate To a tetrahydrofuran (40 mL) solution of the compound (3.90 g) produced in Example 6 and trimethyl(trifluoromethyl)silane (4.8 mL) (CAS Registry Number: 81290-20-2), tetrabutylammonium fluoride (0.56 mL, a 1 M tetrahydrofuran solution) was added under ice-cooling, followed by stirring at room temperature for 7 hours. The reaction mixture was diluted with a saturated aqueous ammonium chloride solution, and extraction was performed with ethyl acetate. The organic layer was dried over anhydrous sodium sulfate, and concentrated under reduced pressure. The resulting residue was dissolved in tetrahydrofuran (40 mL), and tetrabutylammonium fluoride (13 mL, a 1 M tetrahydrofuran solution) was added thereto under ice-cooling, followed by stirring for 10 minutes under ice-cooling. The reaction mixture was concentrated under reduced pressure, and the resulting residue was purified by silica gel column chromatography (hexane:ethyl acetate=90:10-50:50), whereby the title compound having the following physical property values was obtained (4.32 g).

TLC: Rf 0.70 (hexane:ethyl acetate=5:1);
$^1$H-NMR (CDCl$_3$): δ 1.45, 2.24-2.31, 2.41, 2.63-2.73, 2.94-3.15, 7.07-7.10, 7.47-7.50.

Example 8

5-amino-1-(trifluoromethyl)-1-indanol

To a dichloromethane (40 mL) solution of the compound (4.32 g) produced in Example 7, trifluoroacetic acid (10 mL) was added under ice-cooling, followed by stirring at room temperature for 5 hours. The reaction mixture was concentrated under reduced pressure, and the resulting residue was diluted with a saturated aqueous sodium hydrogen carbonate solution, and extraction was performed with ethyl acetate. The organic layer was dried over anhydrous sodium sulfate, and concentrated under reduced pressure. The resulting residue was purified by silica gel column chromatography (hexane:ethyl acetate=70:30→50:50), whereby the title compound having the following physical property values was obtained (1.11 g).

TLC: Rf 0.48 (hexane:ethyl acetate=1:1);
$^1$H-NMR (CDCl$_3$): δ 2.15-2.23, 2.30, 2.57-2.66, 2.83-3.07, 3.78, 6.57-6.60, 7.25-7.27.

Example 9

5-amino-4,6-dichloro-1-(trifluoromethyl)-1-indanol

To a N,N-dimethylformamide (20 mL) solution of the compound (1.00 g) produced in Example 8, N-chlorosuccinimide (1.40 g) was added, followed by stirring at room temperature for 4 hours, and then stirring at 50° C. for 1 hour. The reaction mixture was diluted with water, and extraction was performed with ethyl acetate. The organic layer was washed with water, and dried over anhydrous sodium sulfate, and then concentrated under reduced pressure. The resulting residue was purified by silica gel column chromatography (hexane:ethyl acetate=80:20→50:50), whereby the title compound having the following physical property values was obtained (794 mg).

TLC: Rf 0.48 (hexane:ethyl acetate=2:1);
$^1$H-NMR (CDCl$_3$): δ 2.18-2.28, 2.34, 2.61-2.71, 2.89-3.13, 4.60, 7.32.

Example 10

4,6-dichloro-1-(trifluoromethyl)-1-[(trimethylsilyl)oxy]-5-indanamine

To a tetrahydrofuran (1 mL) solution of the compound (50 mg) produced in Example 9, imidazole (13 mg) and chlorotrimethylsilane (25 μL) were added, followed by stirring at room temperature for 1.5 hours. To the reaction mixture, imidazole (13 mg) and chlorotrimethylsilane (24 μL) were added, followed by stirring at room temperature for 3.5 hours, and then, imidazole (26 mg) and chlorotrimethylsilane (50 μL) were added thereto, followed by stirring at room temperature for 40 minutes. The reaction mixture was diluted with water, and extraction was performed with ethyl acetate. The organic layer was dried over anhydrous sodium sulfate, and concentrated under reduced pressure. The resulting residue was purified by silica gel column chromatography (hexane:ethyl acetate=100:0→70:30), whereby the title compound having the following physical property values was obtained (25 mg).

TLC: Rf 0.88 (hexane:ethyl acetate=2:1);
$^1$H-NMR (CDCl$_3$): δ 0.01, 2.16-2.26, 2.57-2.67, 2.84-3.05, 4.56, 7.27.

Example 11

1-{4,6-dichloro-1-(trifluoromethyl)-1-[(trimethylsilyl)oxy]-2,3-dihydro-1H-inden-5-yl}-3-(4-fluorobenzyl)urea To a tetrahydrofuran (1 mL) solution of the compound (25 mg) produced in Example 10, N,N-diisopropylethylamine (13 μL) and triphosgene (23 mg) were added, followed by stirring at room temperature for 30 minutes, and then, the reaction mixture was concentrated under reduced pressure. The resulting residue was dissolved in tetrahydrofuran (1 mL), and 1-(4-fluorophenyl)methanamine (CAS Registry Number: 140-75-0) (17 mg) was added thereto under ice-cooling, followed by stirring at room temperature for 12 hours. The reaction mixture was diluted with water, and the organic layer extracted with ethyl acetate was dried over anhydrous sodium sulfate, and then concentrated under reduced pressure. The resulting residue was purified by silica gel column chromatography (hexane:ethyl acetate=90:10→60:40), whereby the title compound having the following physical property values was obtained (18 mg).

TLC: Rf 0.58 (hexane:ethyl acetate=2:1);

$^1$H-NMR (CDCl$_3$): δ 0.06, 2.23-2.33, 2.65-2.74, 2.90-3.11, 4.44, 4.90, 6.08, 6.99-7.04, 7.27-7.32, 7.47.

Example 12

1-[4,6-dichloro-1-hydroxy-1-(trifluoromethyl)-2,3-dihydro-1H-inden-5-yl]-3-(4-fluorobenzyl)urea

[Chem. 39]

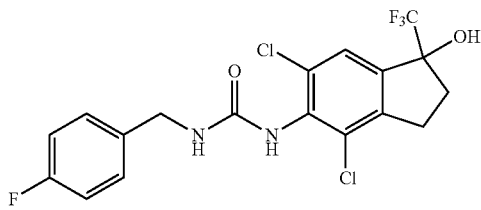

To a mixed solution of dichloromethane (1 mL) and methanol (1 mL) containing the compound (18 mg) produced in Example 11, trifluoroacetic acid (0.5 mL) was added, followed by stirring at room temperature for 4 hours. The reaction mixture was concentrated under reduced pressure, and the resulting residue was purified by silica gel column chromatography (hexane:ethyl acetate=70:30-40:60), whereby the title compound having the following physical property values was obtained (13 mg).

TLC: Rf 0.42 (hexane:ethyl acetate=2:1);

$^1$H-NMR (CDCl$_3$): δ 2.21-2.31, 2.66-2.75, 2.82, 2.93-3.16, 4.43, 4.96, 6.12, 6.98-7.05, 7.28-7.32, 7.50.

Examples 12(1) to 12(22)

The titled compounds having the following physical property values were obtained by performing the same procedures as in Example 11 and Example 12 using a corresponding amine in place of 1-(4-fluorophenyl)methanamine.

Example 12(1)

1-[4,6-dichloro-1-hydroxy-1-(trifluoromethyl)-2,3-dihydro-1H-inden-5-yl]-3-[(1-hydroxycyclohexyl)methyl]urea TLC: Rf 0.46 (hexane:ethyl acetate=1:1);

$^1$H-NMR (DMSO-d$_6$): δ 1.24-1.57, 2.17-2.27, 2.54-2.63, 2.82-3.07, 4.34, 6.35, 6.94, 7.43, 8.20.

Example 12(2)

1-[4,6-dichloro-1-hydroxy-1-(trifluoromethyl)-2,3-dihydro-1H-inden-5-yl]-3-[(4-methyltetrahydro-2H-pyran-4-yl)methyl]urea

[Chem. 40]

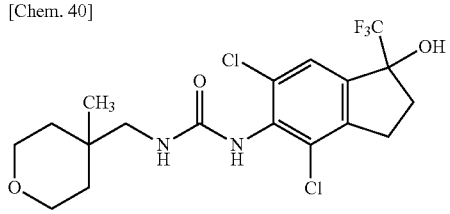

TLC: Rf 0. (Hexane:ethyl acetate=1:1);

$^1$H-NMR (DMSO-d$_6$): δ 0.93, 1.14-1.24, 1.37-1.46, 2.17-2.26, 2.53-2.62, 2.82-3.05, 3.45-3.65, 6.49, 6.94, 7.43, 7.93.

Example 12(3)

1-[4,6-dichloro-1-hydroxy-1-(trifluoromethyl)-2,3-dihydro-1H-inden-5-yl]-3-[(4,4-difluorocyclohexyl)methyl]urea TLC: Rf 0.64 (hexane:ethyl acetate=1:1);

$^1$H-NMR (DMSO-d$_6$): δ 1.12-1.26, 1.57-2.10, 2.18-2.28, 2.54-2.63, 2.82-3.07, 6.47, 6.95, 7.43, 7.98.

Example 12(4)

1-[4,6-dichloro-1-hydroxy-1-(trifluoromethyl)-2,3-dihydro-1H-inden-5-yl]-3-{[5-(trifluoromethyl)-2 pyridinyl]methyl}urea

[Chem. 41]

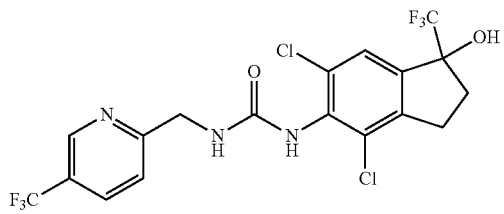

TLC: Rf 0.51 (hexane:ethyl acetate=1:1);

$^1$H-NMR (DMSO-d$_6$): δ 2.17-2.27, 2.57-2.63, 2.83-3.06, 4.48, 6.96, 7.13, 7.45, 7.59, 8.24, 8.46, 8.89.

Example 12(5)

1-[4,6-dichloro-1-hydroxy-1-(trifluoromethyl)-2,3-dihydro-H-inden-5-yl]-3-[(1R)-1-(4-fluorophenyl)ethyl]urea

[Chem. 42]

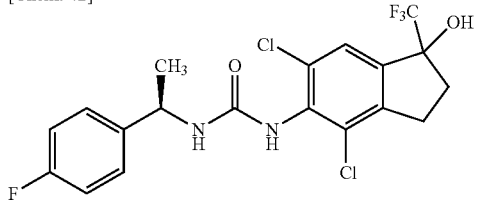

TLC: Rf 0.57 (hexane:ethyl acetate=1:1);
$^1$H-NMR (CDCl$_3$): δ 1.51, 2.20-2.30, 2.65-2.75, 2.84, 2.92-3.15, 4.88-4.99, 6.02, 7.01-7.07, 7.32-7.37, 7.48.

Example 12(6)

1-[4,6-dichloro-1-hydroxy-1-(trifluoromethyl)-2,3-dihydro-1H-inden-5-yl]-3-(2-pyridinylmethyl)urea LC retention time (min): 0.64;
$^1$H-NMR (CDCl$_3$): δ 2.18-2.30, 2.62-2.71, 2.88-3.13, 4.49, 7.21-7.25, 7.37-7.39, 7.48, 7.67-7.73, 8.46-8.49.

Example 12(7)

1-[4,6-dichloro-1-hydroxy-1-(trifluoromethyl)-2,3-dihydro-1H-inden-5-yl]-3-(3-pyridinylmethyl)urea LC retention time (min): 0.64;
$^1$H-NMR (CDCl$_3$): δ 2.21-2.30, 2.56-2.65, 2.89-2.96, 4.12-4.37, 6.52, 6.97, 7.15-7.18, 7.42, 7.61, 8.07.

Example 12(8)

1-[4,6-dichloro-1-hydroxy-1-(trifluoromethyl)-2,3-dihydro-1H-inden-5-yl]-3-[(5-methyl-1,2-oxazole-3-yl)methyl]urea

[Chem. 43]

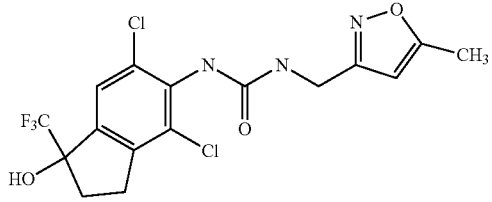

LC retention time (min): 0.83;
$^1$H-NMR (CDCl$_3$): δ 2.23-2.33, 2.40, 2.67-2.76, 2.94-3.17, 4.44, 5.28, 6.02, 6.35, 7.49.

Example 12(9)

1-[4,6-dichloro-1-hydroxy-1-(trifluoromethyl)-2,3-dihydro-1H-inden-5-yl]-3-{[6-(1-piperidinyl)-2 pyridinyl]methyl}urea

[Chem. 44]

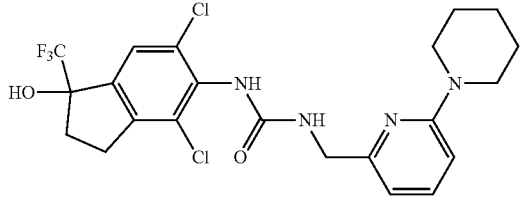

LC retention time (min): 0.80;
$^1$H-NMR (DMSO-d$_6$): δ 1.48-1.64, 2.17-2.27, 2.50-2.62, 2.82-3.06, 3.49-3.52, 4.19, 6.55, 6.64, 6.79, 6.94, 7.44-7.49, 8.31.

Example 12(10)

1-[4,6-dichloro-1-hydroxy-1-(trifluoromethyl)-2,3-dihydro-1H-inden-5-yl]-3-{[2-(1-piperidinyl)-4-pyridinyl]methyl}urea LC retention time (min): 0.75;
$^1$H-NMR (CDCl$_3$): δ 1.55-1.65, 2.20-2.30, 2.64-2.71, 2.88-3.12, 3.49-3.51, 4.35, 6.07, 6.50, 6.61, 7.50, 8.01.

Example 12(11)

1-[4,6-dichloro-1-hydroxy-1-(trifluoromethyl)-2,3-dihydro-1H-inden-5-yl]-3-(2-pyrazinylmethyl)urea LC retention time (min): 0.73;
$^1$H-NMR (CDCl$_3$): δ 2.23-2.32, 2.61-2.70, 2.91-3.12, 4.40-4.56, 4.98, 6.23, 7.15, 7.28, 8.25, 8.33, 8.40.

Example 12(12)

1-[4,6-dichloro-1-hydroxy-1-(trifluoromethyl)-2,3-dihydro-1H-inden-5-yl]-3-(2-pyrimidinylmethyl)urea LC retention time (min): 0.73;
$^1$H-NMR (CDCl$_3$): δ 2.22-2.31, 2.65-2.74, 2.93-3.16, 4.68, 6.06, 7.23, 7.46, 8.69.

Example 12(13)

1-(cyclopropylmethyl)-3-[4,6-dichloro-1-hydroxy-1-(trifluoromethyl)-2,3-dihydro-1H-inden-5-yl]urea

[Chem. 45]

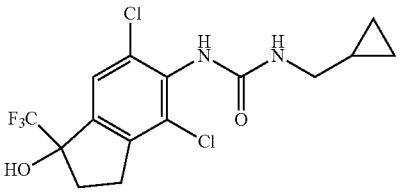

LC retention time (min): 0.87;
$^1$H-NMR (CDCl$_3$): δ 0.20-0.25, 0.49-0.55, 0.96-1.05, 2.22-2.31, 2.66-2.75, 2.94-3.17, 4.76, 6.09, 7.50.

Example 12(14)

1-[(5-bromo-2-pyridinyl)methyl]-3-[4,6-dichloro-1-hydroxy-1-(trifluoromethyl)-2,3-dihydro-1H-inden-5-yl]urea LC retention time (min): 0.86;
$^1$H-NMR (CDCl$_3$): δ 2.20-2.30, 2.60-2.72, 2.89-3.14, 4.47, 6.39, 7.31, 7.50, 7.83, 8.56.

Example 12(15)

1-[4,6-dichloro-1-hydroxy-1-(trifluoromethyl)-2,3-dihydro-1H-inden-5-yl]-3-[(5-fluoro-2-pyridinyl)methyl]urea LC retention time (min): 0.79;
$^1$H-NMR (CDCl$_3$): δ 2.22-2.32, 2.63-2.73, 2.94-3.13, 4.34, 5.95, 7.29-7.41, 8.29.

Example 12(16)

1-{[5-(4-chlorophenyl)-2-furyl]methyl}-3-[4,6-dichloro-1-hydroxy-1-(trifluoromethyl)-2,3-dihydro-1H-inden-5-yl]urea

[Chem. 46]

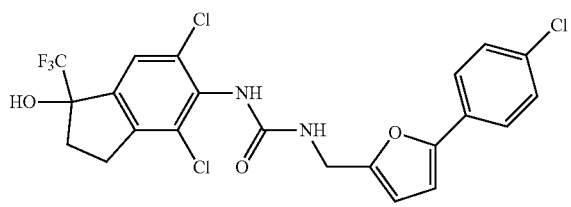

LC retention time (min): 1.08;
$^1$H-NMR (CDCl$_3$): δ 2.19-2.29, 2.65-2.74, 2.88-3.13, 4.48, 5.12, 6.24, 6.32, 6.54, 7.30-7.33, 7.48, 7.52-7.55.

Example 12(17)

1-[4,6-dichloro-1-hydroxy-1-(trifluoromethyl)-2,3-dihydro-1H-inden-5-yl]-3-[(1-methylcyclopropyl)methyl]urea LC retention time (min): 0.92;
$^1$H-NMR (CDCl$_3$): δ 0.30-0.44, 1.11, 2.21-2.32, 2.66-2.75, 2.94-3.16, 4.71, 6.09, 7.50.

Example 12(18)

1-[4,6-dichloro-1-hydroxy-1-(trifluoromethyl)-2,3-dihydro-1H-inden-5-yl]-3-[(6-methoxy-3-pyridinyl)methyl]urea LC retention time (min): 0.74;
$^1$H-NMR (CDCl$_3$): δ 2.21-2.30, 2.63-2.72, 2.89-3.11, 3.90, 4.30, 5.41, 6.50, 6.64, 7.41, 7.51, 7.83.

Example 12(19)

1-[4,6-dichloro-1-hydroxy-1-(trifluoromethyl)-2,3-dihydro-1H-inden-5-yl]-3-(1,3-thiazol-5-ylmethyl)urea LC retention time (min): 0.71;
$^1$H-NMR (DMSO-d$_6$): δ 2.17-2.67, 2.42-2.62, 2.82-3.06, 4.48, 6.94, 7.00, 7.44, 7.74, 8.22, 8.95.

Example 12(20)

1-[4,6-dichloro-1-hydroxy-1-(trifluoromethyl)-2,3-dihydro-1H-inden-5-yl]-3-(1,2-oxazol-3-ylmethyl)urea LC retention time (min): 0.79;
$^1$H-NMR (CDCl$_3$): δ 2.22-2.32, 2.66-2.75, 2.94-3.12, 4.47, 5.53, 6.39, 6.61, 7.47, 8.31.

Example 12(21)

1-[4,6-dichloro-1-hydroxy-1-(trifluoromethyl)-2,3-dihydro-1H-inden-5-yl]-3-(1H-indol-2-ylmethyl)urea

[Chem. 47]

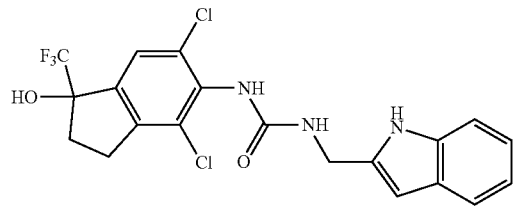

LC retention time (min): 0.96;
$^1$H-NMR (CDCl$_3$): δ 2.17-2.28, 2.63-2.72, 2.91-3.13, 4.50, 6.32, 7.04-7.09, 7.12-7.18, 7.30-7.33, 7.49, 7.53-7.56.

Example 12(22)

1-[4,6-dichloro-1-hydroxy-1-(trifluoromethyl)-2,3-dihydro-1H-inden-5-yl]-3-{[5-(trifluoromethyl)-2 pyrimidinyl]methyl}urea LC retention time (min): 0.88;
$^1$H-NMR (CDCl$_3$): δ 2.22-2.32, 2.66-2.76, 2.94-3.18, 4.81, 5.90, 6.62, 7.50, 8.95.

Example 13(1)

1-[4,6-dichloro-1-hydroxy-1-(trifluoromethyl)-2,3-dihydro-1H-inden-5-yl]-3-(4-fluorobenzyl)urea
(First Peak)

Example 13(2)

1-[4,6-dichloro-1-hydroxy-1-(trifluoromethyl)-2,3-dihydro-1H-inden-5-yl]-3-(4-fluorobenzyl)urea
(Second Peak)

The compound (30 mg) produced in Example 12 was subjected to optical resolution by supercritical fluid chromatography (carbon dioxide:isopropyl alcohol=70:30, flow rate: 10 mL/min), whereby the title compounds having the following physical property values were obtained (Example 13(1): 6.3 mg, Example 13(2): 5.8 mg).

Example 13(1)

SFC retention time: 5.50 min
TLC: Rf 0.43 (hexane:ethyl acetate=1:2);
$^1$H-NMR (CDCl$_3$): δ 2.20-2.30, 2.65-2.74, 2.91-3.14, 4.40, 5.07, 6.22, 6.97-7.03, 7.25-7.30, 7.48.

Example 13(2)

SFC retention time: 7.03 min
TLC: Rf 0.43 (hexane:ethyl acetate=1:2);
$^1$H-NMR (CDCl$_3$): δ 2.20-2.30, 2.65-2.74, 2.91-3.14, 4.40, 5.05, 6.21, 6.96-7.03, 7.25-7.30, 7.48.

Example 14

5-bromo-1-(trifluoromethyl)-1-indanol

To a tetrahydrofuran (20 mL) solution of 5-bromo-1-indanone (CAS Registry Number: 174349-93-0) (2.00 g), trimethyl(trifluoromethyl)silane (2.2 mL) (CAS Registry Number: 81290-20-2) was added, and tetraammonium fluoride (0.47 mL, a 1 M tetrahydrofuran solution) was added thereto under ice-cooling. After the reaction mixture was stirred at room temperature for 3 hours, tetrabutylammonium fluoride (9.5 mL, a 1 M tetrahydrofuran solution) was added thereto, followed by stirring at room temperature for 10 minutes. The reaction mixture was diluted with water (20 mL), and 1 N hydrochloric acid (5 mL) was added thereto, and then extraction was performed with ethyl acetate. The organic layer was dried over anhydrous sodium sulfate, and concentrated under reduced pressure. The resulting residue was purified by silica gel column chromatography (hexane:ethyl acetate=100:0→70:30), whereby the title compound having the following physical property values was obtained (1.77 g).
TLC: Rf 0.66 (hexane:ethyl acetate=3:1);
$^1$H-NMR (CDCl$_3$): δ 2.19-2.30, 2.45, 2.62-2.72, 2.93-3.15, 7.35-7.37, 7.42-7.46.

Example 15(1)

(1S)-5-bromo-1-(trifluoromethyl)-2,3-dihydro-1H-inden-1-yl [(1S)-1-(1-naphthyl)ethyl]carbamate

Example 15(2)

(1R)-5-bromo-1-(trifluoromethyl)-2,3-dihydro-1H-inden-1-yl [(1S)-1-(1-naphthyl)ethyl]carbamate To a dichloromethane (8 mL) solution of the compound (1.37 g) produced in Example 14, N,N-dimethyl-4-pyridinamine (953 mg) (CAS Registry Number: 1122-58-3) was added, and 4-nitrophenyl chloroformate (CAS Registry Number: 7693-46-1) (1.38 g) was added thereto under ice-cooling. After the reaction mixture was stirred for 50 minutes under ice-cooling, (1S)-1-(1-naphthyl)ethanamine (CAS Registry Number 10420-89-0) (1.67 g) was added thereto. After the reaction mixture was stirred for 10 minutes under ice-cooling, the temperature was increased to room temperature, followed by stirring for 15 minutes. To the reaction mixture, a mixed solvent of ethyl acetate (10 mL) and tert-butyl methyl ether (10 mL) was added, and the precipitate was separated by filtration. The filtrate was sequentially washed with a 1 N aqueous sodium hydroxide solution, 1 N hydrochloric acid, and a saturated aqueous sodium chloride solution, and the organic layer was dried over anhydrous sodium sulfate, and then concentrated under reduced pressure. The resulting residue was purified by silica gel column chromatography (hexane:ethyl acetate=100:0→70:30), whereby a mixture of the title compounds of Example 15(1) and Example 15(2) was obtained. This mixture was subjected to recrystallization in a mixed solvent of hexane and ethyl acetate (4:1), and the resulting crystal was collected by filtration, whereby the title compound having the following physical property values was obtained (Example 15(1) (581 mg)). Further, by concentrating the filtrate under reduced pressure, the title compound having the following physical property values was obtained (Example 15(2) (590 mg)).

Example 15(1)

TLC: Rf 0.79 (hexane:tert-butyl methyl ether=4:1);
$^1$H-NMR (CDCl$_3$): δ 1.65, 2.62-2.70, 2.86-3.09, 3.27-3.37, 5.14-5.16, 5.42-5.50, 7.14-7.16, 7.34-7.53, 7.78-7.88.

Example 15(2)

TLC: Rf 0.36 (hexane:tert-butyl methyl ether=4:1);
$^1$H-NMR (CDCl$_3$): δ 1.57, 2.56-2.76, 2.94-3.04, 3.21-3.32, 5.22-5.25, 5.46-5.56, 7.30-7.33, 7.41-7.55, 7.78-7.81, 7.85-7.88, 8.00-8.03.

Example 16

(1R)-5-bromo-1-(trifluoromethyl)-1-indanol

The compound (569 mg) produced in Example 15(2) was suspended in 1,4-dioxane (3 mL), and a solution of lithium chloride (284 mg) in water (3 mL) was added thereto. The reaction mixture was stirred at 50° C. for 1 hour. The reaction mixture was diluted with water, and extraction was performed with ethyl acetate. The organic layer was dried over anhydrous sodium sulfate, and concentrated under reduced pressure. The resulting residue was purified by silica gel column chromatography (hexane:ethyl acetate=100:0→70:30), whereby the title compound having the following physical property values was obtained (285 mg).
TLC: Rf 0.48 (hexane:ethyl acetate=3:1);
$^1$H-NMR (CDCl$_3$): δ 2.19-2.29, 2.45, 2.62-2.72, 2.93-3.15, 7.35-7.37, 7.41-7.45.

Example 17

2-methyl-2-propanyl[(1R)-1-hydroxy-1-(trifluoromethyl)-2,3-dihydro-1H-inden-5-yl]carbamate To a 1,4-dioxane (2.5 mL) solution of the compound (143 mg) produced in Example 16, palladium(II) acetate (18 mg), 4,5-bis(diphenylphosphino)-9,9-dimethylxanthene (71 mg), cesium carbonate (399 mg), and tert-butyl carbamate (143 mg) were added, followed by stirring at 110° C. for 1 hour in an argon atmosphere. The reaction mixture was filtered, and the filtrate was concentrated under reduced pressure. The resulting residue was purified by silica gel column chromatography (hexane:ethyl acetate=100:0→70:30), whereby the title compound having the following physical property values was obtained (231 mg).
TLC: Rf 0.31 (hexane:ethyl acetate=3:1);
$^1$H-NMR (CDCl$_3$): δ 1.52, 2.18-2.28, 2.44, 2.60-2.69, 2.90-3.13, 6.56, 7.08-7.12, 7.37-7.40, 7.50.

Example 18

(1R)-5-amino-1-(trifluoromethyl)-1-indanol

To a dichloromethane (4 mL) solution of the compound (231 mg) obtained in Example 17, trifluoroacetic acid (1 mL) was added under ice-cooling, followed by stirring for 30 minutes, and then, the temperature was increased to room temperature, followed by stirring for 15 minutes. The reaction mixture was concentrated under reduced pressure, and the resulting residue was diluted with a saturated aqueous sodium hydrogen carbonate solution, and then, extraction was performed with ethyl acetate. The organic layer was sequentially washed with water and a saturated aqueous sodium chloride solution, and dried over anhydrous sodium sulfate, and then concentrated under reduced pressure. The resulting residue was purified by silica gel column chromatography (hexane:ethyl acetate=50:50), whereby the title compound having the following physical property values was obtained (119 mg).

TLC: Rf 0.51 (hexane:ethyl acetate=1:1);

$^1$H-NMR (CDCl$_3$): δ 2.16-2.29, 2.57-2.66, 2.83-3.07, 3.77, 6.56-6.60, 7.25-7.28.

Example 19

(1R)-5-amino-4,6-dichloro-1-(trifluoromethyl)-1-indanol

To a N,N-dimethylformamide (3 mL) solution of the compound (119 mg) produced in Example 18, N-chlorosuccinimide (160 mg) was added, followed by stirring overnight at room temperature. The temperature of the reaction mixture was increased to 40° C. followed by stirring for 1 hour, and then, the temperature was increased to 50° C., followed by stirring for 3 hours. The reaction mixture was diluted with water, and extraction was performed with ethyl acetate. The organic layer was sequentially washed with water and a saturated aqueous sodium chloride solution, and dried over anhydrous sodium sulfate, and then concentrated under reduced pressure. The resulting residue was purified by preparative thin layer chromatography (silica gel 60 F254, 0.5 mm, 20×20 cm, manufactured by Merck; hexane:ethyl acetate=4:1), whereby the title compound having the following physical property values was obtained (70 mg).

$^1$H-NMR (CDCl$_3$): δ 2.28-2.29, 2.37, 2.62-2.71, 2.89-3.13, 4.60, 7.32.

Example 20

(1R)-4,6-dichloro-1-(trifluoromethyl)-1-[(trimethylsilyl)oxy]-5-indanamine

To a tetrahydrofuran (2 mL) solution of the compound (70 mg) produced in Example 19, imidazole (83 mg) and chlorotrimethylsilane (155 μL) were added, followed by stirring at room temperature for 1 hour. The reaction mixture was diluted with water, and extraction was performed with ethyl acetate. The organic layer was washed with a saturated aqueous sodium chloride solution, and dried over anhydrous sodium sulfate, and then concentrated under reduced pressure. The resulting residue was purified by silica gel column chromatography (hexane), whereby the title compound having the following physical property values was obtained (72 mg).

TLC: Rf 0.51 (hexane:ethyl acetate=1:1);

$^1$H-NMR (CDCl$_3$): δ 0.01, 2.16-2.26, 2.57-2.66, 2.84-3.05, 4.56, 7.27.

Example 21

1-[(1R)-4,6-dichloro-1-hydroxy-1-(trifluoromethyl)-2,3-dihydro-1H-inden-5-yl]-3-[(1R)-1-(4-fluorophenyl)ethyl]urea

[Chem. 48]

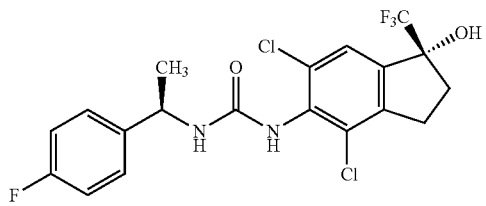

To a tetrahydrofuran (2 mL) solution of the compound (34 mg) produced in Example 20 and triphosgene (28 mg), N,N-diisopropylethylamine (18 μL) was added, and the resulting mixture was stirred at 40° C. for 3 hours, and then concentrated under reduced pressure. A tetrahydrofuran (0.5 mL) solution of the obtained residue was added to a tetrahydrofuran (1 mL) solution of (1R)-1-(4-fluorophenyl)ethanamine (CAS Registry Number: 374898-01-8) (29 mg), followed by stirring at room temperature for 1 hour. The reaction mixture was diluted with water, and extraction was performed with ethyl acetate. The organic layer was dried over anhydrous sodium sulfate, and concentrated under reduced pressure. To the resulting residue, a mixed solvent of dichloromethane, methanol, and trifluoroacetic acid (2.5 mL, 2:2:1) was added, followed by stirring at room temperature for 3 hours. The reaction mixture was diluted with a saturated aqueous sodium hydrogen carbonate solution, and extraction was performed with ethyl acetate. The organic layer was washed with a saturated aqueous sodium chloride solution, and dried over anhydrous sodium sulfate, and then concentrated under reduced pressure. The resulting residue was purified by silica gel column chromatography (hexane:ethyl acetate=50:50), whereby the title compound having the following physical property values was obtained (37 mg).

TLC: Rf 0.31 (hexane:ethyl acetate=2:1);

SFC retention time: 3.07 min $^1$H-NMR (DMSO-d$_6$): δ 1.38, 2.16-2.27, 2.55-2.63, 2.81-3.04, 4.74-4.83, 6.91, 6.95, 7.13-7.19, 7.36-7.41, 7.43, 7.96.

Example 22

1-[(1S)-4,6-dichloro-1-hydroxy-1-(trifluoromethyl)-2,3-dihydro-1H-inden-5-yl]-3-[(1R)-1-(4-fluorophenyl)ethyl]urea

[Chem. 49]

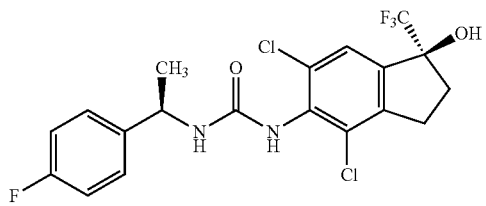

The compound (70 mg) of Example 12(5) was subjected to optical resolution by supercritical fluid chromatography (carbon dioxide:isopropyl alcohol=85:15, flow rate: 30 mL/min), whereby the title compound having the following physical property values was obtained (31.0 mg).

SFC retention time: 5.67 min
TLC: Rf 0.44 (hexane:ethyl acetate=1:1);
$^1$H-NMR (CDCl$_3$): δ 1.38, 1.69, 2.12-2.22, 2.56-2.65, 2.82-3.04, 3.65, 4.80-4.89, 5.40, 6.51, 6.92-6.98, 7.21-7.23, 7.37.

Example 23

5-fluoro-2,2-dimethyl-1-indanone

To a N,N-dimethylformamide (60 mL) solution of 5-fluoro-1-indanone (CAS Registry Number: 700-84-5) (3.96 g), sodium hydride (2.32 g) was added in an argon atmosphere under ice-cooling. After the reaction mixture was stirred for 10 minutes under ice-cooling, methyl iodide (8.21 mL) and N,N-dimethylformamide (20 mL) were added thereto. The reaction mixture was stirred at room temperature for 3 hours. To the reaction mixture, water was added under ice-cooling, and extraction was performed with ethyl acetate. The organic layer was sequentially washed with water and a saturated aqueous sodium chloride solution, and dried over anhydrous sodium sulfate, and then concentrated under reduced pressure. The resulting residue was purified by silica gel column chromatography (hexane:ethyl acetate=100:0→90:10), whereby the title compound having the following physical property values was obtained (4.12 g).

TLC: Rf 0.71 (hexane:ethyl acetate=3:1);
$^1$H-NMR (CDCl$_3$): δ 1.24, 2.99, 7.04-7.11, 7.74-7.79.

Example 24

5-[(3,4-dimethoxybenzyl)amino]-2,2-dimethyl-1-indanone

After a dimethyl sulfoxide (30 mL) solution of the compound (3.60 g) produced in Example 23 and 1-(3,4-dimethoxyphenyl)methanamine (CAS Registration number: 5763-61-1) (3.60 g) was stirred at 130° C. for 5 hours, the temperature of the reaction mixture was increased to 150° C., and the mixture was stirred for 7 hours. The reaction mixture was cooled to room temperature, and thereafter diluted with water, and then, extraction was performed with ethyl acetate. The organic layer was sequentially washed with water and a saturated aqueous sodium chloride solution, and dried over anhydrous sodium sulfate, and then concentrated under reduced pressure. The resulting residue was purified by silica gel column chromatography (hexane:ethyl acetate=80:20→50:50), whereby the title compound having the following physical property values was obtained (3.19 g).

TLC: Rf 0.48 (hexane:ethyl acetate=1:1);
$^1$H-NMR (CDCl$_3$): δ 1.20, 2.86, 3.88, 3.89, 4.33, 4.57, 6.50, 6.57-6.61, 6.84-6.93, 7.57-7.60.

Example 25

5-amino-2,2-dimethyl-1-indanone

To a dichloromethane (10 mL) solution of the compound (3.19 g) obtained in Example 24, trifluoroacetic acid (10 mL) was added. The reaction mixture was stirred for 14 hours while heating under reflux. The reaction mixture was concentrated under reduced pressure, and the resulting residue was diluted with water. The aqueous layer was washed with a mixed solvent of tert-butyl methyl ether and ethyl acetate (1:1), and neutralized with a 2 N aqueous sodium hydroxide solution, and then, extraction was performed with ethyl acetate. The organic layer was washed with a saturated aqueous sodium chloride solution, and dried over anhydrous sodium sulfate, and then concentrated under reduced pressure. The resulting residue was purified by silica gel column chromatography (hexane:ethyl acetate=70:30→50:50), whereby the title compound having the following physical property values was obtained (1.29 g).

TLC: Rf 0.42 (hexane:ethyl acetate=1:1);
$^1$H-NMR (CDCl$_3$): δ 1.20, 2.86, 6.56-6.62, 7.57-7.60.

Example 26

5-amino-4,6-dichloro-2,2-dimethyl-1-indanone

To a N,N-dimethylformamide (15 mL) solution of the compound (1.29 g) produced in Example 25, N-chlorosuccinimide (2.95 g) was added under ice-cooling, followed by stirring at room temperature for 6 hours, and then stirring at 50° C. for 2.5 hours. The reaction mixture was diluted with water, and extraction was performed with ethyl acetate. The organic layer was sequentially washed with water and a saturated aqueous sodium chloride solution, and dried over anhydrous sodium sulfate, and then concentrated under reduced pressure. The resulting residue was purified by silica gel column chromatography (hexane:ethyl acetate=100:0→80:20→50:50), whereby the title compound having the following physical property values was obtained (1.60 g).

TLC: Rf 0.88 (hexane:ethyl acetate=1:1);
$^1$H-NMR (CDCl$_3$): δ 1.23, 2.89, 5.04, 7.64.

Example 27

1-(4,6-dichloro-2,2-dimethyl-1-oxo-2,3-dihydro-1H-inden-5-yl)-3-(4-fluorobenzyl)urea To a tetrahydrofuran (4 mL) solution of the compound (200 mg) produced in Example 26, N,N-diisopropylethylamine (154 μL) and triphosgene (267 mg) were added, and the resulting mixture was stirred at room temperature for 2 hours, and then concentrated under reduced pressure. The resulting residue was dissolved in tetrahydrofuran (4 mL), and 1-(4-fluorophenyl)methanamine (CAS Registry Number: 140-75-0) (205 mg) was added thereto under ice-cooling, followed by stirring at room temperature for 2 hours. The reaction mixture was diluted with water, and extraction was performed with ethyl acetate. The organic layer was dried over anhydrous sodium sulfate, and then concentrated under reduced pressure. The resulting residue was purified by silica gel column chromatography (hexane:ethyl acetate=80:20→50:50), whereby the title compound having the following physical property values was obtained (91 mg).

TLC: Rf 0.61 (hexane:ethyl acetate=1:1);
$^1$H-NMR (CDCl$_3$): δ 1.25, 2.95, 4.45, 5.12, 6.33, 7.00-7.06, 7.28-7.34, 7.74.

Example 28

1-(4,6-dichloro-1-hydroxy-2,2-dimethyl-2,3-dihydro-1H-inden-5-yl)-3-(4-fluorobenzyl)urea To the compound (39 mg) produced in Example 27, ethanol (2 mL) was added, and then, sodium borohydride (11 mg) was added thereto under ice-cooling. After the reaction mixture was stirred at room temperature for 1.5 hours, a small amount of a saturated aqueous ammonium chloride solution was added thereto under ice-cooling, followed by dilution with water, and then extraction was performed with ethyl acetate. The organic layer was dried over anhydrous sodium sulfate, and concentrated under reduced pressure. The resulting residue was purified by silica gel column chromatography (hexane:ethyl acetate=80:20→40:60), whereby the title compound having the following physical property values was obtained (34 mg).

TLC: Rf 0.46 (hexane:ethyl acetate=1:1);

$^1$H-NMR (CDCl$_3$): δ 1.03, 1.20, 1.90, 2.66, 2.82, 4.42, 4.69, 4.86, 6.02, 6.97-7.03, 7.24-7.30, 7.37.

Example 29

6-bromo-1,1-dimethylindane

To titanium(IV) chloride (29.8 mL, a 1 M dichloromethane solution), dimethylzinc (42.6 mL, a 1 M hexane solution) was added at −40° C., followed by stirring for 20 minutes. Thereafter, a dichloromethane (24 mL) solution of 6-bromo-1-indanone (CAS Registry Number: 14548-39-1) (3.00 g) was added thereto, followed by stirring overnight at room temperature. To the reaction mixture, a small amount of methanol was added under ice-cooling, followed by dilution with water, and then extraction was performed with ethyl acetate. The organic layer was washed with a saturated aqueous sodium chloride solution, and dried over anhydrous sodium sulfate, and then concentrated under reduced pressure. The resulting residue was purified by silica gel column chromatography (hexane:ethyl acetate=100:0→90:10), whereby the title compound having the following physical property values was obtained (2.84 g).

TLC: Rf 0.78 (hexane:ethyl acetate=1:1);

$^1$H-NMR (DMSO-d$_6$): δ 1.21, 1.84-1.89, 2.78-2.83, 7.14, 7.28, 7.34.

Example 30

5-bromo-3,3-dimethyl-1-indanone

To an acetic acid (37 mL) solution of the compound (2.70 g) produced in Example 29, a mixed solution of acetic acid (18 mL) and water (18 mL) containing chromium trioxide (7.20 g) was added, followed by stirring at 60° C. for 3 hours. After the reaction was stopped by adding diisopropyl alcohol to the reaction mixture under ice-cooling, the reaction mixture was subjected to liquid-liquid separation by adding ethyl acetate and a 2 N aqueous sodium hydroxide solution. The aqueous layer was extracted with ethyl acetate, and the combined organic layer was sequentially washed with a saturated aqueous sodium hydrogen carbonate solution and a saturated aqueous sodium chloride solution, and dried over anhydrous sodium sulfate, and then concentrated under reduced pressure. The resulting residue was purified by silica gel column chromatography (hexane:ethyl acetate=80:20→60:40), whereby the title compound having the following physical property values was obtained (1.43 g).

TLC: Rf 0.68 (hexane:ethyl acetate=1:1);

$^1$H-NMR (CDCl$_3$): δ 1.42, 2.59, 7.49-7.57, 7.63-7.66.

Example 31

2-methyl-2-propanyl (3,3-dimethyl-1-oxo-2,3-dihydro-1H-inden-5-yl)carbamate

To a 1,4-dioxane (15 mL) solution of the compound (1.00 g) produced in Example 30, palladium(II) acetate (94 mg), 4,5-bis(diphenylphosphino)-9,9-dimethylxanthene (363 mg), cesium carbonate (2.04 g), and tert-butyl carbamate (734 mg) were added, followed by stirring at 110° C. for 1 hour under microwave irradiation (Biotage Initiator Sixty (trade name), manufactured by Biotage, Inc.). To the reaction mixture, a saturated sodium hydrogen carbonate was added, and extraction was performed with ethyl acetate. The organic layer was washed with a saturated aqueous sodium chloride solution, and dried over anhydrous magnesium sulfate, and then concentrated under reduced pressure. The resulting residue was purified by silica gel column chromatography (hexane:ethyl acetate=80:20), whereby the title compound having the following physical property values was obtained (1.15 g).

TLC: Rf 0.60 (hexane:ethyl acetate=2:1);

$^1$H-NMR (CDCl$_3$): δ 1.41, 1.54, 2.57, 6.80, 7.13, 7.62, 7.73.

Example 32

5-amino-3,3-dimethyl-1-indanone

To a dichloromethane (15 mL) solution of the compound (1.15 g) produced in Example 31, trifluoroacetic acid (10 mL) was added under ice-cooling, followed by stirring at room temperature for 1.5 hours. To the reaction mixture, toluene was added, and the mixture was concentrated under reduced pressure. The resulting residue was diluted with a saturated aqueous sodium hydrogen carbonate solution, and extraction was performed with ethyl acetate. The organic layer was washed with a saturated aqueous sodium chloride solution, and dried over anhydrous magnesium sulfate, and then concentrated under reduced pressure, whereby the title compound having the following physical property values was obtained (693 mg).

$^1$H-NMR (CD$_3$OD): δ 1.35, 2.47, 6.58-6.63, 7.37-7.40.

Example 33

5-amino-4,6-dichloro-3,3-dimethyl-1-indanone

To a N,N-dimethylformamide (10 mL) solution of the compound (693 mg) produced in Example 32, N-chlorosuccinimide (1.06 g) was added, followed by stirring at room temperature for 20 hours. The reaction mixture was diluted with a saturated aqueous sodium hydrogen carbonate solution, and extraction was performed with a mixed solvent of ethyl acetate and hexane. The organic layer was washed with a saturated aqueous sodium chloride solution, and dried over anhydrous magnesium sulfate, and then concentrated under reduced pressure. The resulting residue was purified by silica gel column chromatography (hexane:ethyl acetate=80:20), whereby the title compound having the following physical property values was obtained (480 mg).

TLC: Rf 0.71 (hexane:ethyl acetate=2:1);

$^1$H-NMR (CDCl$_3$): δ 1.57, 2.60, 5.14, 7.61.

Example 34

1-(4,6-dichloro-3,3-dimethyl-1-oxo-2,3-dihydro-1H-inden-5-yl)-3-{[5-(trifluoromethyl)-2-pyridinyl]methyl}urea To a tetrahydrofuran (4 mL) solution of the compound (200 mg) produced in Example 33, triphosgene (267 mg) and diisopropylethylamine (156 μL) were added, and the resulting mixture was stirred at room temperature for 20 hours, and then concentrated under reduced pressure. To the resulting residue, tetrahydrofuran (3 mL) was added, and then, 1-[5-(trifluoromethyl)-2-pyridinyl]methanamine hydrochloride (583 mg) (CAS Registry Number: 164341-39-3) (173 mg) and diisopropylethylamine (176 μL) were added, followed by stirring at room temperature for 20 hours. The reaction mixture was diluted with a saturated aqueous sodium hydrogen carbonate solution, and extraction was performed with ethyl acetate. The organic layer was washed with a saturated aqueous sodium chloride solution, and dried over anhydrous magnesium sulfate, and then concentrated under reduced pressure. The resulting residue was purified by silica gel column chromatography (hexane:ethyl acetate=40:60), whereby the title compound having the following physical property values was obtained (100 mg).

TLC: Rf 0.29 (hexane:ethyl acetate=1:1);
$^1$H-NMR (DMSO-$d_6$): δ 1.53, 2.71, 4.50, 7.25, 7.60, 7.67, 8.26, 8.67, 8.91.

Example 35

1-(4,6-dichloro-1-hydroxy-1,3,3-trimethyl-2,3-dihydro-1H-inden-5-yl)-3-{[5-(trifluoromethyl)-2 pyridinyl]methyl}urea

[Chem. 50]

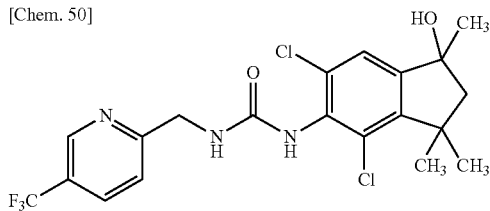

To cerium(III) chloride (262 mg), tetrahydrofuran (2 mL) was added, followed by stirring at room temperature for 1 hour in an argon atmosphere, and then, methyllithium (0.96 mL, a 1.1 M diethyl ether solution) was added thereto at −78° C., followed by stirring for 30 minutes. To the reaction mixture, a tetrahydrofuran (2 mL) solution of the compound (95 mg) produced in Example 34 was added at −78° C., followed by stirring at room temperature for 17 hours. To the reaction mixture, a saturated aqueous ammonium chloride solution and 1 N hydrochloric acid were added, and extraction was performed with ethyl acetate. The organic layer was washed with a saturated aqueous sodium chloride solution, and dried over anhydrous magnesium sulfate, and then concentrated under reduced pressure. The resulting residue was purified by silica gel column chromatography (hexane:ethyl acetate=30:70), whereby the title compound having the following physical property values was obtained (67 mg).

TLC: Rf 0.25 (hexane:ethyl acetate=1:1);
$^1$H-NMR (DMSO-$d_6$): δ 1.39, 1.45, 1.46, 1.99-2.14, 4.47, 5.15, 7.06, 7.35, 7.57-7.60, 8.23-8.27, 8.89.

Example 36

5-bromo-2-fluoro-1-indanone

To 5-bromo-1-indanone (CAS Registry Number: 174349-93-0) (5.00 g), methanol (50 mL) and Selectfluor (registered trademark) (CAS Registry Number: 140681-55-6) (10.0 g) were added, followed by stirring for 2 hours while heating under reflux. The reaction mixture was filtered through Celite (trade name), and the filtrate was concentrated under reduced pressure. The resulting residue was dissolved in tetrahydrofuran (20 mL), and 1 N hydrochloric acid (20 mL) was added thereto, followed by stirring at room temperature for 3 hours. To the reaction mixture, a 2 N aqueous sodium hydroxide solution (20 mL) was added, and the mixture was diluted with a saturated aqueous sodium hydrogen carbonate solution, and then, extraction was performed with ethyl acetate. The organic layer was washed with a saturated aqueous sodium chloride solution, and dried over anhydrous magnesium sulfate, and then concentrated under reduced pressure, whereby the title compound having the following physical property values was obtained (5.40 g).

$^1$H-NMR (CDCl$_3$): δ 3.15-3.30, 3.56-3.67, 5.15-5.19, 5.32-5.36, 7.57-7.60, 7.65-7.68.

Example 37

5-bromo-2,2-difluoro-1-indanone

To a dichloromethane (50 mL) solution of the compound (5.40 g) produced in Example 36, triethylamine (16 mL) and dimethyl(2-methyl-2-propanyl)silyl trifluoromethanesulfonate (CAS Registry Number: 69739-34-0) (9.30 g) were added, followed by stirring at room temperature for 1 hour. The reaction mixture was diluted with a saturated aqueous sodium hydrogen carbonate solution, and extraction was performed with ethyl acetate. The organic layer was dried over anhydrous sodium sulfate, and then concentrated under reduced pressure. The resulting residue was dissolved in acetonitrile (50 mL), and Selectfluor (registered trademark) (CAS Registry Number: 140681-55-6) (10.0 g) was added thereto, followed by stirring at room temperature for 2 hours. The reaction mixture was diluted with a saturated aqueous sodium hydrogen carbonate solution, and extraction was performed with ethyl acetate. The organic layer was washed with a saturated aqueous sodium chloride solution, and dried over anhydrous magnesium sulfate, and then concentrated under reduced pressure. To the resulting residue, hexane was added, and the precipitate was collected by filtration, whereby the title compound having the following physical property values was obtained (5.45 g).

$^1$H-NMR (CDCl$_3$): δ 3.51-3.60, 7.63-7.75.

Example 38

2-methyl-2-propanyl(2,2-difluoro-1-oxo-2,3-dihydro-1H-inden-5-yl)carbamate

To a 1,4-dioxane (40 mL) solution of the compound (5.45 g) produced in Example 37, palladium(II) acetate (495 mg), 4,5-bis(diphenylphosphino)-9,9-dimethylxanthene (1.91 g), cesium carbonate (10.8 g), and tert-butyl carbamate (3.88 g) were added, followed by degassing, and then stirring for 1 hour while heating under reflux. To the reaction mixture, water and ethyl acetate were added, and the mixture was filtered through Celite (trade name). The filtrate was subjected to liquid-liquid separation, and the aqueous layer was extracted with ethyl acetate. The combined organic layer was dried over anhydrous magnesium sulfate, and concentrated under reduced pressure. The resulting residue was purified by silica gel column chromatography (hexane:ethyl acetate=80:20), whereby the title compound having the following physical property values was obtained (3.21 g).

TLC: Rf 0.48 (hexane:ethyl acetate=3:1);

$^1$H-NMR (CDCl$_3$): δ 1.55, 3.47-3.55, 6.92, 7.18-7.21, 7.77-7.81.

Example 39

5-amino-2,2-difluoro-1-indanone

To a dichloromethane (56 mL) solution of the compound (3.21 g) produced in Example 38, trifluoroacetic acid (28 mL) was added under ice-cooling, followed by stirring at room temperature for 1.5 hours. To the reaction mixture, toluene was added, and the mixture was concentrated under reduced pressure. The resulting residue was diluted with a saturated aqueous sodium hydrogen carbonate solution, and extraction was performed with ethyl acetate. The organic layer was washed with a saturated aqueous sodium chloride solution, and dried over anhydrous magnesium sulfate, and then concentrated under reduced pressure, whereby the title compound having the following physical property values was obtained (2.00 g).

$^1$H-NMR (CD$_3$OD): δ 3.33-3.41, 6.56, 6.68, 7.53.

Example 40

5-amino-4,6-dichloro-2,2-difluoro-1-indanone

To a N,N-dimethylformamide (20 mL) solution of the compound (2.00 g) produced in Example 39, N-chlorosuccinimide (3.20 g) was added, followed by stirring at 60° C. for 20 hours. After the reaction mixture was cooled to room temperature, the mixture was diluted with a saturated aqueous sodium hydrogen carbonate solution, and extraction was performed with a mixed solvent of ethyl acetate and hexane (1:1). The organic layer was washed with a saturated aqueous sodium chloride solution, and dried over anhydrous magnesium sulfate, and then concentrated under reduced pressure. To the resulting residue, tert-butyl methyl ether and hexane (1:1) were added, and the precipitate was collected by filtration, whereby the title compound having the following physical property values was obtained (1.70 g). Further, the filtrate was concentrated and the resulting residue was purified by silica gel column chromatography (hexane:ethyl acetate=70:30) whereby the title compound having the following physical property values was obtained (520 mg).

TLC: Rf 0.30 (hexane:ethyl acetate=3:1);

$^1$H-NMR (DMSO-d$_6$): δ 3.50-3.59, 7.29, 7.75.

Example 41

4,6-dichloro-2,2-difluoro-1-methyl-1-[(trimethylsilyl)oxy]-5-indanamine

To cerium(III) chloride (10.9 g), tetrahydrofuran (100 mL) was added, followed by stirring at room temperature for 1 hour in an argon atmosphere, and then, methyllithium (39.7 mL, a 1.1 M diethyl ether solution) was added thereto at −78° C., followed by stirring for 30 minutes. To the reaction mixture, a tetrahydrofuran (100 mL) solution of the compound (2.22 g) produced in Example 40 was added at −78° C., followed by stirring at room temperature for 17 hours. To the reaction mixture, a saturated aqueous ammonium chloride solution and 1 N hydrochloric acid were added, and extraction was performed with ethyl acetate. The organic layer was washed with a saturated aqueous sodium chloride solution, and dried over anhydrous magnesium sulfate, and then concentrated under reduced pressure. The resulting residue was dissolved in tetrahydrofuran (30 mL), and then, imidazole (3.00 g) and chlorotrimethylsilane (4.8 mL) were added thereto, followed by stirring at room temperature for 1 hour. The reaction mixture was diluted with a saturated aqueous sodium hydrogen carbonate solution, and extraction was performed with ethyl acetate. The organic layer was washed with a saturated aqueous sodium chloride solution, and dried over anhydrous sodium sulfate, and then concentrated under reduced pressure. The resulting residue was purified by silica gel column chromatography (hexane:ethyl acetate=95:5), whereby the title compound having the following physical property values was obtained (2.60 g).

TLC: Rf 0.80 (hexane:ethyl acetate=5:1);

$^1$H-NMR (CDCl$_3$): δ 0.05, 1.53, 3.14-3.46, 4.52, 7.14.

Example 42

1-(4,6-dichloro-2,2-difluoro-1-hydroxy-1-methyl-2,3-dihydro-1H-inden-5-yl)-3-(4-fluorobenzyl)urea

[Chem. 51]

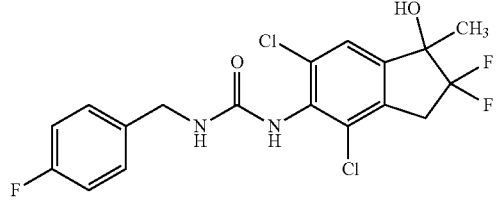

To a tetrahydrofuran (1.3 mL) solution of the compound (65 mg) produced in Example 41, diisopropylethylamine (36 µL) and triphosgene (62 mg) were added, followed by stirring at room temperature for 1 hour, and then, the reaction mixture was concentrated under reduced pressure. The resulting residue was dissolved in tetrahydrofuran (1.3 mL), and 1-(4-fluorophenyl)methanamine (CAS Registry Number: 140-75-0) (48 mg) was added thereto, followed by stirring at room temperature for 30 minutes. The reaction mixture was diluted with water, and extraction was performed with ethyl acetate. The organic layer was dried over anhydrous magnesium sulfate, and concentrated under reduced pressure. The resulting residue was dissolved in a mixed solvent of dichloromethane (1.2 mL) and methanol (1.2 mL), and trifluoroacetic acid (0.5 mL) was added thereto, followed by stirring at room temperature for 6 hours. The reaction mixture was concentrated under reduced pressure, and the resulting residue was diluted with a saturated aqueous sodium hydrogen carbonate solution, and then, extraction was performed with ethyl acetate. The organic layer was dried over anhydrous magnesium sulfate, and concentrated under reduced pressure. The resulting residue was purified by silica gel column chromatography (hexane:ethyl acetate=70:30→30:70), whereby the title compound was obtained (75 mg).

TLC: Rf 0.46 (hexane:ethyl acetate=1:1);

$^1$H-NMR (DMSO-d$_6$): δ 1.44, 3.38-3.47, 4.27, 6.10, 6.85, 7.12-7.18, 7.31-7.36, 7.47, 8.14

Example 42(1) to Example 42(2)

The titled compounds having the following physical property values were obtained by performing the same procedure as in Example 42 using a corresponding amine in place of 1-(4-fluorophenyl)methanamine.

Example 42(1)

1-(4,6-dichloro-2,2-difluoro-1-hydroxy-1-methyl-2,3-dihydro-1H-inden-5-yl)-3-[(1R)-1-(4-fluorophenyl)ethyl]urea TLC: Rf 0.48 (hexane:ethyl acetate=1:1):
$^1$H-NMR (DMSO-$d_6$): δ 1.38, 1.43, 3.36-3.45, 4.74-4.84, 6.09, 6.86, 7.12-7.18, 7.36-7.41, 7.45, 7.93

Example 42(2)

1-(4,6-dichloro-2,2-difluoro-1-hydroxy-1-methyl-2,3-dihydro-1H-inden-5-yl)-3-{[5-(trifluoromethyl)-2-pyridinyl]methyl}urea LC retention time (min): 0.86:
$^1$H-NMR (CD$_3$OD): δ 1.50, 3.33-3.48, 4.58-4.60, 7.17, 7.46, 7.63-7.66, 8.10-8.14, 8.81

Example 43(1)

1-(4,6-dichloro-2,2-difluoro-1-hydroxy-1-methyl-2,3-dihydro-1H-inden-5-yl)-3-(4-fluorobenzyl)urea (First Peak)

Example 43(2)

1-(4,6-dichloro-2,2-difluoro-1-hydroxy-1-methyl-2,3-dihydro-1H-inden-5-yl)-3-(4-fluorobenzyl)urea (Second Peak)

The compound (50 mg) produced in Example 42 was subjected to optical resolution by supercritical fluid chromatography (isopropyl alcohol=80:20, 30 mL/min), whereby the title compounds having the following physical property values were obtained (Example 43(1): 21.0 mg, Example 43(2): 23.0 mg).

Example 43(1)

SFC retention time: 3.94 min
TLC: Rf 0.39 (hexane:ethyl acetate=1:1);
$^1$H-NMR (DMSO-$d_6$): δ 1.44, 3.37-3.47, 4.26, 6.12, 6.87, 7.13-7.19, 7.31-7.36, 7.47, 8.16.

Example 43(2)

SFC retention time: 6.08 min
TLC: Rf 0.39 (hexane:ethyl acetate=1:1);
$^1$H-NMR (DMSO-$d_6$): δ 1.44, 3.37-3.47, 4.26, 6.12, 6.86, 7.13-7.19, 7.31-7.36, 7.47, 8.16.

Example 43(3)

1-(4,6-dichloro-2,2-difluoro-1-hydroxy-1-methyl-2,3-dihydro-1H-inden-5-yl)-3-[(1R)-1-(4-fluorophenyl)ethyl]urea (First Peak)

Example 43(4)

1-(4,6-dichloro-2,2-difluoro-1-hydroxy-1-methyl-2,3-dihydro-1H-inden-5-yl)-3-[(1R)-1-(4-fluorophenyl)ethyl]urea (Second Peak)

The compound (50 mg) produced in Example 42(1) was subjected to optical resolution by supercritical fluid chromatography (carbon dioxide:isopropyl alcohol=80:20, 30 mL/min), whereby the title compounds having the following physical property values were obtained (Example 43(3): 22.0 mg, Example 43(4): 21.0 mg).

Example 43(3)

SFC retention time: 3.02 min
TLC: Rf 0.48 (hexane:ethyl acetate=1:1);
$^1$H-NMR (DMSO-$d_6$): δ 1.38, 1.43, 3.35-3.46, 4.74-4.83, 6.10, 6.87, 7.13-7.19, 7.36-7.41, 7.45, 7.93.

Example 43(4)

SFC retention time: 5.68 min
TLC: Rf 0.48 (hexane:ethyl acetate=1:1);
$^1$H-NMR (DMSO-$d_6$): δ 1.37, 1.42, 3.36-3.45, 4.74-4.83, 6.10, 6.87, 7.13-7.19, 7.36-7.41, 7.45, 7.94.

The effects of the compound of the present invention can be demonstrated by the following experiments, but are not limited thereto.

(1) Biological Example 1: Opening Action with Respect to KCNQ2/3 Channel by Depolarization Stimulation Human KCNQ2/3 expression cells (CHO-DHFR– cells) were seeded in each well of a 384-well plate (collagen-coated, black, clear bottom) at $0.5 \times 10^4$ cells/50 μL per well and cultured using a MEM ALPHA medium (containing 10 vol % inactivated (56° C., 30 min) fetal bovine serum, 100 IU/mL penicillin, 100 μg/mL streptomycin, and 2 mM L-glutamine) at 37° C. in 5% $CO_2$ for 18 to 24 hours. After the medium in the plate was removed, incubation (room temperature, 60 minutes, shading) was performed in a loading buffer (prepared by the method described in the manual of FluxOR Thallium Detection Kit (Invitrogen, F10016, F10017)). A KCNQ2/3 channel opening action (thallium influx into cells) by depolarization stimulation (5 mM potassium and 0.5 mM thallium) was measured by FLIPR TETRA (Molecular Devices). The compound of the present invention was treated 5 minutes before the depolarization stimulation, and the reaction induced by the depolarization stimulation was measured over time for 180 seconds. The channel opening action of the compound of the present invention was evaluated based on the change amount of the fluorescence intensity from the time before the depolarization stimulation to the time after the elapse of 180 seconds, and the concentration (ECrtg50) satisfying 50% of the fluorescence intensity change of a maximum reaction (in the treatment at 10 μM) of retigabine under the conditions of this experiment was calculated.

The KCNQ2/3 channel opening action of the compound of the present invention was 100 μM or less in terms of ECrtg50 value. In Table 1, the opening actions (ECrtg50 values) with respect to the KCNQ2/3 channel of the following compounds as representative examples of the compound of the present invention are shown. As apparent also from Table 1, the compound of the present invention exhibited a strong opening action with respect to the KCNQ2/3 channel.

Further, in the above-mentioned method, by using human KCNQ4 or human KCNQ5 expression cells in place of the human KCNQ2/3 expression cells and appropriately changing the above-mentioned conditions based on the ordinary knowledge of those skilled in the art, the opening action with respect to the human KCNQ4 channel or the human KCNQ5 channel can be measured.

TABLE 1

| Compound | KCNQ2/3 ECrtg50 (μM) |
|---|---|
| Example 3(7) | 0.5 |
| Example 3(9) | 0.04 |
| Example 3(10) | 0.3 |
| Example 3(13) | 0.02 |
| Example 3(16) | 0.03 |
| Example 3(19) | 0.05 |
| Example 3(23) | 0.6 |
| Example 3(24) | 0.4 |
| Example 3(25) | 0.01 |
| Example 4(4) | 0.3 |
| Example 12 | 0.005 |
| Example 12(2) | 0.2 |
| Example 12(4) | 0.002 |
| Example 12(8) | 0.2 |
| Example 12(9) | 0.05 |
| Example 12(13) | 0.06 |
| Example 12(16) | 0.01 |
| Example 12(17) | 0.02 |
| Example 12(21) | 0.02 |
| Example 21 | 0.005 |
| Example 22 | 0.001 |
| Example 35 | 0.3 |
| Example 42 | 0.2 |

(1) Biological Example 2: Relaxing Action on Bladder Extracted from Rat

Female Jcl:Wistar rats (CLEA Japan, Inc., body weight at use: 170 to 200 g) were anesthetized by intraperitoneal administration of about 40 mg/kg of pentobarbital (Somnopentyl, Schering Plough Animal Health Corporation), and killed by bloodletting. The bladder was extracted by abdominal incision and immediately thereafter immersed in ice-cooled Krebs buffer (Krebs Ringer bicarbonate buffer (Sigma-Aldrich Co. LLC) supplemented with sodium hydrogen carbonate (final concentration: 15 mM) and calcium chloride (final concentration: 2.5 mM)) saturated with a mixed gas (95% $O_2$, 5% $CO_2$).

The bladder body extracted from each rat was cut into an oblong strip shape (about 10×3 mm), whereby a specimen was prepared on ice. Immediately thereafter, the specimen was suspended in a Magnus tube filled with Krebs buffer (37° C.) bubbled with the mixed gas while applying a tension load of 500 mg thereto. Incidentally, the specimen was prepared within 24 hours after extracting the tissue.

The change in tension of the specimen was recorded in data collection system (NR-1000, KEYENCE CORPORATION) through a Magnus system equipped with an isometric transducer (UFER UM-203, Iwashiya Kishimoto Medical Instruments) and an amplifier (UFER AP-5, Iwashiya Kishimoto Medical Instruments) and displayed on a computer via recorder analysis software WAVE THERMO 1000 (KEYENCE CORPORATION). After the elapse of one hour or more from the suspension of the specimen, 2.5 M KCl was added thereto to a final concentration of 100 mM, and the specimen in which a contraction reaction could be confirmed was used.

Carbachol (a contraction inducer) contraction was induced at a concentration of 1 μM. The specimens were arbitrarily assigned in groups so that a difference in the degree of contraction did not occur among the groups and the specimens collected from the same individual did not belong to the same group. After the contraction reaction was stabilized, physiological saline or the compound of the present invention was added thereto to a final concentration of 1 nM, 10 nM, 100 nM, 1 μM, and 10 M in a cumulative manner from a low concentration.

The tension (mg) in the extracted bladder was used as an evaluation item. The tension was read using analysis software WAVE THERMO 1000. A percent change in tension after adding the compound of the present invention when the tension after adding the contraction inducer was taken as 0% was defined as a percent change in tension (%) and used as an evaluation index. The percent change in tension (%) is calculated according to the following formula.

percent change in tension (%)={tension (mg) after adding compound of the present invention and the like–tension (mg) before adding contraction inducer}/{tension (mg) after adding contraction inducer–tension (mg) before adding contraction inducer}×100–100

The value at which the percent change in tension (%) was –20% was calculated as $IC_{20}$ and used as an index of the relaxing action on the extracted bladder.

The compounds produced in Examples 12, 12(4), 12(5), and 42 showed $IC_{20}$ values of 0.01, 0.01, 0.03, and 0.1 μM, respectively. As represented by the above-mentioned compounds, the compound of the present invention had a relaxing action on the bladder extracted from the rat. Therefore, the compound of the present invention is useful as a therapeutic agent for overactive bladder.

(3) Solubility Test

A calibration curve solution was prepared at 0.1, 0.4, and 2 μM by diluting a test substance (a 10 mM DMSO solution) with acetonitrile and adding acetonitrile containing an internal standard substance (candesartan).

A sample solution was prepared as follows. 5 μL of the compound of the present invention (a 10 mM DMSO solution) was added to 495 μL of the Japanese Pharmacopoeia dissolution test second solution (pH: 6.8), followed by stirring at room temperature for 5 hours. Then, the solution was transferred to a solubility filter plate and subjected to suction filtration. The filtrate (20 μL) was diluted with acetonitrile, followed by adding acetonitrile containing an internal standard substance (candesartan).

Each of the calibration curve and sample solutions (5 μL) was injected into LC-MS/MS (Discovery Max, manufactured by Thermo Scientific, Inc.) and subjected to quantification (quantification range: 5 to 100 μM). The solubility in the case where the value equal to or less than the quantification range was obtained was defined as <5 μM, and the solubility in the case where the value equal to or more than the quantification range was obtained was defined as 100 μM.

The results are shown in Table 2. As apparent from Table 2, the compound of the present invention represented by the compounds shown in Table 2 exhibited an excellent solubility.

TABLE 2

| Compound | Solubility (μM) |
|---|---|
| Example 3(7) | 86 |
| Example 3(13) | 92 |
| Example 3(19) | 76 |
| Example 3(23) | 83 |
| Example 12 | 82 |
| Example 12(2) | 85 |
| Example 12(4) | 87 |
| Example 12(8) | 94 |

TABLE 2-continued

| Compound | Solubility (μM) |
| --- | --- |
| Example 12(13) | 78 |
| Example 21 | 72 |
| Example 35 | 80 |
| Example 42 | 87 |

(4) Evaluation of Stability in Human Liver Microsomes

A test compound (a 10 mM DMSO solution, 5 μL) was diluted with a 50% aqueous acetonitrile solution (195 μL), whereby a 0.25 mM solution was prepared.

To a reaction vessel preheated to 37° C., 0.5 mg/mL of human liver microsomes (XenoTech, LLC) and 245 JLL of a 0.1 M phosphate buffer solution (pH 7.4) containing NADPH co-factor (BD Biosciences) were added, followed by preincubation for 5 minutes, and thereafter, the above-prepared test compound solution (5 μL) was added thereto to start a reaction (final concentration: 5 μM). Immediately after the start, a 20 μL portion was collected and added to 180 μL of acetonitrile containing an internal standard substance (warfarin) to stop the reaction. A 20 μL portion of this solution was stirred with 180 μL of a 50% aqueous acetonitrile solution on a plate equipped with a deproteinization filter, followed by suction filtration, and the filtrate was used as a standard sample.

After the above-prepared reaction solution was incubated at 37° C. for 15 minutes, a 20 μL portion of the solution was added to 180 μL of cooled acetonitrile (containing warfarin serving as an internal standard substance) to stop the reaction. A 20 μL portion of this solution was stirred with 180 μL of a 50% aqueous acetonitrile solution on a plate equipped with a deproteinization filter, followed by suction filtration, and the filtrate was used as a reaction sample.

A residual ratio (%) was calculated as follows. 1 μL of the sample solution was injected into LC-MS/MS (Discovery Max, manufactured by Thermo Scientific, Inc.), and a value obtained by dividing the peak area ratio of the reaction sample (peak area of test compound/peak area of internal standard substance) by the peak area ratio of the standard sample was multiplied by 100.

The results are shown in Table 3. As apparent from Table 3, it was found that the compound of the present invention represented by the compounds shown in Table 3 has high stability against the human liver microsomes, and has excellent metabolic stability.

TABLE 3

| Compound | Residual ratio (%) |
| --- | --- |
| Example 3(19) | 83 |
| Example 4(4) | 98 |
| Example 12 | 94 |
| Example 12(4) | 77 |
| Example 12(8) | 100 |
| Example 12(13) | 100 |
| Example 21 | 95 |
| Example 35 | 81 |
| Example 42 | 90 |

(5) Evaluation of Action on hERG IKr Current

By using HEK293 cells overexpressing a human ether-a-go-go-related gene (hERG), the maximum tail current of the hERG IKr current induced by redepolarization pulse subsequent to depolarization pulse was measured by a patch-clamp method, and the percent change (suppression ratio) after 10 minutes from application of a test substance with respect to the maximum tail current before the application of the test substance was calculated (see, Biophysical Journal, vol. 74, pp. 230-241 (1998)).

The 50% hERG channel inhibitory activity of each of the compounds produced in Examples 4(4), 12, 12(5), and 42 was >10 μM. As represented by the above-mentioned compounds, it was found that the compound of the present invention is a compound which has a low possibility of inducing QT extension due to a drug, and therefore has excellent safety.

FORMULATION EXAMPLES

Representative formulation examples to be used in the present invention will be shown below.

Formulation Example 1

The following respective components are mixed by a conventional method, followed by tableting, whereby 10,000 tablets containing 10 mg of the active ingredient per tablet are obtained:
1-[4,6-dichloro-1-hydroxy-1-(trifluoromethyl)-2,3-dihydro-1H-inden-5-yl]-3-{[5-(trifluoromethyl)-2-pyridinyl]methyl}urea (100 g);
carboxymethyl cellulose calcium (disintegrating agent) (20 g);
magnesium stearate (lubricant) (10 g); and
microcrystalline cellulose (870 g).

Formulation Example 2

The following respective components were mixed by a conventional method, followed by filtration through a dust removal filter, and a 5 mL portion of the filtrate was filled into ampoules, and the ampoules were subjected to heat sterilization in an autoclave, whereby 10,000 ampoules containing 20 mg of the active ingredient per ample are obtained:
1-[4,6-dichloro-1-hydroxy-1-(trifluoromethyl)-2,3-dihydro-1H-inden-5-yl]-3-{[5-(trifluoromethyl)-2-pyridinyl]methyl}urea (200 g):
mannitol (2 kg); and
distilled water (50 L).

INDUSTRIAL APPLICABILITY

The compound of the present invention has sufficiently low toxicity, and can be used safely as a pharmaceutical product and is useful as a therapeutic agent for a KCNQ2-5 channel-related disease.

The invention claimed is:

1. A compound represented by the general formula (I) or a pharmaceutically acceptable salt thereof:

(I)

$$R^9\text{-}Z\text{-}[CR^{10}R^{11}]_n\text{-}Y\text{-}C(O)\text{-}NH\text{-}\text{Ar}(R^2,R^3,R^4,R^5,R^6,R^7,R^8,R^1O)$$

wherein R¹ is (1) a hydrogen atom or (2) a $C_{1-4}$ alkyl group; R² is (1) a hydrogen atom or (2) a $C_{1-4}$ alkyl group which may be substituted with a halogen; R³, R⁴, R⁵, and R⁶ are each independently (1) a hydrogen atom, (2) a halogen, or (3) a $C_{1-4}$ alkyl group which may be substituted with a halogen; R⁷ and R⁸ are each independently (1) a halogen, (2) a $C_{1-4}$ alkyl group which may be substituted with a halogen, or (3) a $C_{1-4}$ alkoxy group which may be substituted with a halogen; Y is (1) a bond, (2) —NH—, or (3) —O—; Z is (1) a bond, (2) —NR¹²—, or (3) —O—; R¹² is (1) a hydrogen atom, (2) a $C_{1-4}$ alkyl group which may be substituted with a halogen, or (3) a $C_{2-5}$ acyl group which may be substituted with a halogen; R¹⁰ and R¹¹ are each independently (1) a hydrogen atom or (2) a $C_{1-4}$ alkyl group which may be substituted with a halogen or a hydroxy group; n is an integer of 1 to 4, and when n is 2 to 4, a plurality of R¹⁰'s or a plurality of R¹¹'s may be the same as or different from one another; R⁹ is (1) a ring A, (2) a $C_{1-4}$ alkyl group, (3) a $C_{2-4}$ alkenyl group, (4) a $C_{2-4}$ alkynyl group, (5) —$C_{1-4}$ alkylene group-ring A, (6) —$C_{2-4}$ alkenylene group-ring A, (7) —$C_{2-4}$ alkynylene group-ring A, (8) -ring B-ring C, (9) -ring B—$C_{1-4}$ alkylene group-ring C, (10) -ring B—$C_{2-4}$ alkenylene group-ring C, (11) -ring B—$C_{2-4}$ alkynylene group-ring C, or (12) -ring B—O-ring C, where the alkyl group, the alkenyl group, the alkynyl group, the alkylene group, the alkenylene group, or the alkynylene group each may be substituted with a halogen or a hydroxy group; the ring A is (1) a $C_{3-8}$ cycloalkane, (2) a 3- to 8-membered heterocycloalkane, (3) a $C_{3-12}$ monocyclic or bicyclic unsaturated carbocyclic ring or the carbocyclic ring which may be partially saturated, or (4) a 3- to 12-membered monocyclic or bicyclic unsaturated heterocycle containing one to four heteroatoms selected from an oxygen atom, a nitrogen atom, and a sulfur atom or the heterocycle which may be partially saturated; the ring B and the ring C are each independently (1) a $C_{3-8}$ monocyclic cycloalkane, (2) a 3- to 8-membered monocyclic heterocycloalkane, (3) a $C_{3-7}$ monocyclic unsaturated carbocyclic ring or the carbocyclic ring which may be partially saturated, or (4) a 3- to 7-membered monocyclic unsaturated heterocycle containing one to three heteroatoms selected from an oxygen atom, a nitrogen atom, and a sulfur atom or the heterocycle which may be partially saturated; where the ring A, the ring B, and the ring C may be each independently substituted with one to five R¹³'s, and when a plurality of R¹³'s is present, the R¹³'s may be the same as or different from one another; R¹³ is (1) a halogen, (2) a hydroxy group, (3) a cyano group, (4) a $C_{1-6}$ alkyl group which may be substituted with a halogen or a hydroxy group, (5) a $C_{1-6}$ alkoxy group which may be substituted with a halogen or a hydroxy group, or (6) an amino group which may be substituted with a $C_{1-4}$ alkyl group or a $C_{2-5}$ acyl group.

2. The compound or a pharmaceutically acceptable salt thereof according to claim 1, wherein R¹ is a hydrogen atom.

3. The compound or a pharmaceutically acceptable salt thereof according to claim 1, wherein Y is —NH— or —O—.

4. The compound or a pharmaceutically acceptable salt thereof according to claim 1, wherein Z is a bond or —O—.

5. The compound or a pharmaceutically acceptable salt thereof according to claim 1, wherein R² is a hydrogen atom, a methyl group, or a trifluoromethyl group.

6. The compound or a pharmaceutically acceptable salt thereof according to claim 1, wherein the compound is (1) 1-(4,6-dichloro-1-hydroxy-1-methyl-2,3-dihydro-1H-inden-5-yl)-3-{[5-(trifluoromethyl)-2-pyridinyl]methyl}urea, (2) 1-[4,6-dichloro-1-hydroxy-1-(trifluoromethyl)-2,3-dihydro-1H-inden-5-yl]-3-(4-fluorobenzyl)urea, (3) 1-[4,6-dichloro-1-hydroxy-1-(trifluoromethyl)-2,3-dihydro-1H-inden-5-yl]-3-{[5-(trifluoromethyl)-2-pyridinyl]methyl}urea, (4) 1-[4,6-dichloro-1-hydroxy-1-(trifluoromethyl)-2,3-dihydro-1H-inden-5-yl]-3-[(1R)-1-(4-fluorophenyl)ethyl]urea, or (5) 1-(4,6-dichloro-2,2-difluoro-1-hydroxy-1-methyl-2,3-dihydro-1H-inden-5-yl)-3-(4-fluorobenzyl)urea.

7. The compound or a pharmaceutically acceptable salt thereof according to claim 1, wherein the compound is 1-[(1R)-4,6-dichloro-1-hydroxy-1-(trifluoromethyl)-2,3-dihydro-1H-inden-5-yl]-3-[(1R)-1-(4-fluorophenyl)ethyl]urea or 1-[(1S)-4,6-dichloro-1-hydroxy-1-(trifluoromethyl)-2,3-dihydro-1H-inden-5-yl]-3-[(1R)-1-(4-fluorophenyl)ethyl]urea.

8. A pharmaceutical composition comprising the compound according to claim 1 or a pharmaceutically acceptable salt thereof and a pharmaceutically acceptable carrier.

9. A method for treating a KCNQ2-5 channel-related disease, comprising administering an effective amount of the compound according to claim 1 or a pharmaceutically acceptable salt thereof to a mammal with a KCNQ2-5 channel-related disease.

* * * * *